(12) United States Patent
Birbara

(10) Patent No.: US 11,491,226 B2
(45) Date of Patent: *Nov. 8, 2022

(54) METHODS OF INCREASING SOLUBILITY OF POORLY SOLUBLE COMPOUNDS AND METHODS OF MAKING AND USING FORMULATIONS OF SUCH COMPOUND

(71) Applicant: TECHNOLOGY INVESTMENTS LC, Fairfax, VA (US)

(72) Inventor: Philip J. Birbara, West Hartford, CT (US)

(73) Assignee: TECHNOLOGY INVESTMENTS LC, Fairfax, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/947,707

(22) Filed: Aug. 13, 2020

(65) Prior Publication Data
US 2021/0000958 A1  Jan. 7, 2021

Related U.S. Application Data

(60) Continuation of application No. 15/637,370, filed on Jun. 29, 2017, now abandoned, which is a continuation of application No. 14/107,572, filed on Dec. 16, 2013, now Pat. No. 9,730,953, which is a division of application No. 13/064,882, filed on Apr. 22, 2011, now Pat. No. 8,637,569, which is a continuation-in-part of application No. PCT/US2010/002821, filed on Oct. 22, 2010.

(60) Provisional application No. 61/253,857, filed on Oct. 22, 2009.

(51) Int. Cl.

| | | |
|---|---|---|
| *A61K 47/26* | (2006.01) |
| *A61K 8/49* | (2006.01) |
| *A61K 9/00* | (2006.01) |
| *A61K 9/70* | (2006.01) |
| *A61K 31/00* | (2006.01) |
| *A61K 31/353* | (2006.01) |
| *A61K 31/05* | (2006.01) |
| *A61K 31/7048* | (2006.01) |
| *A61K 31/352* | (2006.01) |
| *A61K 47/10* | (2017.01) |
| *A61K 47/20* | (2006.01) |
| *A61Q 17/04* | (2006.01) |
| *A61Q 19/00* | (2006.01) |
| *A23L 33/10* | (2016.01) |
| *A23L 2/52* | (2006.01) |

(52) U.S. Cl.
CPC ............ *A61K 47/26* (2013.01); *A23L 2/52* (2013.01); *A23L 33/10* (2016.08); *A61K 8/498* (2013.01); *A61K 9/0014* (2013.01); *A61K 9/0095* (2013.01); *A61K 9/7023* (2013.01); *A61K 31/00* (2013.01); *A61K 31/05* (2013.01); *A61K 31/352* (2013.01); *A61K 31/353* (2013.01); *A61K 31/7048* (2013.01); *A61K 47/10* (2013.01); *A61K 47/20* (2013.01); *A61Q 17/04* (2013.01); *A61Q 19/00* (2013.01); *A23V 2002/00* (2013.01); *A61K 2800/412* (2013.01); *A61K 2800/592* (2013.01); *A61K 2800/652* (2013.01)

(58) Field of Classification Search
CPC ...... A61K 47/26; A61K 8/498; A61K 9/0014; A61K 9/0095; A61K 9/7023; A61K 31/00; A61K 31/05; A61K 31/352; A61K 31/353; A61K 31/7048; A61K 47/10; A61K 47/20; A61K 2800/412; A61K 2800/592; A61K 2800/652; A23L 33/10; A23L 2/52; A61Q 17/04; A61Q 19/00; A23V 2002/00
See application file for complete search history.

(56) References Cited

U.S. PATENT DOCUMENTS

| | | |
|---|---|---|
| 2,421,061 A | 5/1947 | Higby |
| 2,442,110 A | 5/1948 | Baier |
| 2,700,047 A | 1/1955 | Wilson |
| 4,603,046 A | 7/1986 | Georgalas et al. |
| 5,043,323 A | 8/1991 | Bombardelli et al. |
| 6,099,825 A | 8/2000 | McShane et al. |
| 6,409,996 B1 | 6/2002 | Plaschke |
| 6,440,432 B1 | 8/2002 | Mukherjee et al. |

(Continued)

FOREIGN PATENT DOCUMENTS

| | | |
|---|---|---|
| AU | 2011318580 | 1/2016 |
| AU | 2010308571 | 10/2016 |

(Continued)

OTHER PUBLICATIONS

English translation of CN-101164536-A provided by EPO. (Year: 2022).*

(Continued)

*Primary Examiner* — Michael P Cohen
(74) *Attorney, Agent, or Firm* — Nixon & Vanderhye, PC

(57) ABSTRACT

The subject invention relates to novel soluble forms of planar ring structured organic compounds including flavonoids, and their production. The invention also includes the use of these novel formulations of planar ring structured organic compounds in the preparation of formulations and products. The invention also relates to a wide variety of applications of the formulations of the invention. The subject invention includes novel soluble forms and various formulations of flavonoids. Further, the invention includes novel methods of manufacturing the flavonoid formulations. The invention also relates to a wide variety of applications of the flavonoid formulations.

22 Claims, 3 Drawing Sheets

(56) References Cited

U.S. PATENT DOCUMENTS

| | | |
|---|---|---|
| 6,814,959 B1 | 11/2004 | Müller et al. |
| 6,890,561 B1 | 5/2005 | Blatt et al. |
| 7,235,295 B2 | 6/2007 | Laurencin et al. |
| 7,387,805 B2 | 6/2008 | Tsuzaki et al. |
| 7,858,080 B2 | 12/2010 | Chung et al. |
| 7,919,113 B2 | 4/2011 | Domb |
| 9,730,953 B2 * | 8/2017 | Birbara .......... A61Q 17/04 |
| 2002/0054891 A1 | 5/2002 | Anderson et al. |
| 2003/0119909 A1 | 6/2003 | Stanislaus |
| 2004/0058983 A1 | 3/2004 | Vuorela et al. |
| 2004/0081670 A1 | 4/2004 | Behnam |
| 2004/0191300 A1 | 9/2004 | Fecht et al. |
| 2004/0220116 A1 | 11/2004 | Behnam |
| 2005/0049291 A1 | 3/2005 | Kumar et al. |
| 2005/0209313 A1 | 9/2005 | Wallace |
| 2005/0281869 A1 | 12/2005 | Kruse et al. |
| 2006/0040894 A1 | 2/2006 | Hunter et al. |
| 2006/0078630 A1 | 4/2006 | Schempp et al. |
| 2006/0099270 A1 | 5/2006 | Friggeri et al. |
| 2006/0110415 A1 | 5/2006 | Gupta |
| 2006/0257334 A1 | 11/2006 | Dahms et al. |
| 2007/0003502 A1 | 1/2007 | Tanabe et al. |
| 2007/0140984 A1 | 6/2007 | Kusano et al. |
| 2008/0254188 A1 | 10/2008 | Borowy-Borowski et al. |
| 2010/0047297 A1 | 2/2010 | Petersen |
| 2010/0183524 A1 | 7/2010 | Zielinski et al. |
| 2011/0184072 A1 | 7/2011 | Pechere |
| 2011/0223256 A1 | 9/2011 | Zhang et al. |
| 2012/0128777 A1 | 5/2012 | Keck et al. |
| 2012/0148567 A1 | 6/2012 | Kurisawa et al. |
| 2012/0213842 A1 | 8/2012 | Birbara |

FOREIGN PATENT DOCUMENTS

| | | |
|---|---|---|
| CN | 1356327 | 7/2002 |
| CN | 101164536 | 4/2008 |
| CN | 101164536 A * | 4/2008 |
| CN | 101518262 | 9/2009 |
| CN | 1761450 | 5/2010 |
| DE | 101 03 454 | 8/2002 |
| DE | 101 29 973 | 1/2003 |
| DE | 102 60 872 | 7/2004 |
| EP | 0 179 583 | 4/1986 |
| EP | 1 600 143 | 11/2005 |
| EP | 1 731 134 | 12/2006 |
| EP | 2 359 702 | 8/2011 |
| JP | 10-101705 | 4/1998 |
| JP | 2004-531530 | 10/2004 |
| JP | 2005-185237 | 7/2005 |
| JP | 2005-521629 | 7/2005 |
| JP | 2005-526785 | 9/2005 |
| JP | 2007-197328 | 8/2007 |
| JP | 5965319 | 8/2016 |
| JP | 6105475 | 3/2017 |
| KR | 10-2005-0102686 | 10/2005 |
| KR | 10-1734424 | 5/2017 |
| MX | 338211 | 3/2016 |
| WO | WO 01/03652 | 1/2001 |
| WO | WO 03/000191 | 1/2003 |
| WO | WO 03/080024 | 10/2003 |
| WO | WO 2006/020164 | 2/2006 |
| WO | WO 2007/006497 | 2/2006 |
| WO | WO 2007/000193 | 1/2007 |
| WO | WO 2008/072954 | 6/2008 |
| WO | WO 2008/101344 | 8/2008 |
| WO | WO 2010/007252 | 1/2010 |
| WO | WO 2010/062824 | 6/2010 |
| WO | WO 2010/062835 | 6/2010 |
| WO | WO 2010/121700 | 10/2010 |
| WO | WO 2011/047227 | 4/2011 |
| WO | WO 2011/089247 | 7/2011 |
| WO | WO 2011/149854 | 12/2011 |
| WO | WO 2012/003515 | 1/2012 |

OTHER PUBLICATIONS

Abstract of Hertel et al., "Inhibitory effects of triterpenes and flavonoids on the enzymatic activity of hyaluronic acid-splitting enzymes," *Arch. Pharm. (Weinheim)*, vol. 339, No. 6: 313-8 (2006).

Abstract of Liu et al., "Preparation of apigenin niosomes and properties investigation," *Journal of Shenyang Pharmaceutical University*, vol. 26, No. 6: 423-429 (2009).

Blanco-Andujar et al., "Synthesis of nanoparticles for biomedical applications," *Annu. Rep. prog. Chem.*, Sect. A, No. 106: 553-568 (2010).

Bowen, "Particle Size Distribution Measurement from Millimeters to Nanometers and from Rods to Platelets," *Journal of Dispersion Science and Technology*, vol. 23, No. 5: 631-662 (2002), Marcel Dekker, Inc., New York.

Brown et al., Hyaluronic acid: a unique topical vehicle for the localized delivery of drugs to the skin. JEADV (2005) 19, 308-318.

Casetti et al., "Topical application of solubilized *Reseda luteola* extract reduces ultraviolet B-induced inflammation in vivo," *Journal of Photochemistry and Photobiology B: Biology*, vol. 96: 260-265 (2009).

Chebil et al., "Solubility of Flavonoids in Organic Solvents", J. Chem. Eng. Data 52:1552-1556 (2007).

Chen et al., "A facile nanoaggregation strategy for oral delivery of hydrophobic drugs by utilizing acid-base neutralization reactions," *Nanotechnology*, vol. 19, No. 375104: 1-7 (2008).

Chen Ping et al. A Study on the Complex Reaction, Between Apigenin and Zinc. *Journal of Food Science*, vol. 29, 8, 151-154, Dec. 31, 2008.

Choi et al., "Influence of heat treatment on the antioxidant activities and polyphenolic compounds of Shiitake (*Lentinus edodes*) mushroom", *Food Chemistry* 99:381-387 (2006).

Engstrom et al., "Templated Open Floes of Nanorods for Enhanced Pulmonary Delivery with Pressurized Metered Dose Inhalers," *Pharmaceutical Research*, vol. 26, No. 1: 101-117 (Jan. 2009).

Iqbal et al., "Stabilization of sunflower oil by garlic extract during accelerated storage", Food Chemistry 100(1):246-254 (2007).

Kim et al., "Aqueous Solubility Enhancement of Some Flavones by Complexation with Cyclodextrins", Bull. Korean Chem. Soc. 29:590-594 (2008).

Li et al., "Evaluation of Properties of Apigenin and [G-$^3$H]Apigenin and Analytic Method Development", Journal of Pharmaceutical Sciences 86(6):721-725 (1997).

Li et al., "Solubilization of Flavopiridol by pH Control Combined with Cosolvents, Surfactants, or Complexants", Journal of Pharmaceutical Sciences 88(9):945-947 (1999).

Li et al., "Solubilization of Ionized and Un-ionized Flavopiridol by Ethanol and Polysorbate 20", Journal of Pharmaceutical Sciences 88(5):507-509 (1999).

Li Ming (Ed.). *Extracting Technologies and Examples*, (pp. 83-85). Chemical Industry Press, Sep. 30, 2006.

Lucky Vitamin, "Derma-E—Hydrating Eye Creme with Hyaluronic Acid and Pycogenol—0.5 oz.," http://www.luckyvitamin.com/PrintProduct.aspx?ProductID= 13044.

Mandal et al., "Modulation of the Photophysical Properties of Curcumin in Nonionic Surfactant (Tween-20) Forming Micelles and Niosomes: A Comparative Study of Different Microenvironmentsm," J. Phys. Chem. B 2013, 117, 6957-6968.

MSDS for Genistein from LC Laboratories, downloaded from the internet on May 31, 2012 from the site: http://www.lclabs.com/MSDS/G-6055MSDS.php4.

Patel et al., "Ineraction of Some Pharmaceuticals with Macromolecules I: Effect of Temperature on the Binding of Parabens and Phenols by Polysorbate 80 and Polyethylene Glycol 4000", Journal of Phumaceutunl. Sciences 53(1):94-97 (1964).

Remington, "The Science and Practice Pharmacy", 21$^{st}$ Edition, Troy, David B, Editor, Baltimore: Lippincott Williams and Wilkins, p. 324 (2006).

Rodriguez-Tenreiro et al., "Estradiol sustained release from high affinity cyclodextrin hydrogels", European Journal of Pharmaceutics and Biopharmaceutics 66(1):55-62 (2007).

(56) References Cited

OTHER PUBLICATIONS

SOOFT | TRIUM collirio; SOOFT italia goup homepage; Trium Eye Drops and Trium Monodose; http://www.oogroup.it/sooft/en/md_trium_collirio.html.

Taiyouko Co., Ltd., "Taplis," <<http://www.taiyouko.co.jp/export/c_taplis.html>>, retrieved on Mar. 11, 2015.

Tang et al., "Preparation of Self-emulsifying Drug Delivery Systems of *Ginkgo biloba* Extracts and in vitro Dissolution Studies", Asian Journal of Traditional Medicines 1(3-4):1-4 (2006).

Tommasini et al., "Improvement in solubility and dissolution rate of flavonoids by complexation with β-cyclodextrin", Journal of Pharmaceutical and Biomedical Analysis 35:379-387 (2004).

Tungjai et al., "Spectrophotometric Characterization of Behavior and the Predominant Species of Flavonoids in Physiological Buffer: Determination of Solubility, Lipophilicity and Anticancer Efficacy," *The Open Drug Delivery Journal*, vol. 2: 10-19 (2008).

Uchegbu et al., "Non-ionic surfactant based vesicles (niosomes) in drug delivery," International Journal of Pharmaceutics 172 (1998) 33-70.

Ultra HA Plus—Hyaluronic Acid Serum from Great American Health, Ultra HA plus—Skin and Joint Hydrating Support, http://greatamericanhealth.com/ultra-ha-plus/.

Wang et al., "Antioxidant effect of natural flavonoids and research developments of its extracting technique", Review 11(5):1-10 (2004).

Yao et al., "Preparation of nobiletin in self-microemulsifying systems and intestinal permeability in rats", J. Pharm. Pharmaceut. Sci. 11(3):22-29 (2008).

Australian Examination Report issued in Appln. No. 2018200079 dated May 22, 2018.

Australian Office Action issued in App. No. 2010308571 dated Jan. 15, 2016.

Australian Office Action issued in App. No. 2016202145 dated Nov. 28, 2016.

Canadian Office Action issued in App. No. 2,778,441 dated Jul. 4, 2016.

Chinese Office Action issued in App. No. 201080058485.X dated Aug. 11, 2015 (w/translation).

Chinese Office Action issued in App. No. 201080058485.X dated Nov. 14, 2014 (w/ translation).

Chinese Office Action issued in App. No. 201180062179.8 dated Jul. 3, 2014 (translation only).

Chinese Office Action issued in App. No. 201180062179.8 dated Mar. 6, 2015 (w/translation).

European Office Action issued in App. No. 10 774 319.7 dated Nov. 7, 2014.

European Office Action issued in App. No. 10 774 319.7 dated Nov. 10, 2016.

Extended European Search Report issued in Appln. No. 17199056.7 dated May 18, 2018.

International Search Report issued in PCT/US2010/002821 dated Apr. 18, 2011.

International Search Report issued in PCT/US2011/001802 dated Feb. 8, 2012.

Japanese Office Action issued in App. No. 2012-535193 dated Oct. 14, 2014 (w/translation).

Japanese Office Action issued in App. No. 2013-534896 dated Aug. 1, 2016 (w/translation).

Korean Office Action issued in App. No. 10-2013-7013011 dated Sep. 12, 2016 (w/ trans.).

Korean Office Action issued in App. No. 2012-7010346 dated Oct. 7, 2016 (w/translation).

U.S. Office Action issued in U.S. Appl. No. 13/503,458 dated Dec. 4, 2013.

U.S. Office Action issued in U.S. Appl. No. 13/503,458 dated Sep. 25, 2014.

U.S. Office Action issued in U.S. Appl. No. 13/503,458 dated Sep. 20, 2016.

\* cited by examiner

FIGURE 1 - Surfactant Classification According to the Composition of their Head: Nonionic, Anionic, Cationic, Amphoteric.
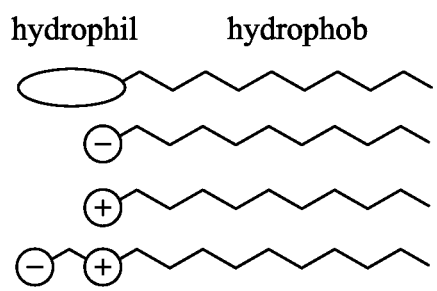

Example 1
FIGURE 2 - MASS SPECTROSCOPY ANALYTICAL RESULTS COMPARING OUR PS80/APIGENIN STOCK SOLUTION WITH VIRGIN PS89
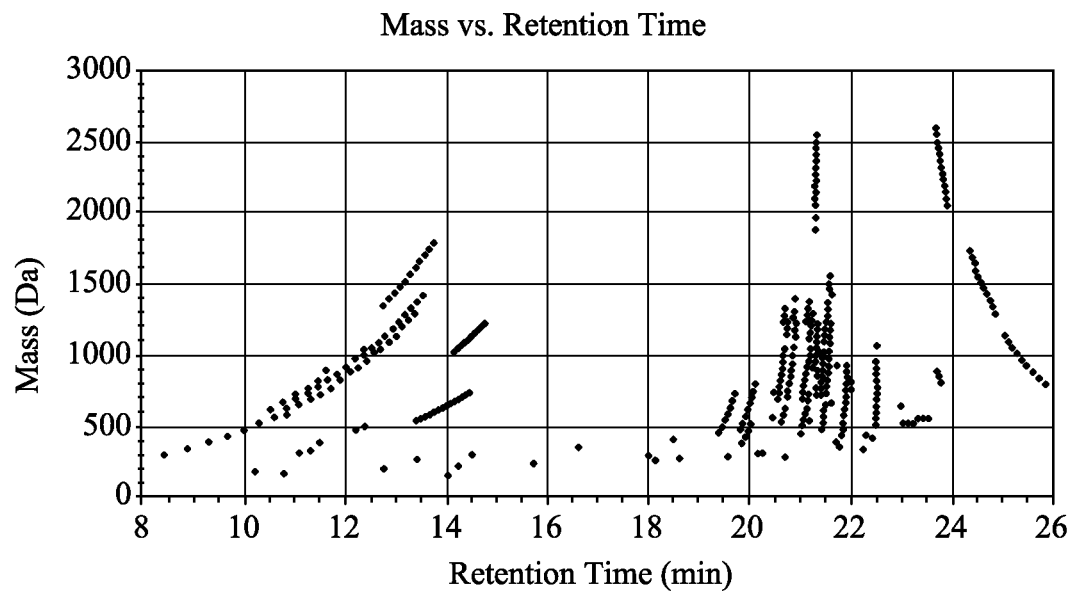
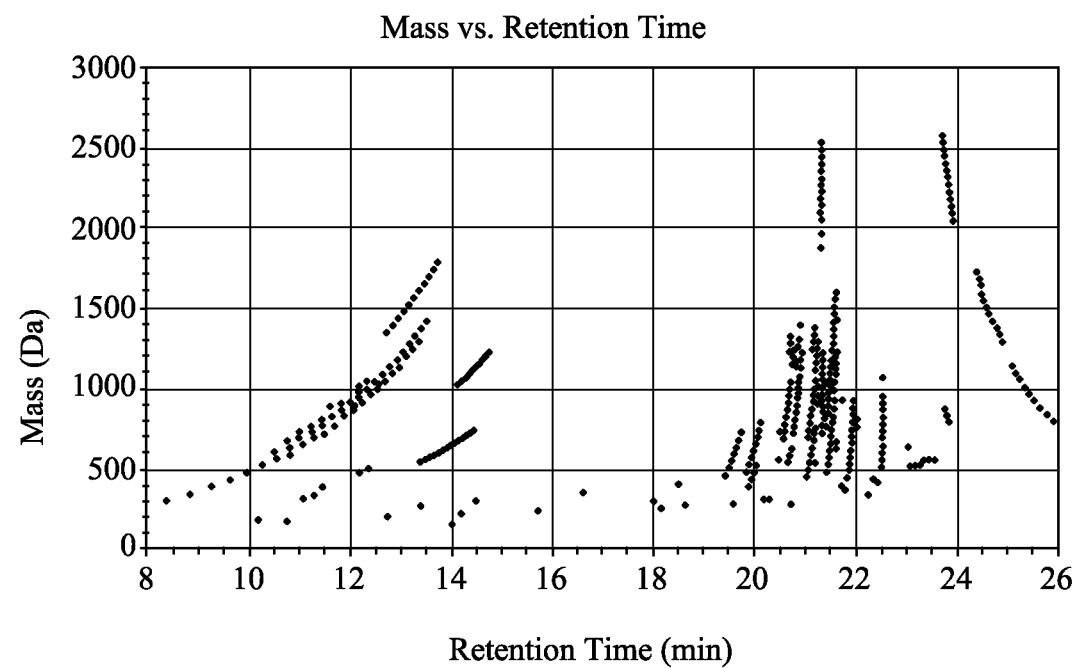

FIGURE 3
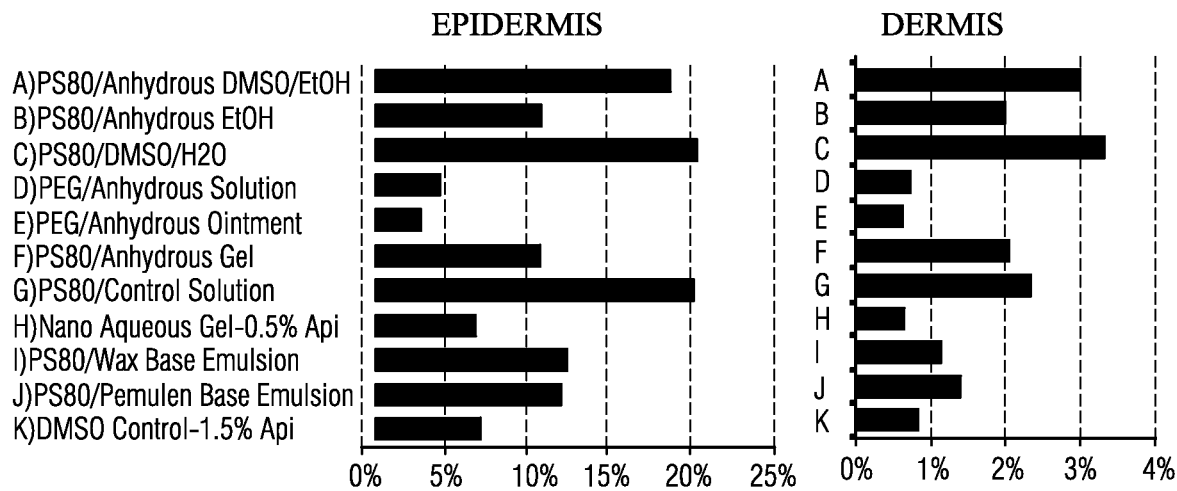
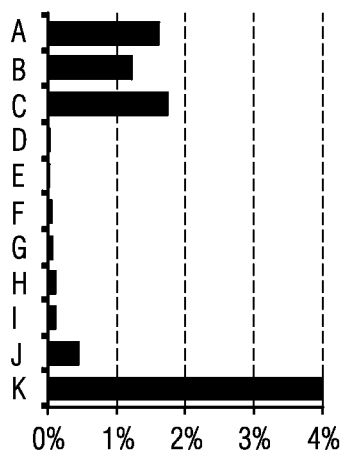
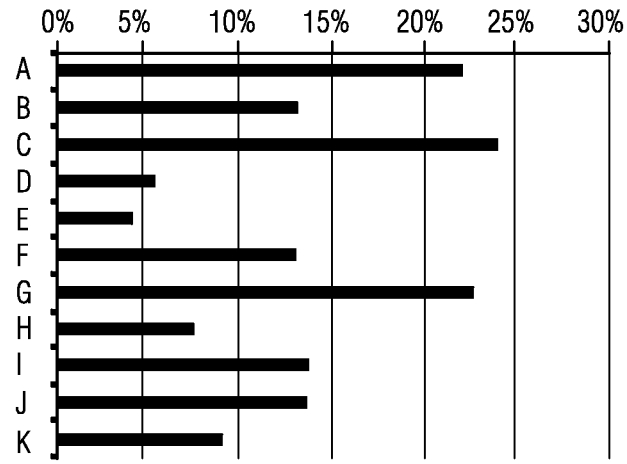

METHODS OF INCREASING SOLUBILITY OF POORLY SOLUBLE COMPOUNDS AND METHODS OF MAKING AND USING FORMULATIONS OF SUCH COMPOUND

This application is a continuation of Ser. No. 15/637,370 filed Jun. 29, 2017, which is a continuation of Ser. No. 14/107,572 filed Dec. 16, 2013 (now U.S. Pat. No. 9,730,953), which is a divisional of Ser. No. 13/064,882 filed Apr. 22, 2011 (now U.S. Pat. No. 8,637,569), which is a continuation-in-part of PCT/US2010/002821 filed Oct. 22, 2010 which claims priority to Provisional Application No. 61/253,857 filed Oct. 22, 2009, the entire contents of each which are hereby incorporated by reference.

The subject invention relates to novel soluble forms of planar ring structured organic compounds including flavonoids, and their production. The invention also includes the use of these novel formulations of planar ring structured organic compounds in the preparation of formulations and products. The invention also relates to a wide variety of applications of the formulations of the invention.

BACKGROUND OF THE ART

Flavonoids

The principle plant-derived agents believed to provide protection against cancer are flavonoids and dietary fiber. (Patel, D, et al., *Apigenin and cancer chemoprevention: Progress, potential, and promise, Intl. J. Oncology* 2007 January; 30(1): 233-45.) Chemoprevention is a facet of oncology that focuses on the prevention of cancer through naturally occurring or synthetic agents.

Flavonoids have been shown to act as free radical scavengers, anti-oxidants, superoxide anions, UV absorbers, and lipid peroxide radicals. Flavonoid compounds are also known to be effective in strengthening collagen structures. Further, flavonoids have been shown to exhibit anti-mutagenic, anti-inflammatory, and antiviral effects.

All flavonoids have the same basic chemical structure, a three-ringed molecule. Individual flavonoids in a group differ from each other by the number and position of substituents (e.g.s the hydroxy, methoxy, or sugar groups). Flavonoids have the planar aromatic ring structures following general formulas:

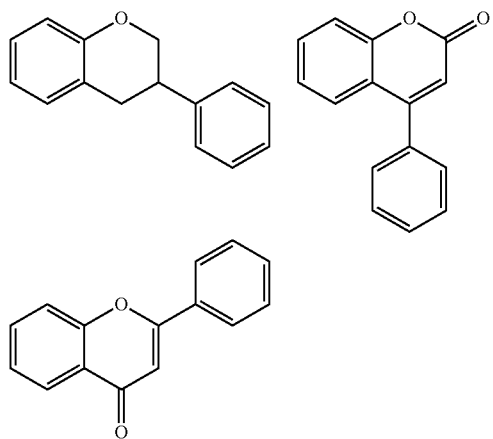

Flavonoids comprise approximately 5,000 naturally occurring compounds. A multitude of other substitutions can be created synthetically, giving rise to the many types of flavonoids.

Many flavonoids are practically insoluble in water and almost all solvents suitable for pharmaceutical, nutraceutical (fortified foods and dietary supplements), cosmeceutical and medical food applications. Thus, there is a need for methods for enhancing the solubility and bioavailability of these flavonoids including flavones and other planar ring structured organic compounds by utilizing acceptable ingredients and methods.

Solubilization of Active Agents

An active agent is the substance in a composition that is biologically active. Solubility is one of the important parameters to achieve a desired concentration of an active agent in solution for a pharmacological response to be elicited. Solubility plays an essential role in drug disposition, since it is only that drug in solution that is able to diffuse through a biological matrix or passively transport across a biological membrane. The maximum rate for drug absorption is a product of permeability and solubility. Drug efficacy can be severely limited by poor aqueous solubility. It is commonly recognized in the pharmaceutical industry that on average more than 40% of newly discovered drug candidates are poorly water-soluble. Poor solubility properties of drugs leads to ineffective absorption from the site of administration; which has been designated as an important part of the high clinical failure due to poor pharmacokinetics (Liu, R., *Introduction, In: Liu, R., (Ed.), Water-Insoluble Drug Formulation*, $2^{nd}$ ed., 2008, CRS press, New York).

There are many techniques that have been used to enhance the solubility of active agents. They include the use of complexing ligands such as cyclodextrins which increase the aqueous solubility of poorly soluble active agents by encapsulating them into the hydrophobic bucket shaped cavity of the cyclodextrin molecule; the nano-sizing of active agents to nano-sized crystals; the use of active agent salt forms (which tend to exhibit improved aqueous solubility and dissolution properties in comparison to the original active agent); and the alteration of the active agents pH microenvironment; etc.

When formulating topical drug products, the active pharmaceutical ingredient is typically added to solvent or solvent mixture to dissolve or disperse the ingredient with mixing or homogenation. Heat, typically in the range of 35° C. to 70° C., has been used to melt low melting point excipients of the formulation to aid in mixing. Heat is kept to a minimum to prevent decomposition, separation upon reaching the cloud point, or loss due to evaporation of any of the excipients or active ingredient.

When forming an emulsion, the active agent is added to either the aqueous or lipid phase of the formulation (generally that phase with the highest solubility for the active agent). One or both phases can be heated in the same range of temperatures noted above either prior to or during mixing of the two phases to make the emulsion.

Dimethyl sulfoxide (DMSO) has been widely used in both in vitro and in vivo studies as a solvent for many water insoluble compounds including apigenin. However, due to toxicity and "taste" concerns, dimethyl sulfoxide is not widely used as a solvent when a topical formulation is considered for human applications. Nearly all apigenin animal studies devoted to anti-skin cancer topical treatments have utilized dimethyl sulfoxide (DMSO) as the solvent of choice due to apigenin's poor solubility in water (<0.005 milligram per milliliter (mg/ml)) and other aqueous solvents. (Li et al, *Evaluation of Apigenin and [G-$^3$H], Apigenin and analytical method development, J. of Pharmaceutical Sciences*. Vol. 86, No. 6, June 1997).

Skin Cancer

The development of skin cancer is a major global public health threat. Ultraviolet (UV), e.g., solar ultraviolet B (UVB) and solar ultraviolet (UVA), radiation are the main causes of skin cancer. The incidences of basal cell carcinoma, squamous cell carcinoma, and melanoma continue to rise despite the advent and use of sunscreen agents with high SPF constituents. Early detection and treatment are essential in improving survival rates, yet skin cancer is a cancer that is largely preventable altogether. Current sunscreen formulations have proven inadequate for fully protecting persons from the DNA-damaging effects of UV radiation. Sunscreen usage may sometimes create a false sense of safety as individuals may over expose themselves to sunlight.

Studies have demonstrated that flavones possess anti-oxidant, anti-mutagenic, anti-carcinogenic, anti-inflammatory, anti-proliferative, and anti-progression properties. (Patel, D, et al., *Apigenin and cancer chemoprevention: Progress, potential, and promise, Intl. J. Oncology* 2007 January; 30(1): 233-45.) In addition, Birt and coworkers used an in vivo mouse model to demonstrate that topical application of apigenin prior to UVB-irradiation significantly reduced, by up to 90%, the incidence of skin cancer. (Birt et al., Anti-mutagenesis and anti-promotion by apigenin, robinetin and indole-3-carbinol, Carcinogenesis, June 1986; 7: 959-963) Other groups have demonstrated apigenin's ability to protect mice against colon cancer. (Wang et al, *Cell cycle arrest at G2/M and growth inhibition by apigenin in human cell colon carcinoma cell lines, Molecular Carcinogenesis*, 28: 102-110 (2000))

Loss of G1/S and/or G2/M cell cycle checkpoint controls leads to transformation and cancer progression. Initiation and progression through the cell cycle is largely controlled by proto-oncogenes that promote cell proliferation and tumor suppressor genes that function to slow or halt cell growth. Mutations in either proto-oncogenes and/or tumor suppressor genes predispose cells to a compromised G1/S checkpoint by shortening the length of time spent in G1 or G2/M.

Researchers have found that apigenin induces reversible, cell-cycle arrests at G1 and G2/M phase of the cell cycle. It was further discovered that apigenin mediates an inhibition on the cell cycle through multiple mechanisms including direct and indirect inhibition of the mitotic kinase p34cdc2, as well as the induction of the cell cycle inhibitor p21WAF1 in a p53-dependent manner. Theoretically, the net effect allows UV induced DNA mutations to be repaired properly prior to cell division. (Lepley D M, et al., *The chemopreventative flavonoid apigenin induces G2/M arrest in keratinocytes, Carcinogenesis,* 17, 2367-75 (1996))

Other Skin Disorders

Kang, Ecklund, Liu & Datta, (*Arthritis Research & Therapy* 2009, Vol. 11) taught that increasing the bioavailability of dietary plant-derived COX-2 and NF-κB inhibitors, such as apigenin, could be valuable for suppressing inflammation in lupus and other Th17-mediated diseases like psoriasis. Apigenin, a non-mutagenic dietary flavonoid, suppresses lupus by inhibiting autoantigen presentation for expansion of autoreactive Th1 and Th17 cells.

Other Diseases

As is typical for phenolic compounds, flavonoids act as potent antioxidants and metal chelators. They also have long been recognized to possess antiinflammatory, antiallergic, hepatoprotective, antithrombotic, antiviral, and anticarcinogenic activities.

The flavones and catechins are very powerful flavonoids for protecting the body against reactive oxygen species (ROS). Body cells and tissues are continuously threatened by the damage caused by free radicals and ROS which are produced during normal oxygen metabolism or are induced by exogeneous damage. The anti-inflammatory activity of flavonoids in many animal models has been reported. Flavones/flavonols such as apigenin, luteolin, kaempferol, quercetin, myricetin, fisetin were reported to possess Lipoxygenase (LO) and Cyclo-oxygenase (COX) inhibitory activities. Jachak S M *Natural products: Potential source of COX inhibitors. CRIPS* 2001; 2(1):12-15.

PCT/US2006/020905 to Doseff discloses methods of treating inflammation with apigenin or its derivatives.

US Patent application US 2008/0227829 to Hammerstone discloses methods of treating subjects with a neurogenic compound including apigenin.

U.S. Patent application US 2007/0154540 to Park et al discloses the use of apigenin as a chondroregenerative agent for the treatment of osteoarthritis.

U.S. Patent application US 2007/0189680 to Bing-Hua et al discloses the use of apigenin for chemoprevention and chemotherapy combined with therapeutic reagents.

U.S. Patent application US 2006/0067905 to Lintnera et al discloses the use of apigenin as a vasodilatory agent for treating baldness.

Research studies have provided evidence that apigenin plays a critical role in the amelioration of the pathogenetic process of asthma. Recent epidemiological studies reported that a low incidence of asthma was significantly observed in a population with a high intake of flavonoids.

Hyaluronic Acid

Hyaluronic acid (HA) is an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the millions. One of the chief components of the extracellular matrix, HA contributes significantly to cell proliferation and migration.

Polysaccharides such as HA are relatively complex carbohydrates. Polysaccharides are polymers made up of many monosaccharides joined together by glycosidic bonds. The polysaccharides are therefore large, often branched, macromolecules. Polysaccharides have been useful in cosmetic and medical applications. For example, HA finds use as a structure stabilizing filler for dermal applications. Apigenin has antihyaluronidase activity; thereby inhibiting the breakdown of hyaluronic acid. (Kuppusamy et al., *Structure-activity studies of flavonoids as inhibitors of hyaluronoidase, Biochem Pharmacol,* 40, 397-401 (1990).

U.S. Patent application 2005/0271692 to Gervasio-Nugent et al discloses topical cosmetic compositions which include flavonoids and hyaluronic acid.

U.S. Patent application 2006/021625 to Morariu discloses topical formulation and methods of use for improving the appearance of aged skin. Preferred components include flavonoids such as apigenin and hyaluronic acid.

Polysorbate Surfactants

Polysorbates (commercially also known as Tweens) are nonionic surfactants and emulsifiers derived from polyethoxylated sorbitan and fatty acids. They are often used in foods and in cosmetics to solubilize essential oils into water-based products. The polysorbates are viscous, water-soluble pale yellow liquids. Polysorbates also help to form emulsions by reducing the surface tension of the substances to be emulsified. Polysorbates have been recognized for their ability to help ingredients to dissolve in a solvent in which they would not normally dissolve. Polysorbates function to disperse oil in water as opposed to water in oil. Polysorbates are produced by reacting the polyol, sorbitol, with ethylene oxide. The polyoxyethylenated sorbitan is then reacted with fatty acids obtained from vegetable fats and oils such as stearic acid, lauric acid, and oleic acid. Surfactants that are esters of plain (non-PEG-ylated) sorbitan with fatty acids are usually referred to by the name Span.

U.S. Pat. No. 7,329,797 to Gupta discloses antiaging cosmetic delivery systems which includes the use of flavonoids including apigenin as an anti inflammatory agent and polysorbate surfactants as emulsifying agents, U.S. Patent Application 2006/0229262 to Higuchi et al disclose pharmaceutical compositions for the treatment of infections for treatment of infections with a drug resistant bacteria infections with agents including flavonoids such as apigenin as an active ingredient and polysorbates as emulsifying agents.

U.S. Pat. No. 6,048,566 to Behnam discloses non-alcoholic beverages and processes of making them. The patent discloses mixing ubiquinone Q10 and a polysorbate solubilizer.

Polyethylene Glycols

Poly(ethylene glycol) (PEG), otherwise known as poly (oxyethylene) or poly(ethylene oxide) (PEO), is a synthetic polyether that is readily available in a range of molecular weights (MW). Materials with MW<100,000 are usually called PEGs, while higher molecular weight polymers are classified as PEOs. These polymers are amphiphilic and soluble in water as well as in many organic solvents. Low molecular weight (MW<1,000) PEGs are viscous and colorless liquids, while higher molecular weight PEGs are waxy, white solids with melting points proportional to their molecular weights to an upper limit of about 67° C. PEG has been found to be nontoxic and is approved by the FDA for use as a surfactant or as a carrier in different pharmaceutical formulations, foods, and cosmetics. Most PEGs with MW>1,000 are rapidly removed from the body unaltered with clearance rates inversely proportional to polymer molecular weight. This property, combined with the availability of PEGs with a wide range of end-functions, contributes to the wide use of PEGs in biomedical research: drug delivery, tissue engineering scaffolds, surface functionalization, and many other applications.

In view of the foregoing, it is most desirable to improve the solubility of poorly soluble compounds including flavonoids. It is also desirable to incorporate flavonoids, such as the flavones apigenin and luteolin, as part of topical formulations to aid in the prevention and/or treatment of skin damage or skin cancer resulting from the effects of sun exposure and also to provide a skin treatment composition useful in the treatment of a variety of dermatological conditions.

SUMMARY OF THE INVENTION

The subject invention relates to a composition comprising i) a planar ring structured organic compound, and ii) a heat stable solubilizing compound, wherein the concentration of the planar ring structured organic compound is greater than the saturation concentration of the planar ring structured organic compound in said heat stable solubilizing compound, and said composition is not supersaturated. The heat stable solubilizing compound is typically a nonionic surfactant such as a polysorbate. The composition also typically includes a carrier.

The subject invention relates to compositions comprising a planar ring structured organic compound, such as a flavonoid, and a heat stable solubilizing compound such as a surfactant, wherein the composition is formed by: mixing the planar ring structured organic compound and the solubilizing compound to an elevated temperature (typically >100° C.) where said planar ring structured organic compound is dissolved in the solubilizing compound. When the dissolved mixture is cooled to ambient temperatures, the planar ring structured organic compound remains dissolved even at concentrations exceeding the ambient temperature saturation concentration level.

The composition optionally includes an alcohol selected from the group consisting of ethanol, small-chain alcohols (such as isopropyl and benzyl alcohol), ethoxydiglycol (diethylene glycol monoethyl ether or Transcutol), propylene glycol, hexylene glycol, butylene glycol, dipropylene glycol, glycerin, water, saline, DMSO, isopropyl myristate, mineral oil, low viscosity surfactants, and dimethyl isosorbide.

In a preferred embodiment, the composition is a pharmaceutical composition and the carrier is a pharmaceutically acceptable carrier. The composition can include hyaluronic acid, and/or a penetration enhancer. In one embodiment the composition is in the form of an emulsion or microemulsion. The composition can be, for example, a pharmaceutical composition, a nutraceutical (fortified foods or a dietary supplement), cosmeceutical, a food supplement, or medical food.

Another embodiment of the invention is a patch for application of a planar ring structured organic compound, such as a flavonoid, transdermally comprising a substrate having two sides, a first side having a composition of the invention and an adhesive (with a release liner), and a second side with a material which is impermeable to the composition and adhesive on the first side. In another embodiment, the patch comprises a substrate having two sides, the first side having a liquid reservoir containing a composition of the invention and a semipermeable membrane and an adhesive layer attached to the underside of the semipermeable membrane (with a release liner) and a second side with a material which is impermeable to the composition and to the adhesive on the first side.

Another embodiment of the invention is a method of preparing a solubilized planar ring structured organic compound, such as a flavonoid composition comprising: mixing a planar ring structured organic compound, such as flavonoid particles, with a heat stable solubilizing compound, such as a surfactant, to form a mixture, heating the mixture to a temperature where the planar ring structured organic compound is solubilized, and cooling the solution. In an advantageous embodiment, the heat stable solubilizing compound is a nonionic surfactant. Typically, the mixture is stirred while heating, and up to 10 wt % of a planar ring structured organic compound, such as a flavonoid compound, is added. In an advantageous embodiment, the surfactant is a polysorbate. After the heating or cooling step is the step of adding the solution to a dermatological, oral, injectable, periodontal, dermal patch, or aerosol carrier. A small chain alcohol selected from the group consisting of ethyl alcohol, isopropyl alcohol, benzyl alcohol, ethoxydiglycol and dimethyl isosorbide, can be added to the solution.

The invention also relates to method of increasing the solubility of a poorly soluble planar ring structured organic compound composition comprising: i) mixing the planar ring structured organic compound with a heat stable solubilizing compound to form a mixture, ii) heating the mixture to a temperature where the planar ring structured organic compound particles are solubilized to form a solution, and iii) cooling the solution.

The invention also relates to a method of reducing and/or preventing the effects of sun exposure comprising applying a therapeutically effective amount of a sunscreen formulation to the skin comprising a solubilized planar ring structured organic compound, such as a flavonoid, and a carrier that permits delivery of the planar ring structured organic compound, such as a flavonoid, to the stratus corneum and the epidermis. In another embodiment, the formulation additionally comprises mineral oxides to provide additional ultraviolet sun exposure protection.

In another embodiment, the invention relates to a method of treating the effects of sun exposure comprising applying a therapeutically effective amount of a formulation to sun damaged skin comprising a solubilized planar ring structured organic compound, such as a flavonoid, and a carrier that permits delivery of the flavonoid to the stratus corneum and the epidermis.

In another embodiment, the invention relates to a method of reducing the likelihood of or treating cancer in a mammal comprising administering to a mammal in need of such treatment a prophylactic amount or a therapeutically effective amount of a formulation of the invention.

In another embodiment, the invention relates to a method of treating inflammation in a mammal comprising administering to a mammal in need of such treatment a therapeutically effective amount of a formulation of the invention.

In another embodiment, the invention relates to a method of restoring normal skin barrier function in a mammal comprising administering to a mammal in need of such treatment a therapeutically effective amount of a formulation of the invention such as a flavonoid formulation.

In another embodiment, the invention relates to a method of treating a skin disease or disorder such as acne, alopecia, dermal sensitization and irritation, dry skin (xerosis, ichthyosis), fungal infections, and rosacea, contact dermatosis, in a mammal comprising administering to a mammal in need of such treatment a therapeutically effective amount of a formulation of the invention.

In another embodiment, the invention relates to a method of treating autoimmune disease such as psoriasis, lupus, and arthritis in a mammal comprising administering to a mammal in need of such treatment a therapeutically effective amount of a formulation of the invention.

In another embodiment, the invention relates to a method of treating allergies, asthma, atopic dermatitis/eczema comprising administering to a mammal in need of such treatment a therapeutically effective amount of a formulation of the invention.

In another embodiment, the invention relates to a method of treating or reducing the likelihood of a TNFα related disease in a mammal comprising administering to a mammal in need of such treatment a therapeutically effective amount or a prophylactic amount of a flavonoid formulation of the invention.

In another embodiment, the invention relates to a method of treating or reducing the likelihood of an IL-113 related disease in a mammal comprising administering to a mammal in need of such treatment a therapeutically effective amount or a prophylactic amount of a flavonoid formulation of the invention.

DESCRIPTION OF THE DRAWINGS

FIG. 1 shows surfactant classification according to their head: nonionic, anionic, cationic and amphoteric.

FIG. 2 is a mass spectroscopy plot indicating insignificant chemical composition differences between the unprocessed polysorbate 80 control sample and the thermally treated polysorbate 80 sample.

FIG. 3 is a graphical plot illustrating the apigenin content deposited within the epidermal, dermal and receptor fluid segments of human tissues for several applied topical formulations containing various apigenin concentrations.

DETAILED DESCRIPTION OF THE INVENTION

The subject invention relates to new formulations of planar ring structured organic compounds, such as a flavonoids. Included are pharmaceutical compositions, nutraceuticals, cosmeceuticals, food supplements, and medical foods, containing such formulations, as well as methods for making and using the same.

Solubility is an important parameter for the topical and oral bioavailability of poorly soluble planar ring structured organic compound, such as a flavonoid. Dissolution of a drug can be the rate determining step of a poorly water soluble drug for oral absorption and topical absorption. Drug solubility is also the basic requirement for the formulation and development of different dosage forms where the drug is intended to be in solution. Because of solubility problems associated with many planar ring structured organic compounds, such as a flavonoids, their bioavailability is limited and hence solubility enhancement becomes necessary. The methods of making and using novel soluble forms of poorly soluble planar ring structured organic compounds taught in this disclosure, address the enhancement of poorly soluble ring structured organic compounds.

The subject invention relates to adding a planar ring structured organic compound, such as a flavonoid, to a heat stable surfactant and then heating the mixture up to an elevated temperature (typically >100 degrees C.), not exceeding the boiling point or decomposition point of either the active agent (e.g. flavonoid) or the heat stable solubilizing agent (e.g. surfactant), and then cooling the mixture. It was unexpectedly observed that this process can enhance dissolution, and a significantly higher concentration of the planar ring structured organic compound in solution with the surfactant can be achieved. Furthermore, the resulting solution "concentrate" is not supersaturated. The molar ratio of active agent to solubilizing agent is typically 1:2 to 1:5, and at times much greater, e.g. 1:2 to 1:20 depending on the active agent/surfactant combination. While not wishing to be bound by theory, it is believed that the heat necessary to facilitate dissolution is needed to overcome the bonds associated with self-associated stacking of the planar ring structured organic compounds—which limits their solubility. Upon dissolution of these planar ring structured organic compounds with heat in the heat stable solubilizing agent, the solubilizing molecules coat or sandwich these planar compounds—ie the heat stable solubilizing agent and the planar compound "associate" or form a "complex." Upon cooling to room temperature, the concentrates are not supersaturated solutions even though the concentrations of the compounds are greater than their saturation concentration at ambient conditions—room temperature (temperature below that necessary to overcome the planar ring structured organic compound self-associated stacking forces). The concentrate is stable and the compounds (or active agents) stay in solution for periods of time sufficient for making formulations from the concentrates.

These planar ring structured organic compound concentrates can be used to formulate compositions with a higher concentration of the compounds in solution than that achievable without the use of the concentrates. That is, these concentrates can be used to prepare formulations that have the planar ring structured organic compounds at a higher concentration in solution than that achievable by a) use of standard formulation preparation techniques, or b) mixing of the planar ring structured organic compounds with a surfactant and excipients all together, and then heating to an elevated temperature.

I—Compounds of the Invention

The present invention relates to molecules that are planar with at least one ring structure that allow for a stacking arrangement. The ring structure can be an aromatic structure. Those molecules that do stack characteristically have a high melting point and demonstrate poor solubility. It is the poor solubility characteristics that typically limit practically for use of these compounds in topical products and drug formulations. As used herein, the term "poor solubility" means having a solubility in water or oil less than 1 mg/ml, and particularly less than 0.1 mg/ml.

Examples of planar ring structured organic compounds with poor solubility include the following important classes of active agents:

Class 1. The camptothecin analogs are used as antineoplastic agents and are sparingly soluble in water. The methods of the present invention can be applied to solubilize these agents. Included are camptothecin, topotecan and irinotecan and compounds with other substitutions for R10, R9 and R7

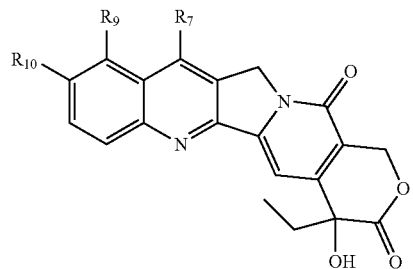

| | R10 | R9 | R7 |
|---|---|---|---|
| Camptothecin | H | H | H |
| Topotecan | OH | (CH₃)₂NHCH₂⁻ | H |
| Irinotecan | 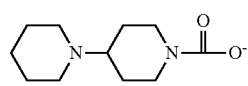 | H | CH₃CH₂⁻ |

Class 2. The guanidine nucleosides used as antivirals and in particular antiherpes treatments. Such agents have limited water solubility. Included are acyclovir, penciclovir, ganciclovir, and compounds with other substitutions for R1.

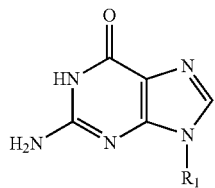

Acyclovir R1 = CH₂OCH₂CH₂OH
Penciclovir R1 = CH₂CH₂CH(CH₂OH)₂
Ganciclovir R1 = CH₂KCH(CH₂OH)₂

Class 3. The benzodiazepines are CNS active drugs for depression and anxiety. These tricyclic agents are sparingly soluble in water and can be solubilized using the methods of the invention. Such compounds include alprazolam, oxazepam, and all related agents of the general formula.

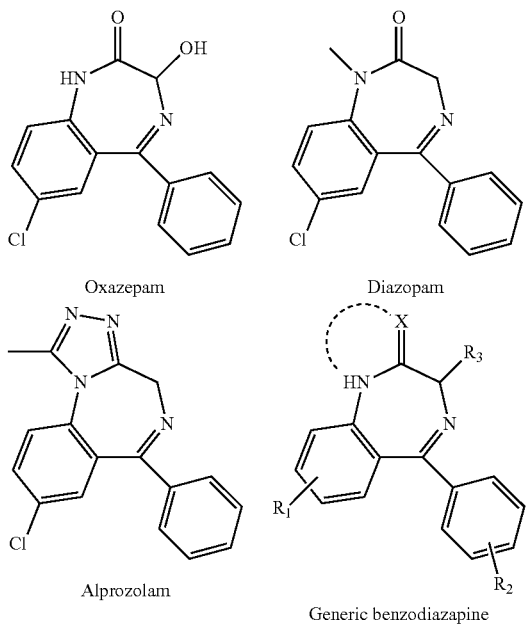

Class 4. The tertiary anime tricyclic antidepressants can be made soluble with treatment with mineral acids and as acid salts. The methods of this invention solubilize these agents without the use of acids. Such compounds include amitriptyline, clomipramine, doxepin and all related compounds such as maprotiline and protriptyline

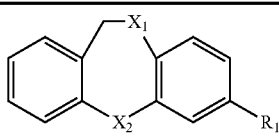

| | R1 | X1 | X2 |
|---|---|---|---|
| Amitriptyline | H | CH₂ | C=CCH₂CH₂N(CH₃)₂ |
| Clomipramine | Cl | CH₂ | NCH₂CH₂CH₂N(CH₃)₂ |
| Doxepin | H | O | C=CCH₂CH₂N(CH₃)₂ |

Class 5. The tricyclic phenothiazines are used as antipsychotics and can be solubilized by the methods of the invention without the use of strong acids. Such compounds include chlorpromazine, chlorprothixene and related tricyclics

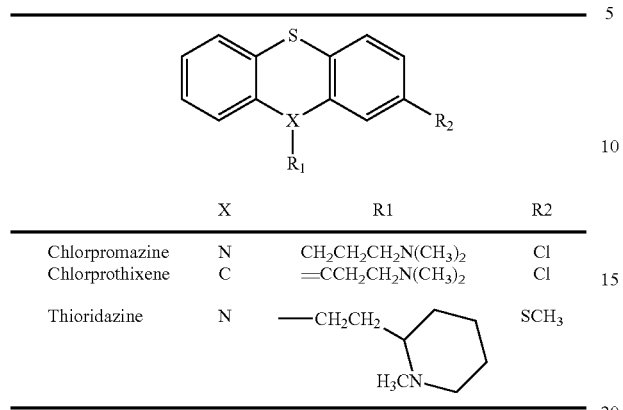

Class 6. The tricyclic iminostilbenes are used as anticonvulsants and can be solubilized by the methods of the invention. Such compounds are carbamazepine, oxcabazepine and all related tricyclic iminostilbenes.

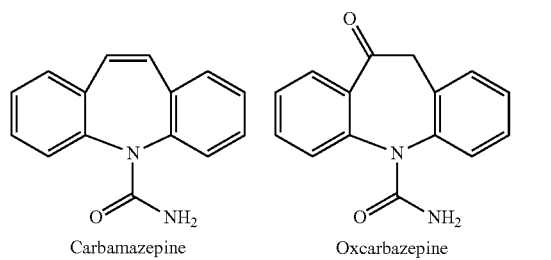

Class 7. The method of the present invention can also be applied to nonfused ring systems. Such compounds include dilantin and the dicarbamates, felbamate and levetiracetam which are all very water insoluble anti-seizure medications. Other related compounds are also included.

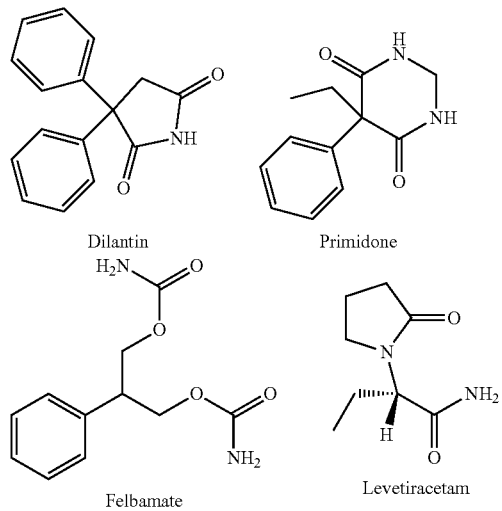

Class 8. Many of the dihydrofolic acids analogs are sparingly soluble in water. The method of the present invention can be applied to this class of agents including methotrexate and trimetrxate which are used for psoriasis and autoimmune diseases. Related compounds are included.

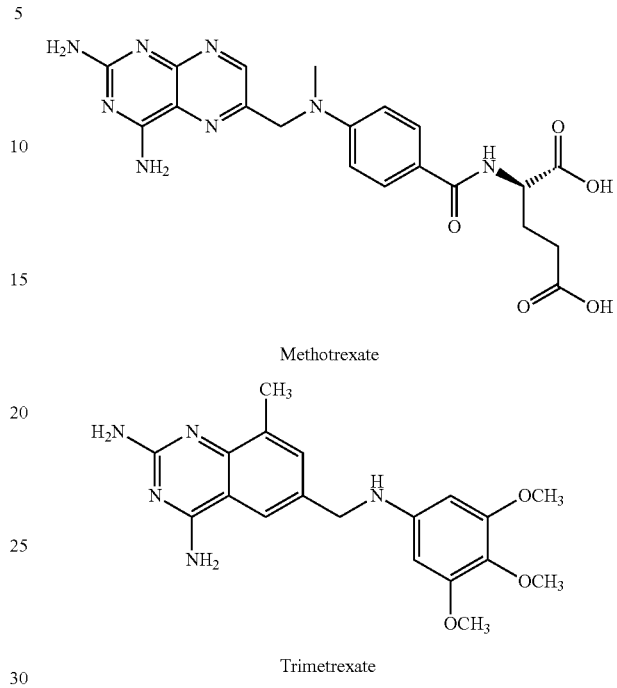

Class 9. The sulfa antibacterials can be solubilized by the methods of the present invention. Such compounds include sulfamethoxazole, sulfadoxine and all related sulfa antibacterial compounds.

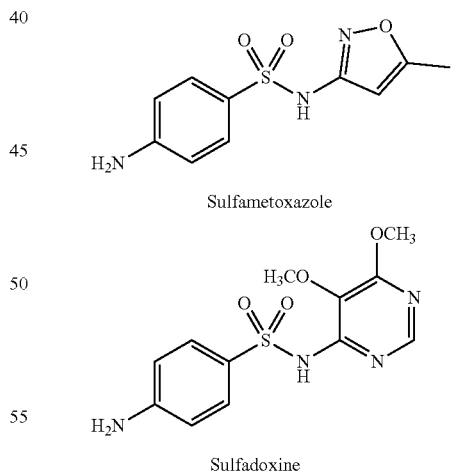

Class 10. Several sulfa drugs are also carbonic anhydrase inhibitors and are useful for the treatment of glaucoma, ulcers, and as diuretics. These compounds have poor water solubility and can be solubilized by the methods of the present invention. Such compounds include ethoxzolamide, acetazolamide, and the anticonvulsant sultiam.

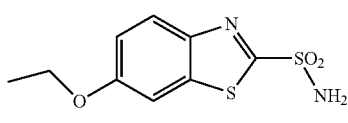

Ethoxzolamide

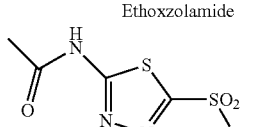

Acetazolamide

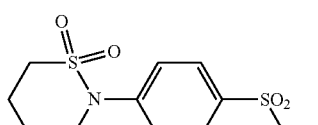

Sultiame

Class 11. The anthracycline anticancer agents are tetracyclines with poor water solubility. Such compounds include doxorubicin (adriamycin), daunorubicin, epirubicin, idarubicin, and all related compounds.

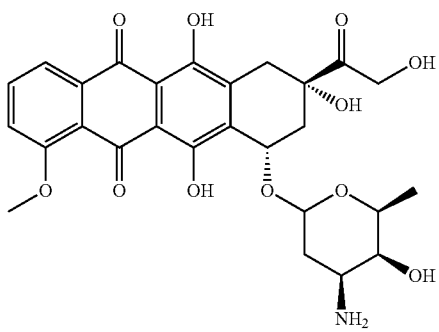

Doxorubicin

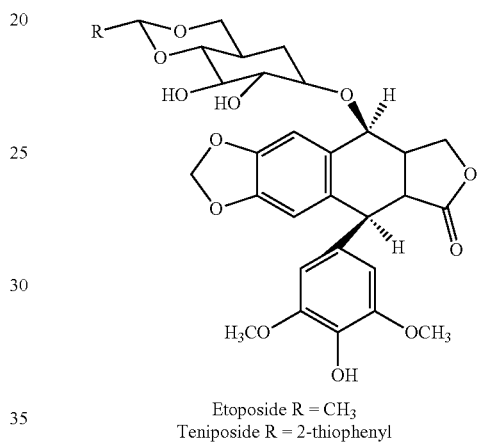

Generic anthracycline

Class 12. The epipodophyllotoxins are useful and anticancer agents. The methods of the present invention can be used to solublize compounds in this class. Such agents include etoposide, teniposide and all related compounds.

Etoposide R = $CH_3$
Teniposide R = 2-thiophenyl

Class 13. Certain of the pyrimidine nucleoside analogs are poorly soluble in water and are useful as antineoplastic agents, for psoriasis, or to inhibit the growth of DNA viruses.

Compounds in this class are 5-fluorouracil (5-FU), floxuridine, gemcitabine, zidovudine, stavudine, and all related compounds.

| | R1 | R2 | | R1 | R2 |
|---|---|---|---|---|---|
| Floxuridine | 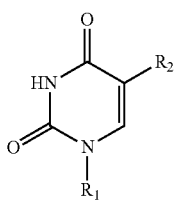 | F | Gemcitibine | 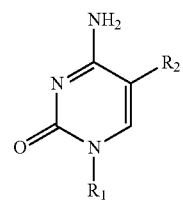 | H |

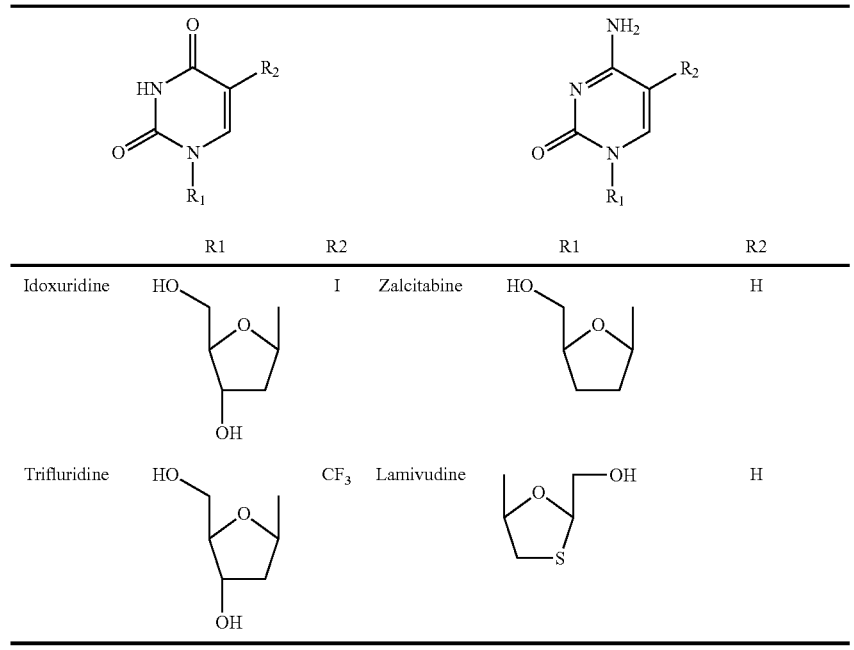

| | R1 | R2 | | R1 | R2 |
|---|---|---|---|---|---|
| Idoxuridine | HO-[sugar]-OH | I | Zalcitabine | HO-[sugar]-OH | H |
| Trifluridine | HO-[sugar]-OH | $CF_3$ | Lamivudine | HO-[S-sugar]-OH | H |

Class 14. Similar to the pyrimidine nucleosides, the adenine and guanidine based chemotherapeutics which are useful vs DNA viruses, are also sparingly soluble in water unless combined with strong acids. The method of the present invention can solublize these agents in water without the use of strong acids. Compounds included in this class include didanosine and abacavir and all related compounds.

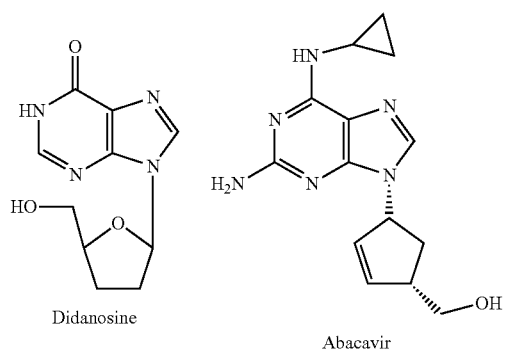

Didanosine

Abacavir

Class 15. Certain selective estrogen receptor modulators have found use as treatments for breast cancer, osteoporosis and contraception. Many of these poly phenyl agents have low solubility in water unless combined with strong acids. The methods of the present invention are useful for increasing the water solubility without the use of acids. Such agents include tamoxifen, clomiphene, lasofoxifene and all related agents.

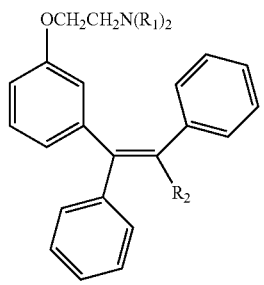

Tamoxifen R1 = Me; R2 = Et
Clomiphene R1 = Et; R2 = Cl

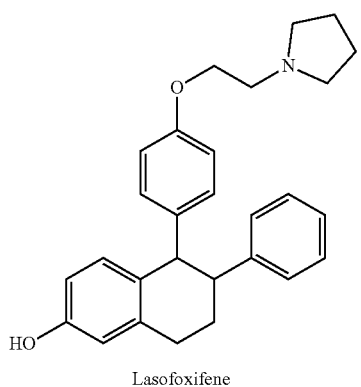

Lasofoxifene

Class 16. Still other selective estrogen receptor modulators belong to another structural class. One such agent is raloxifene which is useful for treating osteoporosis and other estrogen related diseases. In the absence of strong acids or very low PH raloxifene is sparingly soluble in water. The methods of the present invention can increase the solubility of this and related agents.

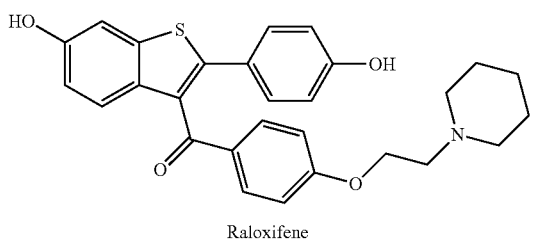 [SMILES: O=C(c1ccc(OCCN2CCCCC2)cc1)c1c(-c2ccc(O)cc2)sc2cc(O)ccc12]

Raloxifene

Class 17. The progesterones are a class of steroidal hormones and agents affecting the female reproduction cycle. Such agents include megesterol acetate and medroxyprogesterone and all related agents and are used in many areas of human and animal health. All the compounds in this class are sparingly soluble in water. Solubility in water can be improved by application of the methods of the present invention.

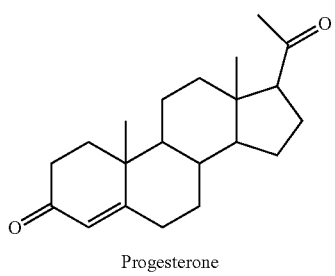

Progesterone

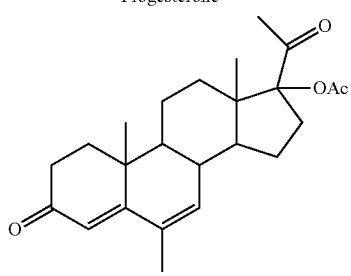

Megesterol Acetate

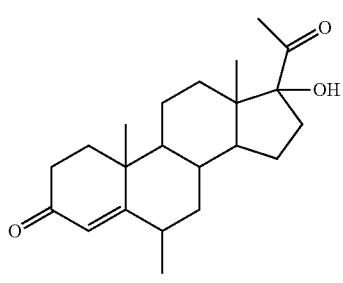

Medroxyprogesterone

Class 18. The estrogens are a class of steroid hormones that affect the female reproductive cycle, development, and maturation. Such compounds include estradiol, estradiol valerate, mestranol, estrone and all related analogs. All of the compounds in this class are sparingly soluble in water. Solubility can be improved by application of the methods of the present invention.

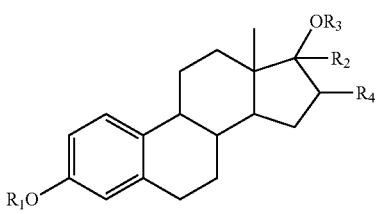

| | R1 | R2 | R3 | R4 |
|---|---|---|---|---|
| Estradiol | H | H | H | H |
| Estradiol Valerate | H | H | $CO(CH_2)_3CH_3$ | H |
| Estriol | H | H | H | OH |
| Mestranol | $CH_3$ | C≡CH | H | H |

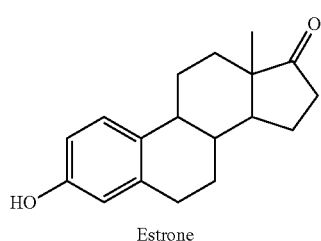 [SMILES: CC12CCC3c4ccc(O)cc4CCC3C1CCC2=O]

Estrone

Class 19. The testosterones and the nortestosterones are steroid hormones affecting the reproductive cycle in humans and which also affect growth, development and maturation and related processes. The anabolic steroids also belong to this class. Such agents include methyltestosterone, oxandrolone, danazol and a many related compounds within the class. Like most of the steroids, these compounds are sparingly soluble in water and may be solubilized by the methods of the present invention.

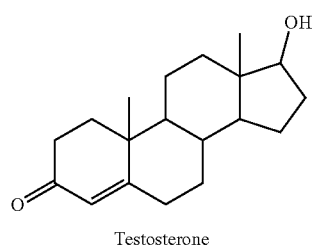

Testosterone

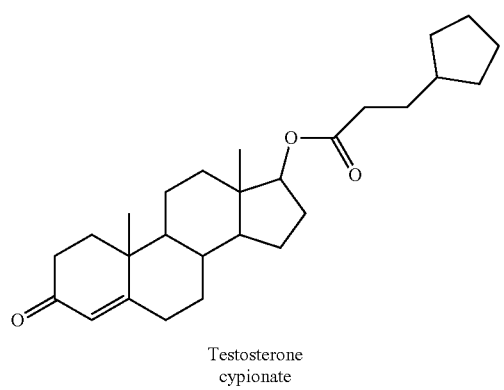

Testosterone cypionate

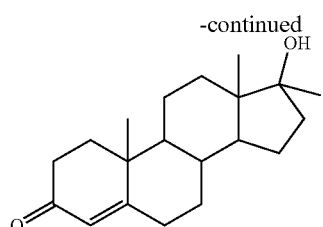

Methyltestosterone

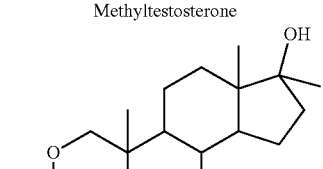

Oxandrolone

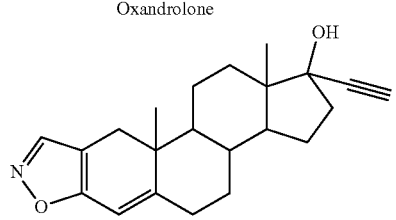

Danazol

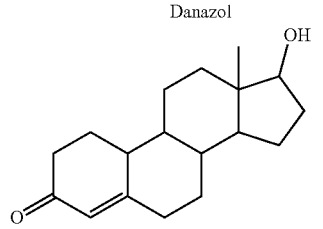

Nortestosterone

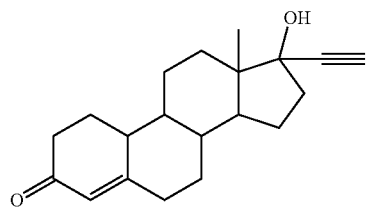

Norethindrone

Class 20. The corticosteroids are useful for the treatment of inflammation, carbohydrate and lipid metabolic syndromes and for other disease states. Such compounds include hydrocortisone, fludrocortisone, dexamethasone and all related agents. These corticosteroids are sparingly soluble in water but can be made more soluble by application of the methods of the present invention.

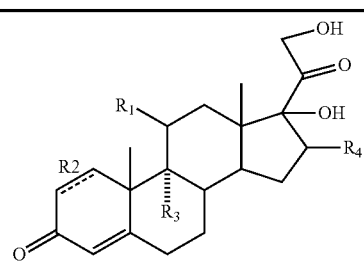

|  | R1 | R2 | R3 | R4 |
|---|---|---|---|---|
| Hydrocortisone | OH | Single Bond | H | H |
| Fludrocortisone | OH | Single Bond | F | H |
| Dexamethasone | OH | Double Bond | F | CH$_3$ |
| Cortisone | C=O | Single Bond | H | H |

Class 21. The glitizones are a class of compounds used to treat hyperglycemia and insulin resistance. Such compounds include rosiglitazone, pioglitazone, troglitizone and all related analogs. These compounds are only sparingly soluble in water, but the solubility can be improved by application of the methods of the present invention.

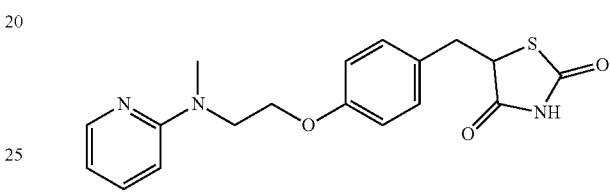

Rosiglitazone

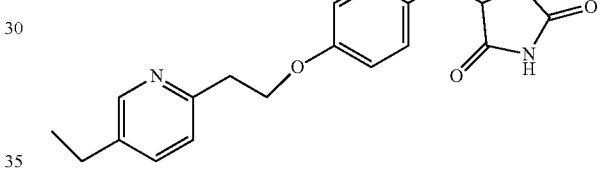

Pioglitazone

Class 22. The quinone class of agents which include atovaquone, buparvaquone and parvaquone are useful as antiprotozoal drugs. These agents and all of their analogs tend to be sparingly soluble in water. They can be solubilized by application of the methods of the present invention.

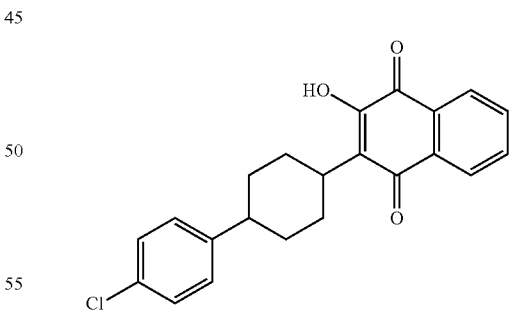

Atovaquone

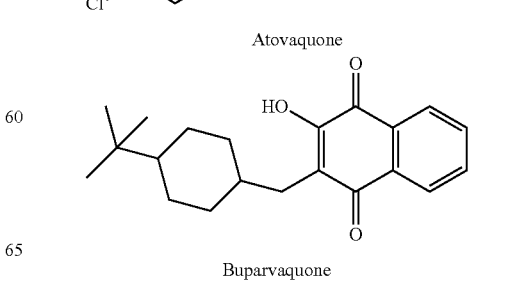

Buparvaquone

-continued

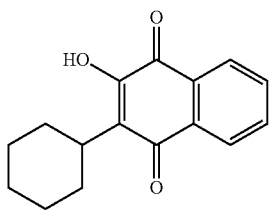

parvaquone

Class 23. The quinoline class of agents which include mefloquine, primaquine, cloroquine and all related analogs are useful as antimalarials. These agents are soluble in strong acid or as their acid salts. The methods of the present invention can solublize these agents in water without the use of strong acids.

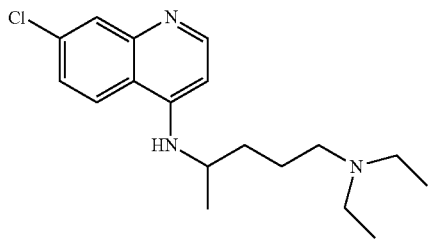

Chloroquine

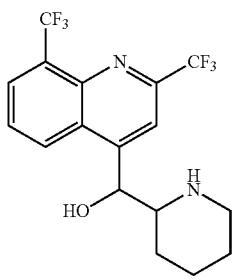

Mefloquine

Class 24. Piroxicam and meloxicam and their related analogs are useful to treat pain, swelling, and other related symptoms. These agents are sparingly soluble in water. These agents and all related analogs can be solubilized by application of the present invention.

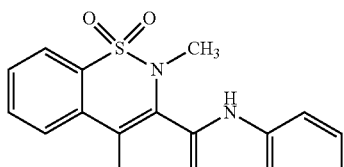

Piroxicam

-continued

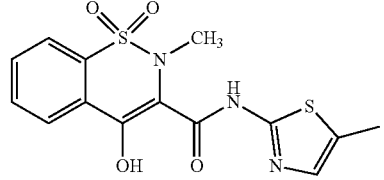

Meloxicam

Class 25. The propionates are a class of agents useful for treating pain, fever, and inflammation. Members of this class include ibuprofen, naproxen, fenoprofen, nabumetone and many related analogs. These compounds are weak acids and are sparingly soluble in water. They may be soluble in strong alkali and high pH. The methods of the present invention solublize these agents without the need for strong alkali or high pH

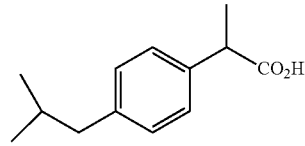

Ibuprofen

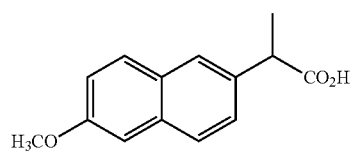

Naproxen

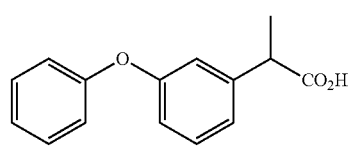

Fenoprofen

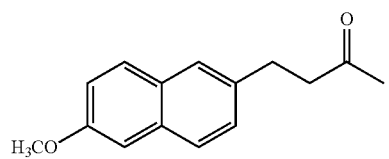

Nabumtone

Class 26. Multi-ring anti-inflammatory agents such as indomethacin, sulindac and all of their analogs are sparingly soluble in water without the addition of strong alkali or high pH. Using the methods of the present invention, these agents can be solubilized without the use of alkali or high pH.

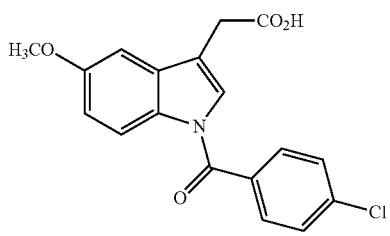
Indomethacin

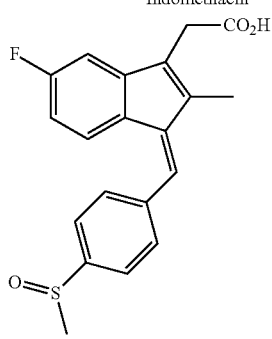
Sulindac

Class 27. The indole based antiemetics which include ondansetron, dolasetron, granisetron, and all their related analogs are 5-HT3 receptor antagonists. These agents tend to be sparingly soluble in water. They and their related analogs can be solubilized by application of the methods of the present invention.

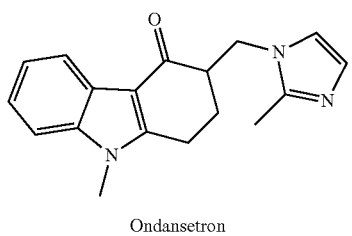
Ondansetron

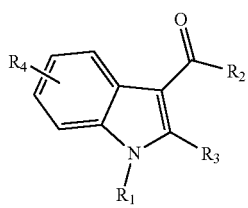
Generic structure
R1-4 are substituents
found in this class of agents Class 28. The azole antifungals are an important therapeutic class of agents including clotrimazole, miconazole, sulconazole, ketoconazole and all of their related anaologs. These agents tend to be sparingly soluble in water. They can be solubilized by application of the methods of the present invention.

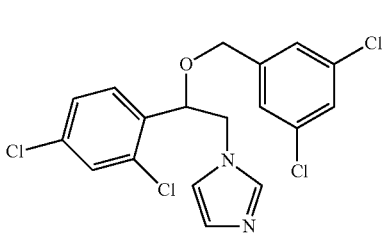
Miconazole

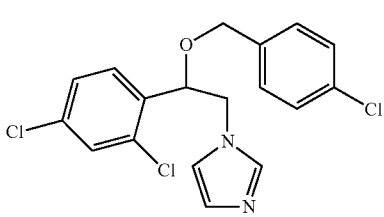
Sulconazole

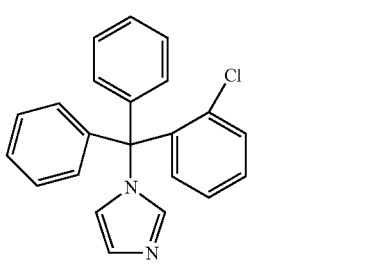
Clotrimazole

Class 29. The benzimidazoles omeprazole, lasoprazole, and of the related analogs have utility as proton pump inhibitors. These agents are sparingly soluble in water but can be solubilized by application of the methods of the present invention.

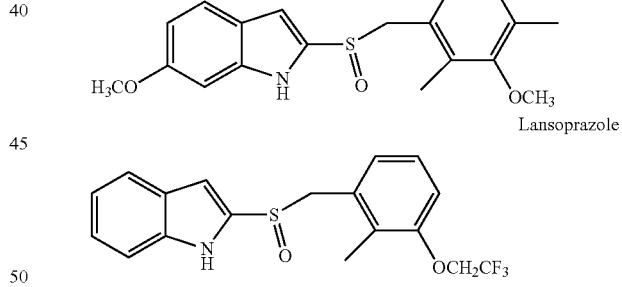
Omeprazole

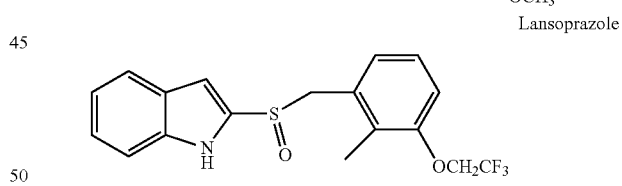
Lansoprazole

Class 30. Compounds with various aromatic rings lacking sites for solubilization with strong acids or strong alkali can be solubilized by application of the methods of the present invention. Examples of such agents that can be solubilized are:

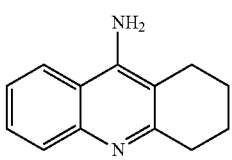
Tacrine
Alzheimer's

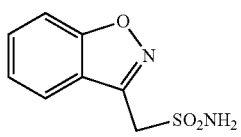

Zonisamide
Siezures

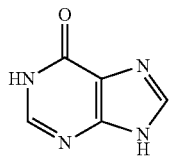

Allopurinal
Gout

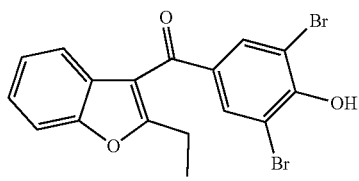

Benzbromozone
Gout

Class 31. Compounds of the quinolone class of antibacterials such as ciprofloxacin, moxifloxacin and ofloxacin are sparingly soluble in water. These compounds have heterocyclic side chains which bear a basic nitrogen, which can form salts with strong acids. The salts increase solubility but even the salts are sometimes less soluble than desired. The methods of the present invention will increase the water solubility of these compounds without the use of strong acids. For cases where there is no basic nitrogen or only weakly basic nitrogens, the methods of the present invention will still solublize these agents. One such example is WCK771. The generic structure describes some of the compounds where the methods would apply.

Ofloxacin

Ciprofloxacin

Moxifloxacin

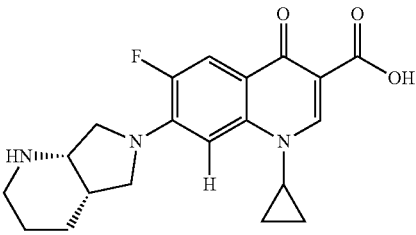

WCK771

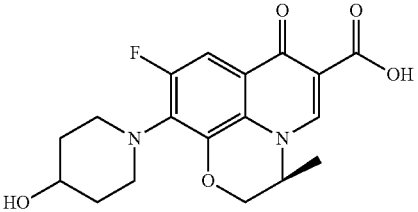

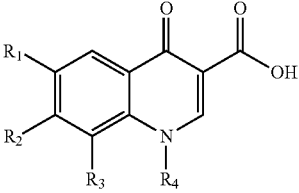

$R_1$ = F or H
$R_2$ = Heterocyclic ring
$R_3$ = O-alkyl, H, alkyl
$R_4$ = cyclopropyl, aryl, ethyl, or $R_3$ and $R_4$ form a ring Class 32. Certain of the compounds which act as local anesthetics such as benzocaine, mepivacaine, lidocaine and related structures are sparingly soluble in water without the addition of strong acids or low pH. Application of the methods of the present invention increase the solubility of such compounds without the use of strong acids or low pH.

Benzocain

Mepivacaine

Lidocaine

Class 33. Capsaicin and its related compounds are useful for treatment of pain or injury. Capsaicin is sparingly soluble in cold water. Application of the methods of the present invention increases the solubility of capsaicin and related compounds.

Capsaicin

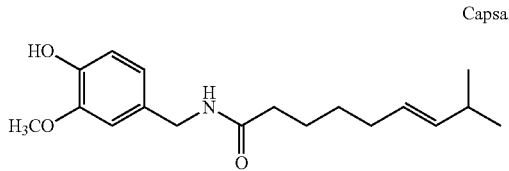

Class 34. The aryl acetic acids such as tolmetin, ketorolac, diclofenac and their related structures are useful as anti-inflammatory agents and for treatment of pain. They are sparingly soluble in water. At higher pH or with treatment with base the solubility is improved. The methods of the present invention increase the solubility of these agents and their analogs in water without the use of base or elevated pH.

Tolmetin

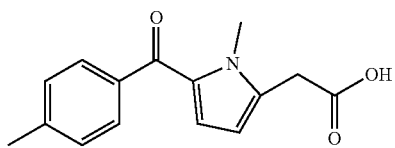

Ketorolac

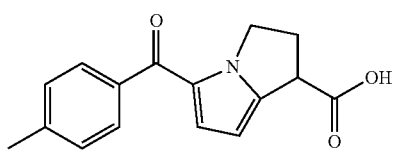

Diclofenac

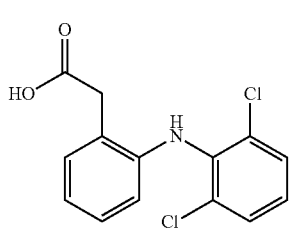

Class 35. Several anti-inflammatory and pain agents belong to a broad class of diphenyl heterocycles such as rofecoxib, celecoxib, sulfinpyrazone, phenylbutazone and related compounds. These compounds are sparingly soluble in water. Application of the methods of the present invention increase the solubility of these and related compounds in water.

Rofecoxib

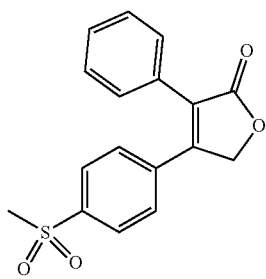

Celecoxib

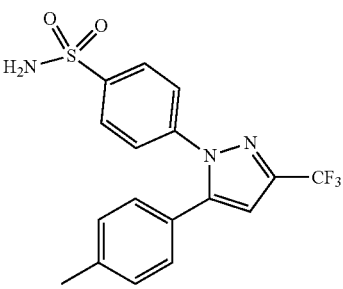

Sulfinpyrazone

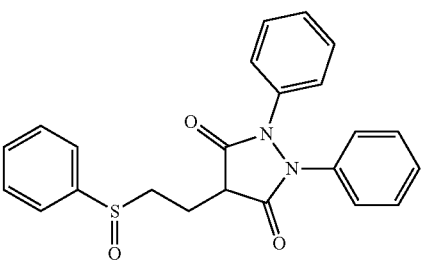

Class 36. The statins are a well known class of agents which are useful to treat hyperlipidemia and related ailments. This class of compounds includes lovastatin, atorvastatin, cerivastatin and all related structures. These compounds are sparingly soluble in water and even several of the acid salts are not freely soluble. Application of the methods of the present invention increases the solubility in water for these and the compounds in this class.

Lovastatin

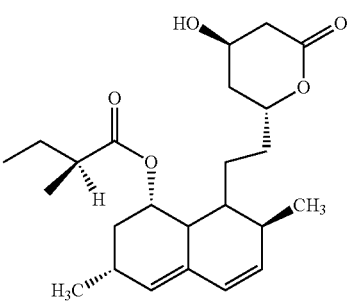

Atorvastatin

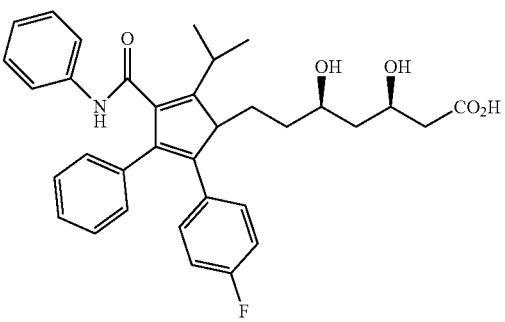

-continued

Cerivastatin

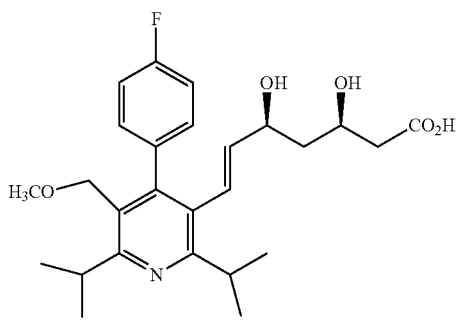

Class 37. Fibrates such as fenofibrate are poorly soluble compounds. Application of the methods of the present invention increase the solubility of these compounds in water.

Below are chemical structures and chemical/physical properties of some other poorly soluble planar ring structured organic compounds:

TABLE I

PROPERTIES OF SOME PLANAR ACTIVE AGENT

| Active Agents | Usage | CAS # | MW | MP-° C. |
|---|---|---|---|---|
| MEFENAMIC ACID | Pain Relief/NSAID | 61-68-7 | 241 | 230 |
| DICLOFENAC SODIUM | Pain Relief/NSAID | 15307-86-5 | 318 | 283 |
| (1)DICLOFENAC ACID | Pain Relief/NSAID | 15307-79-6 | 296 | ~(2)177 |

Note:
(1)Synthesized from Sodium Diclofenac-See Diclofenac Section for details
(2)J Pharmaceut Sci, 6(3): 352-359, 2003

Polyphenols Including Flavonoids

The chemical structures of some commonly occurring plant planar ring structured flavonoids are listed below.

TABLE II

CHEMICAL STRUCTURES OF SOME COMMONLY OCCURING PLANT FLAVONOIDS

| Structure | | Representative flavonoids |
|---|---|---|
| Flavones |  | R1 = H, R2 = OH: Apigenin<br>R1 = R2 = OH: Luteolin |

TABLE II-continued

CHEMICAL STRUCTURES OF SOME COMMONLY OCCURING PLANT FLAVONOIDS

| Structure | | Representative flavonoids |
|---|---|---|
| Flavonols |  | R2 = OH, R1 = R3 = H: Kaempferol<br>R1 = R2 = OH, R3 = H: Quercetin<br>R1 = R2 = R3 = OH: Myricetin |
| Isoflavones | 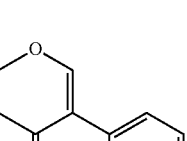 | R1 = H: Daidzein<br>R1 = OH: Genistein |
| Flavanols | 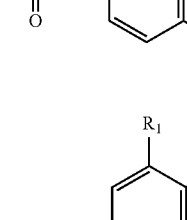 | R1 = R2 = OH, R3 = H: Catechins<br>R1 = R2 = R3 = OH: Gallocatechin |
| Flavanones | 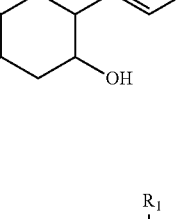 | R1 = H, R2 = OH: Naringenin<br>R1 = R2 = OH: Eriodictyol<br>R1 = OH, R2 = OCH3: Hesperetin |
| Anthrocyanins | 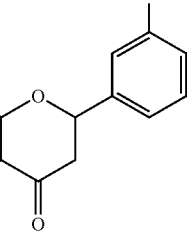 | R1 = H, R2 = H: Pelargonidin<br>R1 = OH, R2 = H: Cyanidin<br>R1 = R2 = OH: Delphinidin<br>R1 = OCH3, R2 = OH: Petunidin<br>R1 = R2 = OCH3: Malvidin |

Flavonoids include the flavones (e.g., apigenin, luteolin), flavonols (e.g., quercetin, myricetin), flavonones (e.g., naringenin, hesperidin), flavonols (or catechins) (e.g., epicatechin, gallocatechin), anthocyanidins (e.g., cyaniding, pelargonidin), and isoflavones (e.g., genistein, daidezin).

Apigenin is a member of the flavone structural class and is chemically known as 4',5,7,-trihydroxyflavone. Apigenin has the following structural formula:

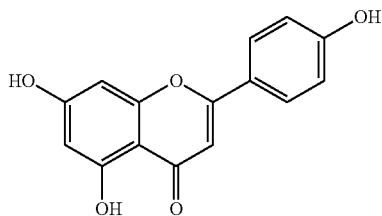 [SMILES: O=c1cc(-c2ccc(O)cc2)oc2cc(O)cc(O)c12]

Luteolin is also a member of the flavone structural class and is chemically known as 3',4',5,7-tetrahydroxyflavone. Luteolin has the following structural formula):

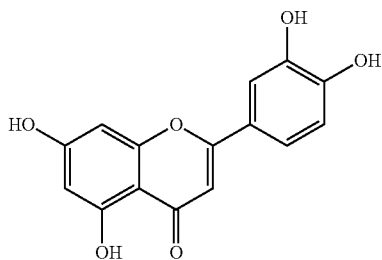 [SMILES: O=c1cc(-c2ccc(O)c(O)c2)oc2cc(O)cc(O)c12]

Both apigenin and luteolin are practically insoluble (i.e., a solubility of less than 1 mg/ml) in water and nearly all solvents suitable for pharmaceutical, cosmetic, and food additive formulations.

In one embodiment, the invention includes planar ring structured organic compounds with the proviso that the planar ring structured organic compound is not a polyphenol, flavonoid and/or ubiquinone Q 10.

variety of applications. Disclosed herein are methods for substantially increasing the solubility of relatively water insoluble as well as relatively oil insoluble compounds within heat stable solubilizing compounds to enhanced concentration levels (e. g. up to about 10 or 20 wt % at ambient temperatures). The solubilized compound can be added to acceptable topical, subcutaneous, oral, peritoneal, periodontal, aerosol carriers to make formulations.

The subject invention relates to methods for substantially increasing the solubility concentrations of poorly soluble planar ring structured organic compounds, such as a flavonoids, with heat stable non-toxic solubilizing compounds, such as nonionic surfactant compounds, including polysorbates, comprising the steps of:

a) mixing a planar ring structured organic compound, such as a flavonoid, in a heat stable solubilizing compound to form a mixture, b) heating the mixture while stirring to a temperature where the planar ring structured organic compound particulates are solubilized and the resulting mixture (the "concentrate") forms a clear solution, and c) cooling the concentrate, and optionally adding a carrier.

The mixture is heated to an elevated temperature of greater than for example 100 degrees C., 120 degrees C., 150 degrees C., or 170 degrees C. The temperature selected is that which allows the planar molecules to go into solution. The mixture is heated to a temperature not exceeding the boiling point or decomposition point of either the planar compound or the solubilizing compound. The heating step is advantageously done with only the planar compound and the solubilizing compound present. The carrier is advantageously not present during mixing or heating. In many embodiments, the molar ratio of planar molecule to solubilizing compound approaches 1:2. The ratio of planar molecule to solubilizing compound approaches 1 mole of planar compound to 2 moles of solubilizing compound, e.g. surfactant for certain combinations. Significantly more surfactant than 1 mole active agent to 2 moles of surfactant is required for some active agent/surfactant combinations, e.g. 1 mole active agent to 20 moles of surfactant.

TABLE III

Solubility of Various Flavonoids in Surfactants/Solvents via the Thermal Treatment Process

| Compound | MW | MP °C | Lit. H2O Sol. (mg/ml) | PS80 Sol. Conc. (mg/Ml) | ~Sol. Temp. (C.) | (1)Jordi PS800 Results (mg/ml) | PEG400 Sol. Conc. (mg/ml) | (1)Jordi PEG400 Results (mg/ml) | DPSI PS80 Sol. Data (mg/ml) | DPSI PEG400 Sol. Data (mg/ml) | DPSI PEG300 Sol. Data (mg/ml) | Molar Ratio PS80/API (mole/mole) | Molar Ratio PEG400/API (mole/mole) |
|---|---|---|---|---|---|---|---|---|---|---|---|---|---|
| APIGENIN | 270 | 360 | 0.002 | 40-60 | ~270 | 40.5 | | 34.8 | 36-45 | 30-40 | 35-45 | 4.5 | 21.7 |
| LUTEOLIN | 286 | 330 | 0.38 | >80 | >200 | | 70-90 | 72.5 | | | | 3.0 | 11.4 |
| RESVERATROL | 228 | 255 | 0.1-0.3 | >80 | >200 | 127.5 | 80-100 | | | | | 2.4 | |
| QUERCETIN | 302 | 315 | <1 | >80 | >200 | 65 | 60-80 | | | | | 3.2 | |
| HEPERIDEN | 610 | 260 | 0.05-3 | <10: Dec | >200 | | <10: Dec | 81 | | | | | 21.2 |

The methods of this invention are applicable to poorly soluble flavonoids having a solubility in water less than 1 mg/ml, and particularly less than 0.1 mg/ml.

II—Methods of Preparing Formulations of the Compounds of the Invention

The subject invention includes multiple ways to formulate planar ring structured organic compounds allowing a wide For creation of a pharmaceutical composition, a nutraceutical, a dietary supplement, cosmeceutical, a food supplement, or medical food, after step b) or c) is the step of adding the solubilized compound mixture to a dermatological, oral, injectable, dermal patch, or aerosol carrier.

In another embodiment is the step of adding after step b) or c) an alcohol such as ethyl alcohol to the concentrate to form a soluble compound solution with a reduced viscosity. Other advantageous materials to reduce the viscosity level of the solubilized compound mixture include: small-chain alcohols (such as isopropyl and benzyl alcohol), ethoxydiglycol (diethylene glycol monoethyl ether or Transcutol), propylene glycol, hexylene glycol, butylene glycol, dipropylene glycol, glycerin, water, saline, DMSO, isopropyl myristate, mineral oil, low viscosity surfactants, and dimethyl isosorbide.

The method of the subject invention is useful in increasing the solubility of compounds that have poor solubility or that are currently solubilized in such a manner (e.g. as a salt) that precludes or makes difficult certain applications.

Apigenin/Polysorbate 80 formulations can be made as follows:

Apigenin powder and viscous liquid polysorbate 80 are mixed in the ratio from about 5 to 10 wt % of apigenin to 95 to 90 wt % polysorbate 80. A small quantity (5-10 wt %) of D.I. water and optionally acetone and/or ethyl alcohol is optionally added to facilitate the blending of the mixture.

This mixture is thoroughly stirred to form a thick paste-like blend.

The mixture is then slowly heated to relatively high temperatures (about 100 to 150° C.) while stirring. The heating is accompanied by the boiling off of the water and also volatile constituents present in the Polysorbate 80.

Upon the removal of the volatiles and heating to temperatures in excess of about 200 to 300° C., a dark brown transparent liquid results such that all the solid apigenin is solubilized in the Polysorbate 80 mixture.

Upon cooling to ambient temperatures, a thick viscous brown liquid results. The higher the apigenin content—the darker the resulting color.

Based on a 4.05% concentration of apigenin in the viscous apigenin polysorbate 80 liquid, the content of apigenin is 40.5 mg/ml or 40, 500 ppm.

It was unanticipated that high temperature levels were necessary to cause the high solubility level of apigenin and other relatively water insoluble flavonoids.

The use of apigenin/polysorbate 80 in an alcohol solution can deliver apigenin and other relatively insoluble flavonoids to the desired target location. The invention includes methods of combining heat stable compounds with the proper balance of polarity characteristics such as surfactants, with other flavonoids to achieve elevated concentration levels of the other flavonoids. Examples 2 and 3 show formulations of other flavonoids and polysorbates.

III. Formulations and Compositions of Planar Ring Compounds

The subject invention relates to compositions comprising a planar ring structured organic compound, such as a flavonoid, and a heat stable solubilizing compound such as a surfactant, wherein said composition is formed by mixing the planar compound and the solubilizing compound to an elevated temperature (typically >100° C.) where said planar compound is dissolved in said solubilizing compound. When the dissolved mixture is cooled to ambient temperatures, said dissolved planar compound remains dissolved even at concentrations exceeding the ambient temperature saturation concentration level. The concentration of the planar compound or active agent in the composition is greater than the ambient temperature and pressure saturation concentration of the active agent in said heat stable solubilizing compound, and said composition is not a supersaturated solution. The composition "concentrate' is stable for a time at least until a formulation is made from the concentrate.

As used herein, "a heat stable solubilizing compound" is a compound that is stable at least up to the melting of the planar ring structured organic compound to be solubilized. Upon thermal treatment (heating), the heat stable solubilizing compound when mixed with a planar ring structured organic compound, such as a flavonoid, solubilizes the planar ring structured organic compound, and upon cooling to ambient temperatures, continues to solubilize the planar ring structured organic compound. The mixture is heated to a temperature not exceeding the boiling point or decomposition point of either the planar compound or the solubilizing compound. For pharmaceutical, nutraceutical food and cosmetic applications the heat stable solubilizing compounds must be non-toxic at the levels used.

Advantageously, the planar ring structured organic compound solubilizing compound is capable of continuing to solubilize the planar ring structured organic compound at ambient temperatures for an extended period of time, e.g. 1 or 2 months, advantageously 1 or 2 years, but for at least as long as the time needed for the concentrate to be added to a carrier to make a formulation.

As used herein, "supersaturated solution" is a solution that contains higher than a saturated concentration of a solute; a slight disturbance or seeding causes crystallization of excess solute.

Heat stable solubilizing compounds that allow for enhanced solubility concentration levels of planar cyclic compounds employing the high temperature methods of this disclosure include sufactants Surfactants Surfactants are are classified as follows (see FIG. 1):

Surfactants According to the Composition of their Tail

The tail of surfactants can be:

A hydrocarbon chain: aromatic hydrocarbons (arenes), alkanes (alkyl), alkenes, cycloalkanes, alkyne-based;

An alkyl ether chain:

Ethoxylated surfactants: polyethylene oxides are inserted to increase the hydrophilic character of a surfactant;

Propoxylated surfactants: polypropylene oxides are inserted to increase the lipophilic character of a surfactant;

A fluorocarbon chain: fluorosurfactants;

A siloxane chain: siloxane surfactants

A surfactant can have one or two tails, these are called double-chained.

Surfactants According to the Composition of their Head

Surfactant classification according to the composition of their head: nonionic, anionic, cationic, amphoteric.

A surfactant can be classified by the presence of formally charged groups in its head. A non-ionic surfactant has no charge groups in its head. The head of an ionic surfactant carries a net charge. If the charge is negative, the surfactant is more specifically called anionic; if the charge is positive, it is called cationic. If a surfactant contains a head with two oppositely charged groups, it is termed zwitterionic.

Some commonly encountered surfactants of each type include:

Ionic
  Anionic: based on permanent anions (sulfate, sulfonate, phosphate) or pH-dependent anions (carboxylate):
    Sulfates:
      Alkyl sulfates: ammonium lauryl sulfate, sodium lauryl sulfate (SDS, sodium dodecyl sulfate, another name for the compound);
      Alkyl ether sulfates: sodium laureth sulfate, also known as sodium lauryl ether sulfate (SLES), sodium myreth sulfate;
    Sulfonates:
      Docusates: dioctyl sodium sulfosuccinate;
      Sulfonate fluorosurfactants: perfluorooctanesulfonate (PFOS), perfluorobutanesulfonate;
      Alkyl benzene sulfonates;
    Phosphates:
      Alkyl aryl ether phosphate
      Alkyl ether phosphate
    Carboxylates:
Alkyl carboxylates: Fatty acid salts (soaps): sodium stearate;
Sodium lauroyl sarcosinate;
Carboxylate fluorosurfactants: perfluorononanoate, perfluorooctanoate (PFOA or PFO)
    Cationic: based on:
      pH-dependent primary, secondary or tertiary amines: primary amines become positively charged at pH<10, secondary amines become charged at pH<4:
        Octenidine dihydrochloride;
      Permanently charged quaternary ammonium cation:
        Alkyltrimethylammonium salts: cetyl trimethylammonium bromide (CTAB) a.k.a. hexadecyl trimethyl ammonium bromide, cetyl trimethylammonium chloride (CTAC);
        Cetylpyridinium chloride (CPC);
        Polyethoxylated tallow amine (POEA);
        Benzalkonium chloride (BAC);
        Benzethonium chloride (BZT);
        5-Bromo-5-nitro-1,3-dioxane;
        Dimethyldioctadecylammonium chloride
        Dioctadecyldimethylammonium bromide (DODAB)
    Zwitterionic (amphoteric): based on primary, secondary or tertiary amines or quaternary ammonium cation with:
      Sulfonates:
        CHAPS (3-[(3-Cholamidopropyl)dimethylammonio]-1-propanesulfonate);
      Sultaines: cocamidopropyl hydroxysultaine;
      Carboxylates:
        Amino acids
        Imino acids
        Betaines: cocamidopropyl betaine;
      Phosphates: lecithin
Nonionic
  Fatty alcohols:
    Cetyl alcohol,
    Stearyl alcohol,
    Cetostearyl alcohol (consisting predominantly of cetyl and stearyl alcohols),
    Oleyl alcohol;
  Polyoxyethylene glycol alkyl ethers (Brij): $CH_3-(CH_2)_{10-16}-(O-C_2H_4)_{1-25}-OH$:
    Octaethylene glycol monododecyl ether,
    Pentaethylene glycol monododecyl ether;
  Polyoxypropylene glycol alkyl ethers: $CH_3-(CH_2)_{10-16}-(O-C_3H_6)_{1-25}-OH$;
  Glucoside alkyl ethers: $CH_3-(CH_2)_{10-16}-(O\text{-Glucoside})_{1-3}-OH$:
    Decyl glucoside,
    Lauryl glucoside,
    Octyl glucoside;
  Polyoxyethylene glycol octylphenol ethers: $C_8H_{17}-(C_6H_4)-(O-C_2H_4)_{1-25}-OH$:
    Triton X-100;
  Polyoxyethylene glycol alkylphenol ethers: $C_9H_{19}-(C_6H_4)-(O-C_2H_4)_{1-25}-OH$:
    Nonoxynol-9;
  Glycerol alkyl esters:
    Gliceryllaurate
  Polyoxyethylene glycol sorbitan alkyl esters: Polysorbates;
  Sorbitan alkyl esters: Spans;
  Cocamide MEA, cocamide DEA;
  Dodecyldimethylamine oxide;
  Block copolymers of polyethylene glycol and polypropylene glycol: Poloxamers Surfactants According to the Composition of their Counter-Ion In the case of ionic surfactants, the counter-ion can be:
  Monoatomic/Inorganic:
    Cations: metals: alkali metal, alkaline earth metal, transition metal;
    Anions: halides: chloride ($Cl^-$), bromide ($Br^-$), iodide ($I^-$);
  Polyatomic/Organic:
    Cations: ammonium, pyridinium, triethanolamine (TEA)
    Anions: tosyls, trifluoromethanesulfonates, methylsulfate Advantageous Surfactants are as Follows:

Amphoteric Surfactants

ALKYL AMMONIUM SULFONIC ACID
BETAINE
AMPHOTERIC-2
AMPHOTERIC-9
DISODIUM COCOAMPHODIACETATE
PHOSPHOLIPID
  USES/FUNCTIONS: Cleansers, Solubilizers, Emulsifiers
  ADMINISTRATION ROUTE: Topical, IV (Infusion)

Anionic Surfactants

ALKYL ARYL SODIUM SULFONATE
AMMONIUM LAURYL SULFATE
AMMONIUM NONOXYNOL-4 SULFATE
DISODIUM LAURETH SULFOSUCCINATE
DOCUSATE SODIUM/SODIUM BENZOATE
GLYCERYL STEARATE SE
LAURYL SULFATE
SODIUM CETOSTEARYL SULFATE
SODIUM DODECYLBENZENESULFONATE
SODIUM SULFOSUCCINATED UNDECYCLENIC MONOALKYLOLAMIDE
TROLAMINE LAURYL SULFATE
  USES/FUNCTIONS: Cleansers, Wetting agents, Solubilizers ADMINISTRATION ROUTE: Topical, Oral, Respiratory (inhalation), Sublingual Cationic Surfactants ALUMINUM STEARATE
APRICOT KERNEL OIL PEG-6 ESTERS
BEHENETH-10
   USES/FUNCTIONS: Emulsifiers, Solubilizers, Preservatives
   ADMINISTRATION ROUTE: Topical, Oral Ophthalmic, Nasal, Intramuscular, Auricular Nonionic Surfactants BENZALKONIUM CHLORIDE
CETEARETH-12, -15, -30
CETEARYL ALCOHOL/CETEARETH-20
CETETH-2, -10, -20
GLYCERYL STEARATE-LAURETH-23
GLYCERYL STEARATE/PEG STEARATE
GLYCERYL STEARATE/PEG-100 STEARATE
GLYCERYL STEARATE/PEG-40 STEARATE
LANOLIN NONIONIC DERIVATIVES
LANOLIN, ETHOXYLATED
LAURETH-2, -4, -23
LAUROYL POLYOXYLGLYCERIDES
OCTOXYNOL 9, -40
PEG VEGETABLE OIL
PEG-120 METHYL GLUCOSE DIOLEATE
PEG-150 DISTEARATE
PEG-22 METHYL ETHER/DODECYL GLYCOL COPOLYMER
PEG-25 PROPYLENE GLYCOL STEARATE
PEG-75 LANOLIN
PEG-8 CAPRYLIC/CAPRIC GLYCERIDES
PEG-8 LAURATE
PEGLICOL-5-OLEATE
PEGOXOL 7 STEARATE
POLOXAMER 124, −181, −182, −188, −237, −331, −338, −407
POLYGLYCERYL-10 OLEATE
POLYGLYCERYL-10 TETRALINOLEATE
POLYGLYCERYL-3 OLEATE, -4 OLEATE
POLYOXYL 100 GLYCERYL STEARATE
POLYOXYL 12 GLYCERYL LAURATE
POLYOXYL 2 STEARATE
POLYOXYL 20 CETOSTEARYL ETHER
POLYOXYL 20 STEARATE
POLYOXYL 35 CASTOR OIL
POLYOXYL 4 LAURATE
POLYOXYL 40 CASTOR OIL
POLYOXYL 40 HYDROGENATED CASTOR OIL
POLYOXYL 40 STEARATE, -50 STEARATE, -400 STEARATE
POLYOXYL 6 AND POLYOXYL 32 PALMITOSTEARATE
POLYOXYL 6 ISOSTEARATE
POLYOXYL 60 CASTOR OIL
POLYOXYL 60 HYDROGENATED CASTOR OIL
POLYOXYL 8 STEARATE
POLYOXYL GLYCERYL STEARATE
POLYOXYL LANOLIN, PALMITATE, -STEARATE
POLYSORBATE 20, -40, -60, -65, -80
PPG-15 STEARYL ETHER
PROPYLENE GLYCOL MONOSTEARATE
SORBITAN MONOLAURATE,
SORBITAN MONOPALMITATE
SORBITAN MONOSTEARATE
SORBITAN TRIOLEATE
STEARAMIDOETHYL DIETHYLAMINE
STEARETH-2, -10, -20, -21, -40, -100
SUCROSE PALMITATE
SUCROSESTEARATE
WAX, EMULSIFYING
   ADMINISTRATION ROUTE Topical, Oral, Intramuscular, Intralesional, Auricular (OTIC), Ophthalmic, Transdermal, Subcutaneous, IV (Infusion), Nasal, Periodontal, Vaginal
   USES/FUNCTIONS Emulsifiers, Solubilizers, Wetting agents, Gelling agents Silicone-Based Surfactants Also known as organosilicones, these are increasing in popularity because of their superior spreading ability. This class contains a polysiloxane chain. Some of these are a blend of non-ionic surfactants (NIS) and silicone while others are entirely silicone.

Non-Ionic Surfactants

Fatty acid esters of sorbitan (generally referred to as spans) and their ethoxylated derivatives (generally referred to as polysorbates) are perhaps the most commonly used nonionics. They can be used alone or in combination (e.g. polysorbate 80 and span 80) to form mixed micelles. The sorbitan esters are insoluble in water, but soluble in most organic solvents (low Hydrophile-Lipophile Balance (HLB) number surfactants). The ethoxylated products are generally soluble in water and have relatively high HLB numbers. These nonionic surfactants can be used alone or in a suitable combination to form mixed micelles of the desired HLB. One of the main advantages of the sorbitan esters and their ethoxylated derivatives is their approval as food additives. They are also used in cosmetics and pharmaceutical preparations.

Nonionic surfactant compounds that are useful for enhanced solubility concentration levels of flavonoids having solubility in water less than 1 mg/ml in water (employing the thermal treatment methods of this invention) include: ethoxylated aliphatic alcohols; polyoxyethylene surfactants; carboxylic esters; polyethylene glycol esters; anhydrosorbitol ester and its ethoxylated derivatives; glycol esters of fatty acids; and fatty amine ethoxylates.

The most common nonionic surfactants are those based on ethylene oxide, referred to as ethoxylated surfactants. Several classes can be distinguished: alcohol ethoxylates, alkyl phenol ethoxylates, fatty acid ethoxylates, monoalkaolamide ethoxylates, sorbitan ester and their ethoxylated derivates, ethoxylates, fatty amine ethoxylates, and ethylene oxide-propylene oxide copolymers (sometimes referred to as polymeric surfactants). Another important class of nonionics is the multihydroxy products such as glycol esters, glycerol (and polyglycerol) esters, glucosides (and polyglucosides) and sucrose esters. Amine oxides and sulphinyl surfactants represent nonionics with a small head group. (M J Schick (ed.): *Nonionic Surfactants: Physical Chemistry*, Marcel Dekker, New York, 1987)

HLB is an empirical expression for the relationship of the hydrophilic ("water-loving") and hydrophobic ("water-hating") groups of a surfactant. The higher the HLB value, the more water-soluble is the surfactant. The most common emulsion type, oil-in-water (o/w), often requires higher HLB surfactants—preferably 12-16 while water-in-oil emulsions (w/o) require low HLB surfactants—preferable 7-11. Surfactants with an HLB value<10 are oil-soluble while those >10 are water-soluble.

Span 20 is very suitable for water-in-oil topical formulations while Polysorbate 80 is very appropriate for solubilizing compounds in oil-in-water topical formulations. Surfactants with high HLB values like Polysorbate 80 are also applicable for making "concentrates" intended for use in the preparation of hydrophilic aqueous-based formulations and incorporation into to the aqueous phase of an emulsion. Whereas, surfactants with low HLB values like Span 20 are also applicable for making "concentrates" intended for use in the preparation of lipophilic nonaqueous-based formulations and incorporation into to the non-aqueous or oil phase of an emulsion.

Polysorbate Surfactants

Polysorbates (commercially also known as Tweens) are nonionic surfactants and emulsifiers derived from polyethoxylated sorbitan and fatty acids. They are often used in foods and in cosmetics to solubilize essential oils into water-based products. The polysorbates are viscous, water-soluble pale yellow liquids. Polysorbates also help to form emulsions by reducing the surface tension of the substances to be emulsified. Polysorbates have been recognized for their ability to help ingredients to dissolve in a solvent in which they would not normally dissolve. Polysorbates function to disperse oil in water as opposed to water in oil.

Polysorbates are produced by reacting the polyol, sorbitol, with ethylene oxide. The polyoxyethylenated sorbitan is then reacted with fatty acids obtained from vegetable fats and oils such as stearic acid, lauric acid, and oleic acid. Surfactants that are esters of plain (non-PEG-ylated) sorbitan with fatty acids are usually referred to by the name Span.

The polysorbates are composed of fatty acid esters of polyoxyethylene sorbitan, and their structures are typically presented as the chemically homogenous polysorbates shown in below. While the number of repeat ethylene oxide subunits varies at each position, their total number (w+x+y+z) is constant for each polysorbate (i.e., 20, 40 60, 80).

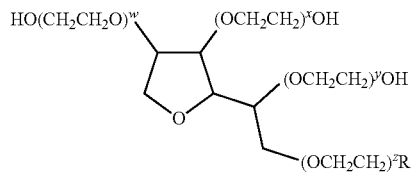

Polysorbates are a class of emulsifiers used in some pharmaceuticals and food preparation. They are often used in cosmetics to solubilize essential oils into water-based products. Polysorbates are oily liquids derived from PEG-ylated sorbitan (a derivative of sorbitol) esterified with fatty acids. Surfactants that are esters of plain (non-PEG-ylated) sorbitan with fatty acids are usually referred to by the name Span.

Polysorbate 20 (polyoxyethylene (20) sorbitan monolaurate)

Polysorbate 40 (polyoxyethylene (20) sorbitan monopalmitate)

Polysorbate 60 (polyoxyethylene (20) sorbitan monostearate)

Polysorbate 80 (polyoxyethylene (20) sorbitan monooleate)

The number 20 following the polyoxyethylene part refers to the total number of oxyethylene —$(CH_2CH_2)$— groups found in the molecule. The number following the polysorbate part is related to the type of fatty acid associated with the polyoxyethylene sorbitan part of the molecule. Monolaurate is indicated by 20, monopalmitate is indicated by 60, and monooleate by 80. The same numbering is followed in their Span equivalents (Span 20, Span 40, Span 60 and Span 80).

The invention includes methods for increasing the solubility concentrations of poorly soluble compounds with polysorbates. As previously noted, many flavonoids and specifically apigenin are poorly soluble in aqueous solutions thus severely limiting their bioavailability for topical, pharmaceutical and nutraceutical applications.

The subject invention includes a method for increasing the aqueous phase solubility levels of polyphenols by utilizing surfactant compounds, in particular Polysorbates 80, 60, 40 and 20. It should be noted that in this example polysorbates 20, 40 and 60 represent a homologous series of polysorbates with varying saturated fatty acids. The number of carbons in the fatty acid chain increases from 12 (polysorbate 20) to 18 (Polysorbate 60). Polysorbate 80 represents an unsaturated fatty acid with 18 carbon chain length (Oleate). These examples are not all inclusive and one trained in the art should recognize the usefulness of these types of nonionic surfactants with any other fatty acid and also other nonionic surfactants of other classes such as polyoxyethylene alkyl ethers of fatty acids.

PEG

Poly(ethylene glycol) (PEG), otherwise known as poly (oxyethylene) or poly(ethylene oxide) (PEO), is a synthetic polyether that is readily available in a range of molecular weights (MW). Materials with MW<100,000 are usually called PEGs, while higher molecular weight polymers are classified as PEOs. These polymers are amphiphilic and soluble in water as well as in many organic solvents. Low molecular weight (MW<1,000) PEGs are viscous and colorless liquids, while higher molecular weight PEGs are waxy, white solids with melting points proportional to their molecular weights to an upper limit of about 67° C. PEG or PEO has the following structure,

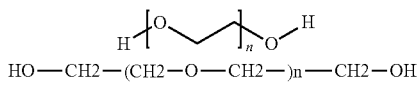

The numbers that are often included in the names of PEGs indicate their average molecular weights, e.g., a PEG with n=9 would have an average molecular weight of approximately 400 daltons and would be labeled PEG 400.

Anionic and Cationic Surfactants

It should also be noted that either anionic surfactants such as docussate sodium or sodium lauryl sulfate or cationic surfactants such as cetrimide or benzethonium chloride can also be used either alone or in combination with nonionic surfactants in the formulations of the invention. Significant aqueous phase enhancements exceeding more than two orders of magnitude have been achieved for several relatively water insoluble polyphenols.

The novel formulations with high planar compound concentrations can be utilized in oral, inhalation, topical, peritoneal, periodontal and suppository formulations. They are useful in pharmaceutical, cosmeceutical and nutraceutical applications (see below).

As used herein, the term "pharmaceutical composition" or "pharmaceutical formulation" shall mean a composition wherein the components of the composition or formulation are of pharmaceutical grade. The compositions or formulations can conveniently be presented in unit dosage form, and can be prepared by methods known in the art of pharmacy.

The formulations can be for immediate, or slow or controlled release of the diffusion enhancing compound. The advantages of a sustained release system (also known as time release, controlled release, etc.) are that dosing frequency can decrease and the systemic drug concentrations are steadier for a longer duration as compared to other formulations of the same drug. Appropriate dosages of the compositions of the invention will depend on the mode of administration, metabolism of the given compound, and the severity of the condition being treated.

The subject invention includes multiple ways to formulate planar compounds such as flavonoids, allowing a wide variety of applications. The compounds, compositions and formulations of the invention are useful in the prevention of and the treatment of the disorders and diseases discussed below. As used herein, a "therapeutically effective amount" is the dose necessary to have the desired effect. For example in the case of plaque psoriasis, a therapeutically effective amount is that amount which reduces the sizes or severity of the patches or plaques. A "prophylactic amount" is that dose which prevents or reduces the likelihood of a disorder or disease occurring.

Table IV lists a variety of dosage types and forms that can serve as a means for delivering the subject formulations.

TABLE IV

DOSAGE TYPES & FORMS

| TYPE | FORMS |
|---|---|
| ORAL | Capsule, Thin film, Liquid Solutions |
| INHALATION | Aerosol, Inhaler, Nebulizer, Smoking, Vaporizer |
| PERIDONTAL | Liquid Solution, Paste, Spray |
| PARENTERAL INJECTION | Intradermal, Intramuscular, Intraosseous, Intraperitoneal, Intravenous, Subcutaneous |
| TOPICAL | Cream, Gel, Liniment or Balm, Lotion, Ointment, Solution, Spray, Foam, Ear drops, Eye drops, Skin patch (transdermal) |
| SUPPOSITORY | Rectal (e.g., enema), Vaginal (e.g., douche, pessary, etc.) |

A. Topical Administration

Topical administration of solubilized compounds is typically done in the form of a patch, lotion, cream, gel, solution, spray, liquids and serums, foam or ointment. The methods described above for increasing the solubility levels of flavonoids or other poorly soluble planar compounds in surfactant enable the formulation of lotion, cream, gel, solution, spray, foam or ointment topical products wherein the planar compound is in solution; a physical state of the relatively insoluble planar compound not achievable without the use of these methods.

Transdermal Delivery

The methods described for increasing the solubility levels of planar compounds within surfactants enable the transdermal delivery into the systemic circulation via permeation at a controlled rate. The subject formulations offer a noninvasive route of drug administration by addressing issues related to the inherently low permeability of skin. The skin is a good barrier to drug penetration. Incorporation of penetration enhancers facilitates the absorption of drugs by altering the barrier property of the stratum corneum. Several nonionic surfactants such as polysorbate 80 in topical, oral, and peritoneal applications are considered to be pharmacologically inert, nontoxic, nonirritating, nonallergic, odorless, compatible with most drug and excipients, and have good solvent properties.

Penetration Enhancers

Different classes of penetration enhancers including alcohols and polyols (ethanol, glycerol, propylene glycol), surfactants (Tween, Span), fatty acids (Oleic acid), amines and amides (Azone, N-methylpyrrolidone), terpenes (limonene) sulfoxides (dimethylsulfoxide-DMSO), esters (isopropyl myristate) have been developed over the past two decades (French E, Potton C, Walters K. *Pharmaceutical skin penetration enhancement*. In: Walters K, Hadgraft J, editors. New York: Marcel Dekker; 1993. p. 113-44).

Microemulsions

Another formulation approach aiming to enhance skin penetration is the preparation of microemulsions. Microemulsions consist of water, oil, and surfactant that yield a transparent thermodynamically stable liquid. Properties of microemulsions include optical transparency, thermodynamic stability, and solubility of both hydrophobic and hydrophilic components. Microemulsions are clear, stable, isotropic liquid mixtures of oil, water and surfactant, frequently in combination with a cosurfactant. The aqueous phase may contain salt(s) and/or other ingredients, and the "oil" may actually be a complex mixture of different hydrocarbons and olefins. In contrast to ordinary emulsions, microemulsions form upon simple mixing of the components and do not require the high shear conditions generally used in the formation of ordinary emulsions. The two basic types of microemulsions are direct (oil dispersed in water, o/w) and reversed (water dispersed in oil, w/o).

Penetration enhancement from microemulsions can be due to an increase in drug concentration which provides a large concentration gradient from the vehicle to the skin. The nonionic surfactants solvents containing the enhanced flavonoid concentrations (described herein) are well suited for the preparation of microemulsions for transdermal, oral and peritoneal applications.

In one embodiment, a microemulsion contains apigenin is dissolved in polysorbate 80 together with water and ethyl alcohol as a cosurfactant and an oil phase of isoproyl myristate (IPM). This embodiment has topical applications, due to skin penetration properties, as well as oral, injection and nasal spray applications.

The formulations disclosed in this invention allow enhanced transdermal drug delivery methodologies for flavonoids. Of particular note are the disclosed formulations of relatively water insoluble flavonoids, including apigenin, solubilized in nonionic surfactants mixtures. In vitro skin penetration testing with human and mouse skins demonstrated unexpectedly high apigenin accumulation within the epidermal and dermal layers resulting from the application of the disclosed nonionic surfactant mixtures. See Example 15.

Transdermal Patches

Useful for transdermal active agent delivery of poorly soluble planar compounds, is the use of transdermal patches containing the solubilized compound within the solubilizing agent such as a surfactant, diluted with an alcohol such as the relatively volatile ethyl alcohol. The outer nonporous barrier of the patch when applied to the skin serves to reduce the evaporation of the relatively volatile alcohol thereby allowing for the increased penetration and delivery of the active agent. Other solvent diluents used in cosmetic and foods applications such as alcohols (i.e., ethyl alcohol, glycols, ethoxydiglycol etc.), esters (dimethyl isosorbide etc.) serve to reduced the viscosities of relatively viscous nonionic surfactant thereby increasing the rate and depth of skin penetration when applied to the skin's surface or contained within transdermal patches. Particularly, useful for dermal patch and transdermal patch, are the use of microemulsion formulations of active agents. The formulations consist of oil-in-water and water-in-oil type microemulsions.

Transdermal patches can be classified into two types of delivery systems—reservoir based and matrix based. Compositions for both are similar except that semipermeable membranes are used to control the diffusion from the reservoir system. Examples of membranes used include polypropylene, low density polyethylene, ethylene-vinyl acetate co-polymer etc. In matrix based formulations drugs can be dispersed/solubilized in the adhesives. Two commonly used adhesive classes include acrylate and silicone based materials. Examples of pressure sensitive acrylate adhesives include, but are not limited to, the DURO-TAK® series (Henkel, USA). Examples of pressure sensitive silicone adhesives include, but are not limited to, the Bio-PSA® series (Dow Corning, USA). Additional information relating to some specific acrylate and silicone based pressure sensitive adhesives are summarized in Table V.

TABLE V

A SUMMARY OF ACRYATE & SILICONE BASED PRESSURE SENSITIVE ADHESIVES

| ADHESIVE DESCRIPTION | SOLVENT SYSTEM | POLYMER | NOTES |
| --- | --- | --- | --- |
| DURO-TAK® 87-900A | Ethyl acetate | Acrylic non-curing | Reactive or sensitive API's |
| DURO-TAK® (3)87-2516 | Ethyl acetate Ethanol | Acrylate-vinylacetate; self-curing | Long term wear |
| DURO-TAK® 87-4287 | Ethyl acetate | Acrylate-vinylacetate; non-curing | Long term wear |
| BIO-PSA 7-4202 Silicone adhesive BIO-PSA 7-4302 Silicone adhesive | Ethyl acetate | Trimethylsiloxy silanol endblocked PDMS | Amine-compatible |

Solvents and penetration enhancers known to those skilled in the art can also be included in the compositions. Potential, solvents/enhancers can include but are not limited to fatty acids (oleic acid), esters (isopropyl myristate), alcohols (ethyl and isopropyl) and glycols (propylene glycol, hexylene glycol). Other components can include antioxidants (e.g. BHT and BHA) or chelating agents (e.g. citric acid).

In Example 15, the formulations of the subject invention delivered significant apigenin concentrations to both the epidermal and dermal skin layers.

B. Oral Administration

Formulations of this invention can also be administered orally. For oral administration, compositions disclosed herein can be in the form of, for example, liquid gel capsules or solutions. For oral administration, the compositions disclosed can be in any orally acceptable dosage form including, but not limited to emulsions, microemulsions, and aqueous solutions, and liquid gel capsules.

When the compounds are prepared for oral administration, they are generally combined with a pharmaceutically acceptable carrier, diluent or excipient to form a pharmaceutical formulation, or unit dosage form. For oral administration, compounds can be present as a solution, a suspension, an emulsion or in a natural or synthetic polymer or resin for ingestion of the active ingredients from a chewing gum.

Orally administered compounds can also be formulated for sustained release, e. g., flavonoids can be coated, microencapsulated, or otherwise placed within a sustained delivery device. The total active ingredients in such formulations comprise from 0.01 to 10% by weight of the formulation.

Pharmaceutical formulations can be prepared by procedures known in the art using well-known and readily available ingredients. For example, the flavonoids can be formulated with common excipients, diluents, or carriers, and formed into dosage forms such as capsules, solutions, suspensions, aerosols and the like. All of these dosage forms can be for immediate release, sustained release or enteric coated. These can be either for peroral or sublingual or buccal delivery. Examples of excipients, diluents, and carriers that are suitable for such formulations include fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive carriers such as kaolin and bentonite can be added. Lubricants such as talc, calcium and magnesium stearate, and solid polyethyl glycols can also be included.

The compositions of the invention can also contain thickening agents such as cellulose and/or cellulose derivatives. They can also contain gums such as xanthan, guar gum or gum arabic, or alternatively polyethylene glycols, bentones and the like.

Soft gelatin capsules containing flavonoids can contain inactive ingredients such as gelatin, microcrystalline cellulose, glycerin, sodium lauryl sulfate, starch, talc, and titanium dioxide, and the like, as well as liquid vehicles such as polyethylene glycols (PEGs) and vegetable oil. Moreover, enteric-coated capsules containing flavonoids or other compounds are designed to resist disintegration in the stomach and dissolve in the more neutral to alkaline environment of the duodenum are typically coated with cellulose acetate derivatives.

The planar compounds can also be formulated as elixirs or solutions for convenient oral administration. The pharmaceutical formulations of the flavonoids can also take the form of an aqueous or anhydrous solution or dispersion, or alternatively the form of an emulsion or suspension.

C. Parenteral Administration

The formulations of this invention can also be administered parentally. For parenteral administration, the compositions disclosed herein can be in the form of injectable solutions or suspensions, such as saline solutions. The term "parenteral," as used herein includes intravenous, subcutaneous, intramuscular, intrasynovial, intrasternal, intralesional and intracranial injection or infusion techniques. Typical formulations include emulsions and microemulsions. Injectable formulations, including emulsions, frequently consist of mixtures of purified water for injection, organic cosolvents, surfactants, suspending agents, preservatives, antioxidants and pH adjusters. Examples of ingredients illustrating each category are as follows, but not limited to:

Cosolvents

Propylene glycol, ethyl alcohol, glycerin, polyethylene glycols, benzyl alcohol, vegetable oil, soybean oil, safflower oil, cottonseed oil, corn oil, peanut oil, sunflower oil, *arachis* oil, castor oil, olive oil, ester of a medium or long chain fatty acid such as a mono- di- or triglyceride, ethyl oleate, isopropyl myristate, polyoxyl hydrogenated castor oil, phospholipids and combinations thereof.

Surfactants

Polyoxyethylene/polyoxypropylene block copolymers, phosphatides, and polysorbates are commonly used as synthetic nonionic surfactants Suspending Agents Polyvinyl pyrrolidone (PVP), sodium carboxymethylcellulose and dextran Preservatives Disodium edetate, sodium benzoate, benzalkonium chloride, benzoic acid methylparaben and propylparaben Antioxidants Ascorbic acid, butylated hydroxytoluene, butylated hydroxyanisole, sodium thiosulfate pH Adjusters Sodium hydroxide, tromethamine, sodium citrate, sodium phosphate dibasic and monobasic, sodium acetate, citric acid, phosphoric acid, acetic acid and phosphoric acid.

D. Inhalation Administration

The formulations of this invention can also be administered by inhalation means. For inhalation administration, the compositions disclosed herein can be in the form of aerosols which deliver the flavonoid ingredients as a suspension of fine liquid droplets in a gas to the mouth or nasal passages. Vaporizer and inhalation devices facilitate in the delivery of the flavonoid ingredients.

The compositions can be administered to the respiratory tract. The composition can be presented in unit dosage form in, for example, capsules or cartridges, or, e.g., gelatin or blister packs from which the composition may be administered with the aid of an inhalator, insufflator, or a metered-dose inhaler (MDI) or dry powder inhaler (DPI).

The compounds can also be administered in an aqueous solution when administered in an aerosol or with a dropper. Thus, other aerosol pharmaceutical formulations can comprise, for example, a physiologically acceptable buffered saline solution containing between about 0.01-10% of the disclosed flavonoid ingredients. Liquid formulations may also contain preservatives such methyl and propyl paraben, benzalkonium chloride etc, buffers such as phosphate and citrate buffers, tonicity adjusters such as mannitol, sodium chloride etc and antioxidants such as ascorbic acid, sodium metabisulfite, sodium thiosulfate etc and colors such as D&C yellow #10, FD&C yellow #6 etc.

For administration to the upper (nasal) or lower respiratory tract by inhalation, the active agents are conveniently delivered from a nebulizer or a pressurized pack or other convenient means of delivering an aerosol spray. Pressurized packs can comprise a suitable propellant such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Products can also be delivered by use of nebulizers.

For intra-nasal administration, the therapeutic agent can also be administered via nose drops, a liquid spray, such as via a plastic bottle atomizer or metered-dose inhaler. Typical of atomizers are the Mistometer (Wintrop) and the Medihaler (Riker).

Carriers and Vehicles

In addition to the active agents, the formulations comprise one or more vehicle such as a "pharmaceutically acceptable" or cosmetically or "dermatologically acceptable" carrier/vehicle. A "pharmaceutically acceptable carrier" does not substantially adversely affect the pharmacological activities of the active agent, is not deleterious or unsuitably harmful to the recipient thereof and is non-toxic when administered at dosages sufficient to deliver an effective amount of the active ingredient, and the carrier (diluent, excipient, and/or salt etc.) is compatible with the other ingredients of the formulation. Likewise, a "dermatologically acceptable carrier" has the same qualities.

A dermatologically acceptable carrier typically includes ingredients that are chemically and physically compatible with the active ingredient(s), stable with an adequate shelf life, and that aid in delivery of the active ingredient(s) into the skin (e.g., to the epidermis and/or dermis) following topical administration. Optionally, the dermatological carrier contains ingredients that contribute to the ease of application and have pleasing aesthetic properties (color, scent, feel etc.).

Formulation objectives with respect to the drug delivery profile depend on the intended use of a topical product. For sunscreens, antifungals, and keratolytic formulations, enhanced drug delivery and retention in the stratum corneum (the outer layer of skin) is desired. Conversely, topical formulations that are intended to modify the physiology of the skin require drug deposition in and often through the lower layers of the skin (viable epidermis and dermis).

The carrier can act, for example, as a diluent, dispersant, and/or carrier for other materials present in the formulation (for example, so as to facilitate their distribution when the composition is applied to the skin). Some exemplary vehicles include: organic constituents (such as alcohols, oils, and the like), aqueous based solvents (e.g., those which can dissolve or disperse the active flavone ingredients, e.g., at concentrations that are suitable for use in the therapeutic treatment).

More specifically, the carrier(s) can include ethanol, isopropanol, benzyl alcohol, glycol (e.g., polyethylene glycols, propylene glycol, ethoxydiglycol, and so forth), oils (such as grapeseed, jojoba, coconut, sesame, mineral etc.), glycerol, fatty acid esters, dimethyl isosorbide, as well as combinations comprising at least one of the foregoing carriers.

The carrier, which can be present in the formulation in an amount of less than or equal to 99.99 wt %, for example, 80 wt % to 99.99 wt %, based upon a total weight of the formulation, can be in any of the various forms of the desired final formulation as discussed above.

Carrier components in addition to water and oils can also include liquid emollients, solid emollients, solvents, humectants, thickeners, powders, fragrances, odor masking agents, colorants, dispersants, lubricants, silicates as well as combinations comprising at least one of the foregoing. Exemplary solvents include ethyl alcohol, isopropanol, ethoxydiglycol, and dimethyl isosorbide, and acetone, as the prevention and/or relief of dryness, and/or for the protection of the skin, such as stearyl alcohol, cetyl alcohol, acetylated lanolin alcohols, stearic acid, isobutyl palmitate, isocetyl stearate, cetyl palmitate, isopropyl stearate, butyl stearate, lanolin, cocoa butter, shea butter, oil (e.g., olive oil, sunflower seed oil, avocado oil, mineral oil), petroleum jelly, and myristate (e.g., butyl myristate, isopropyl myristate, myristyl myristate), as well as combinations comprising at least one of the foregoing.

In an embodiment of the invention, the compositions are formulated with an enteric coating to release the active agent in the intestines.

Additives

Hyaluronic Acid (HA)

Within the dermal structure, HA functions as a space filling, structure stabilizing, and cell protective molecule with remarkable malleable physical and superb biocompatibility properties. Additionally, HA structures, which have a high level of visoelasticity, serve to preserve a high level of hydration with this skin. A strong correlation exists between the water content in the skin and levels of HA within the dermal tissue. It is well documented that there are significant alterations in HA physical and biological properties as skin ages—particularly in metabolism, content and deterioration in the mechanical properties of the skin. It is believed that the maintaining of a viable HA presence within the skin's intercellular structure contributes to the viability of a healthy skin physical appearance.

In another aspect, it has been well documented that polysaccharide molecules such as HA do degrade as a consequence of enzymatic and oxidative (free radical) mechanisms. Consequently, it is desirable to develop topical formulations that serve to prevent the decomposition of polysaccharides such as HA. To this end, flavonoids such as flavones serve to meet this need via their well-documented anti-hyaludonidase and anti-oxidant properties—thereby serving to maintain the viability of HA desirable functions protecting against the mechanisms which contribute to its breakdown.

Topically, HA has water storing properties, making it beneficial as a swelling agent and lubricant, enabling its incorporation into cosmetics leading to a perceptible and visible improvement of skin condition. In use, it forms a thin transparent visco elastic surface film that helps to preserve the characteristics of youthful and healthy skin: suppleness, elasticity and tone. Increased skin hydration may swell and open up the compact structure of the stratum corneum, leading to an increase in penetration of the active flavonoids ingredients of the topical formulations described herein.

The formulation can further comprise additive(s) so long as the specific additive(s) do not adversely affect the active ingredient(s). Some possible additive(s) that can be used in the various embodiments of the formulation include:

antioxidant(s) (e.g., tocopherol, tocopheryl acetate, butylated hydroxytoluene, sodium metabisulfite, sodium thiosulfate, and propyl gallate), surfactant(s) (e.g., that can reduce the interfacial tension between phases and/or improve stability of the formulation, and/or that can act as emulsifiers, such as glyceryl stearate, stearyl alcohol, cetyl alcohol, stearic acid dimethicone, a silicone (siloxane) surfactant, polysorbates, sodium laureth), skin conditioning agent(s) such as silicone oils, preservative(s) (e.g., methylparaben, propylparaben, benzyl alcohol, benzalkonium chloride etc.), humectants(s) or emollients or moisturizers such as glycerol, polyethylene glycol, glycerin, sorbitol, mineral oil, isopropyl myristate, etc., buffer(s) (such as phosphate buffers, citrate buffers, and acetate buffers, etc.) pH adjusters such as triethanolamine, potassium hydroxide, sodium hydroxide), hydrochloric acid and phosphoric acid etc., gelling agents such as hydroxypropyl ethyl cellulose, hydroxyrthyl cellulose, polyacrylic acid polymers, and poloxamers, etc.

vitamin(s) (e.g., A, B C, D, E, K, etc.), mineral(s), plant extract(s) (e.g., aloe vera, witch hazel, elderflower, cucumber, chamomile, etc.), anti-inflammatory agent(s), emollient(s), moisturizer(s), skin protectant(s), silicone(s), analgesic(s), skin penetration enhancer(s), such as propylene glycol, transcutol, isopropyl myristate, colorant(s) such as yellow no. 5, fragrance(s) (or perfume), wax(es) (e.g., beeswax, paraffin wax, etc.), propellant(s) (e.g., compressed air, hydrocarbons (such as propane, butane, isobutene, etc.), sunscreen ingredient(s) (e.g., inorganic and/or organic sunscreens, such as titanium oxides, zinc oxides, avobenzone, oxybenzone, homosalate, octocrylene octinoxate etc.), or a combination comprising at least two of the forgoing.

For sunscreens, the formulation can contain 0.01 wt % to 20 wt % sunscreen ingredient(s), specifically, 0.1 wt % to about 10 wt %, and more specifically, 0.5 wt % to 5 wt % based upon a total weight of the formulation. For skin products, those vehicles that are fat-soluble, i.e., those which can effectively penetrate skin layers and deliver the flavonoids to the lipid-rich layers of the skin. A formulation containing dispersed and/or solubilized flavonoids in an admixture colloidal form can be added to a vehicle together with the oxides of titanium and zinc such that the flavonoids will preferentially be absorbed within the user's skin while the phase containing the zinc and titanium oxides will not be absorbed but will form a protective UV film barrier external to the surface of the skin.

The concentrate of the invention can be loaded into a formulation by adding it into an oil/water ("o/w") and/or water/oil/water ("w/o/w") emulsion, which can comprise dispersant(s), emulsifiers, surfactants, and the like.

It is noted that, while the carrier can comprise a relatively simple solvent or dispersant (such as oils and organic alcohols), it is generally preferred that the carrier comprise a composition more conducive to topical application, and particularly one which will form a film or layer on the skin to which it is applied so as to localize the application and provide some resistance to perspiration and/or one which aids in delivery to the skin (e.g., to the skin's subsurface layers) and penetration of the active ingredients into the lipid layers of the skin. Many such compositions take the form of lotions, creams, sprays and gels. Typical compositions include lotions containing water and/or alcohols, emollients (such as hydrocarbon oils, hydrocarbon waxes, silicone oils, vegetable fats and/or oils, animal fats and/or oils, marine fats and/or oils, glyceride derivatives, fatty acids, fatty acid esters, alcohols (e.g., polyhydric alcohols, alcohol ethers), lanolin (including derivatives), esters (e.g., polyhydric esters, wax esters), sterols, phospholipids, as well as combinations comprising at least one of the foregoing), and generally also emulsifiers (nonionic, cationic or anionic). These same general ingredients can be formulated into a cream rather than a lotion, or into gels, by utilization of different proportions of the ingredients and/or by inclusion of thickening agents such as gums or other forms of hydrophilic colloids.

In one embodiment, the formulation comprises the planar compound in both the dissolved and dispersed (e.g., microparticulate) forms. The dissolved form(s) can penetrate the skin layers to become bioactive while the dispersed compounds can serve as a reservoir for maintaining a dissolved concentration level as the dissolved compounds are consumed so as to maintain sustained delivery.

A formulation can be prepared using a lecithin-based oil-in-water cream with about 2.0 wt % apigenin and about 0.5 wt % ascorbic acid, with about 0.5 wt % tocotrienol acetate and about 0.25 wt % glycolic acid with the balance comprising the vehicle's components, based upon a total weight of the formulation.

In another example, the formulation can be prepared using a lecithin-based oil in water cream, 3.0 wt % with lecithin, about 0.5 wt % ascorbic acid, about 0.5 wt % tocotrienol acetate, about 0.25 wt % glycolic acid, and about a total of 8 wt % of the oxides of zinc and titanium, with the balance comprising the vehicle's components, based upon a total weight of the formulation.

Optionally, the composition can further comprise: (i) an additive selected from the group consisting of surfactants, vitamins, minerals, plant extracts, anti-inflammatory agents, concentrates of plant extracts, emollients, moisturizers, skin protectants, humectants, silicones, skin soothing ingredients, skin penetration enhancers, colorants, perfumes (fragrances), preservatives, pH adjusters, and a combination comprising at least one of the forgoing; and/or (ii) titanium oxide, zinc oxide, or a combination comprising at least one of the forgoing.

Generally, the planar compound compositions can comprise greater than or equal to 0.01 weight percent (wt %) planar compound, specifically, greater than or equal to 1 wt %, for example, 0.1 wt % to 10 or 20 wt %, specifically, 0.5 wt % to 8 wt %, more specifically, 2 wt % to 5 wt %, based upon a total weight of the composition. The formulation can comprise greater than or equal to 0.01 wt % (e.g., 0.01 wt % to 20 wt % planar compound, specifically, 0.05 wt % to 15 wt %, more specifically, 0.1 wt % to 10 wt % planar compound, yet more specifically 0.5 wt % to 4 wt % planar compound, and even more specifically, 1 wt % to 2 wt % based upon a total weight of the formulation.

Ranges disclosed herein are inclusive and combinable (e.g., ranges of "up to 25 wt. %, or, more specifically, 0.5 wt. % to 5 wt. %", is inclusive of the endpoints and all intermediate values of the ranges of "5 wt. % to 25 wt. %," etc.). "Combination" is inclusive of blends, mixtures, alloys, reaction products, and the like. Furthermore, the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. As used herein, the term "(meth)acrylate" encompasses both acrylate and methacrylate groups.

Examples of formulations of the invention are set forth in Table VI.

TABLE VI

EXAMPLES OF FORMULATIONS CONTAINING THE DISCLOSED SOLUBILIZED ACTIVE AGENTS

| FORMULATION TYPES | EXAMPLES OF FORMULATIONS CONTAINING THE DISCLOSED SOLUBILIZED ACTIVE AGENTS |
|---|---|
| CAPSULES | Capsules containing the poorly soluble active agents & other active ingredients may include the following ingredients: 0.01-10% of the disclosed active agents; and 90-99.9% of inactive ingredients including oils, emulsifiers, solvents, saline solutions, preservatives |
| Emulsions (LOTIONS, CREAMS), & GELs | An emulsion is a thermodynamically unstable system consisting of at least two immiscible liquid phases, one of which is dispersed in the other liquid phase. The system is stabilized by the presence of an emulsifying agent. When the oil phase is dispersed throughout an aqueous continuous phase, the system is referred to as an oil-in-water (o/w) emulsion. When the oil phase serves as the continuous phase, the emulsion is referred to as water-in-oil (w/o) emulsion. Both lotions and creams are emulsions. Creams are thicker than lotions. Gels consist of a solid three-dimensional work of a gelling agent that spans the volume of a liquid medium. The key components include: 0.01-10% of the disclosed active agents and other active ingredients; and 90-99.9% of other ingredients such as emulsifiers (surfactants), humectants, emollients, oils, fatty acids, solvents, stabilizing agents, gelling agents, preservatives, vitamins, penetration enhancers, dyes, fragrances, etc, are commonly added ingredients |
| OINTMENTS | Ointments are homogeneous, viscous semi-solid preparations. They are formulated using hydrophobic, hydrophilic, or water-emulsifying bases to provide preparations that are immiscible, miscible, or emulsifiable with skin secretions. The key components include: 0.01-10% of the disclosed active agents & other active ingredients; and 90-99.9% including the ointment base consisting of paraffins, beeswax, vegetable oils, fatty acids, stabilizers, emulsifiers, humectants, preservatives, fragrances, etc. |
| DERMAL & TRANSDERMAL PATCHES | Dermal & Transdermal Patches include the following key ingredients contained within a porous matrix support: 0.01-10% of the disclosed active agents & other active ingedients; and 90-99.9% including penetrating agents, preservatives, stabilizers, gelling agents, solvents such as short chain alcohols, pH adjusters, saline solutions, etc. |
| INJECTABLES | Injectables include the following key components: 0.01-10% of the disclosed active agents & other active ingredients; and 90-99.9% including preservatives, stabilizers, solvents such as water and short chain alcohols, buffer, pH adjusters, saline solutioms, etc. |
| NASAL Formulations (Solutions, Sprays, gels and ointments) | Nasal sprays may be atomized into a fine aerosol mist to include the following ingredients: 0.01-10% of the disclosed active agents & other active, ingredients; and 90-99.9% including vegetable derived oils, saline solutions, solvents, stabilizers, surfactants, buffers, preservatives, pH adjusters, gelling agents and petroleum etc. |

Advantageous Topical Compositions

The following compositions are advantageous embodiments of the invention. In other embodiments, another flavonoid, e.g. luteolin, or combination of flavonoids, can be substituted for apigenin, and another surfacant can be substituted for polyorbate 80 to make the concentrate. In still further embodiments of the invention, other planar compounds of the invention, e.g. polyphenols, can be substituted for apigenin.

An apigenin formulation using a dimethyl sulfoxide-water solution comprising 1 to 20 wt % (advantageously about 10 wt %) apigenin/polysorbate-80 concentrate, 0 to 99.9 wt % (advantageously about 45 wt %) dimethyl sulfoxide, and the balance comprising water, based upon a total weight of the formulation.

An apigenin gel formulation using a dimethyl sulfoxide-water solution comprising 1 to 20 wt % (advantageously about 10 wt %) apigenin/polysorbate-80 concentrate, 0 to 60 wt % (advantageously about 45 wt %) dimethyl sulfoxide, 2 to 4 wt % (advantageously about 3 wt %) hydroxypropyl cellulose (quantity sufficient to achieve desired viscosity), and the balance comprising water, based upon a total weight of the formulation.

An apigenin solution formulation using an ethanol-water solution comprising 1 to 20 wt % (advantageously about 10 wt %) apigenin/polysorbate-80 concentrate, 0 to 80 wt % (advantageously about 66 wt %) ethanol, 0 to 20 wt % (advantageously about 10 wt % propylene glycol), and the balance comprising water, based upon a total weight of the formulation.

An apigenin gel formulation using an ethanol-water solution comprising 1 to 20 wt % (advantageously about 10 wt %) apigenin/polysorbate-80 concentrate, 0 to 80 wt % (advantageously about 66 wt %) ethanol, 0 to 20 wt % (advantageously about 10 wt %) propylene glycol, gelled with either ~0.5 to ~2.5 wt % hydroxyethyl cellulose or ~0.5 to ~2.5 wt % sodium hyaluronate or ~0.5 to ~2 wt % carbopol (quantity sufficient to achieve desired viscosity), and the balance comprising water, based upon a total weight of the formulation.

An apigenin emulsion formulation comprising 1 to 20 wt % (advantageously about 5 to 10 wt %) apigenin/polysorbate-80 concentrate, 0 to 20 wt % (advantageously about 10 wt %) ethoxydiglycol, 0 to 20 wt % (advantageously about 12 wt %) myristyl lactate, 0.1 to 1.0 wt % (advantageously about 0.4 wt %) carbopol 980, 0.1 to 1.0 wt % (preferably 0.3 wt %) Pemulen TR1, ~0.17 wt % methylparaben, ~0.03 wt % propylparaben, ~0.1 wt % EDTA, 0 to 15 wt % (advantageously about 10 wt %) cyclomethicone, 0 to 10 wt % (advantageously about 2 wt %) oleyl alcohol, ~0.1 wt % butylated hydroxytoluene, and the balance comprising water (with the final pH adjusted to ~6.5 using dilute HCl or a 10% sodium hydroxide solution), based upon a total weight of the formulation. Pemulen polymers are high molecular weight, crosslinked copolymers of acrylic acid and C10-C30 alkyl acrylate. Carbopol 980 is a crosslinked polyacrylate polymer.

Nutraceuticals/Dietary Supplements

A solubilized compound, such as a polyphenol concentrate, or formulation of such concentrate, can be used for many nutraceutical products such as isolated nutrients, fortified foods and dietary supplements. As used herein, a nutraceutical is any nontoxic food extract supplement that has scientifically proven health benefits for both the treatment and prevention of disease.

Food/Medical Foods

Medical foods are formulated to be consumed or administered internally under the supervision of a physician. They are intended for the specific dietary management of a disease or condition for which distinctive nutritional requirements, on the basis of recognized scientific principles, are established by medical evaluation. Medical foods can be ingested through the mouth or through tube feeding. Medical foods are always designed to meet certain nutritional requirements for people diagnosed with specific illnesses. A planar compound concentrate, such as flavonoid concentrate, or a formulation thereof, can be used in medical foods. For example, the addition of a polyphenol (e.g. flavonoid) concentrate to beverages (e.g. alcohol types) will serve as a means for the oral delivery of poorly soluble but beneficial polyphenols. Also included in the invention are functional beverages and functional shots, genetically engineered "designer" food, herbal products, and processed products such as cereals, soups, and beverages which include a concentrate.

Cosmetics/Cosmeceuticals

The concentrates or formulations of the subject invention, e.g. including polyphenol concentrates, can be used in many products such as cosmetic and dermatological products, including foundations, sunscreen products, sunless skin tanning products, hair removal products, creams (e.g., moisturizing creams, burn creams, skin benefit creams, night creams, dermatological creams, etc.), serums, liquids, skin benefit lotions, softeners, gels, sprays, foams, soltions, soaps, shampoos, ointments, lipsticks, cleansers, toners, masks, hair products, finger nail products, as well as other cosmetic products or applications.

IV— Kits

According to another aspect of this invention, kits for forming a formulation for delivery of a bioactive agent are provided. The kits of the invention comprise a first aliquot portion of a concentrate solution, and a second aliquot portion of a carrier. When mixed, the first and second aliquot portions form a composition for delivery of the bioactive agent contained therein. A preservative may be incorporated into one of the first and second aliquot portions. The carrier is typically a dermatological, oral, injectable, or aerosol carrier.

The kits of the invention can advantageously be provided with a double syringe having first and second syringe barrels which respectively contain the first and second aliquot portions of the reaction mixture. A duel syringe set-up can be used in preparation of the formulations according to the present invention. For example a concentrate solution of a flavonoid, such as apigenin, can be contained within the barrel of one syringe, while a carrier can be contained within the barrel of the other syringe. The syringes are connected to one another so that the contents can be mixed by alternately transferring the mixture from one syringe barrel to another for about 30 cycles. The concentrate solution is stable for at least one year and the carrier stable for at least that time, in some cases indefinitely. Maintenance of sterility, broad applicability, stability of the bioactive agent and ease of use are the attributes of such a double syringe system.

V—Uses of the Compounds and Formulations of the Invention

Flavonoids

Flavonoids have multiple therapeutic applications since they are free radical scavengers, anti-oxidants, superoxide anions, UV absorbers, vasodialators, anti-hyaluronidase (inhibits breakdown of hyaluronic acids by inhibiting hyaluronidases), anti-collagenase (inhibits breakdown of collagen by inhibiting collagenases), anti-elastase (inhibits breakdown of elastin by inhibiting elastases), and scavaging lipid peroxide radicals. Flavonoid compounds are also known to be effective in strengthening collagen structures. Further, flavonoids have anti-mutagenic, anti-angiogenic, anti-carcinogenic, anti-inflammatory, antibacterial and antiviral effects. The anti inflammatory effects include inhibition of TNF-alpha, IL-beta, COX-2, protein kinase PKC, iNOS, and T helper cells Th 1 and Th 17. Flavonoids, apigenin in particular, is a stimulator of p53. Researchers have found that apigenin induces reversible, cell-cycle arrests at G1 and G2/M phase of the cell cycle.

Flavonoids alone or in combination with other preventive and/or therapeutic effective drugs, are effective in treating or preventing in mammals, including humans, the most common diseases such as cancer, autoimmune disease, diabetes, ulcer, cardiovascular disease, atherosclerosis, and liver disease. The compounds also have antithrombogenic activity.

Skin Diseases

This disclosure provides methods for making topical formulations containing flavonoids, such as apigenin, at a pharmaceutically meaningful concentration in a dermatologically acceptable pH range. The flavonoids are in dissolved form. The topical application formulation can be a composition in the form of a gel, ointment, solution, lotion, cream, spray, dermal patch, transdermal patch and so forth, so as to deliver sufficient flavonoid into mammalian (such as human) tissue (e.g., into mammalian keratinous tissue).

Topical Application Amount

A typical topical dose ranges from 1 to 10 mg/cm$^2$, preferably 1 to 5 mg/cm$^2$ and most preferably from 1 to 3 mg/cm$^2$. The dosage varies according to condition and mode of administration The topical dose used in FDA sunscreen topical testing is 2 mg/cm$^2$ of formulation applied to exposed skin. "Re: Tentative Final Monographfor OTC Sunscreen", Food and Drug Administration (U.S.). 1998-09-11. Retrieved 2009-09-25 Provided one assumes an "average" adult build of height 5 ft 4 in (163 cm) and weight 150 lb (68 kg) with a 32 in (82 cm) waist, that adult wearing a bathing suit covering the groin area should apply 29 g (approximately 1 oz) evenly to the uncovered body area. Considering only the face, this translates to about ¼ to ⅓ of a teaspoon for the average adult face. Larger individuals should scale these quantities accordingly.

In terms of the amount of topical medication that generally should be applied to affected skin, dermatologists refer to the "fingertip unit" as the recommended guidance. One fingertip unit is the amount of topical formulation that is squeezed out from a standard tube along an adult's fingertip. One fingertip unit is approximately 500 mg of formulation (tube with a standard 5 mm nozzle), and recommendations for the number of units needed to cover affected areas are offered. For example, three fingertip units are required to adequately cover psoriasis on the scalp, whereas eight fingertip units are needed for the entire leg and foot. This method provides a means for patients to more accurately dose their topical medications.

Prevention and Treatment of Skin Damage Due to Solar Radiation

Soluble forms of the flavonoid, e.g. apigenin and/or luteolin, can readily penetrated into and be absorbed by the skin to prevent damage (photoaging) or to repair the skin matrix that has been damaged. As shown in Example 15 below, the formulations of the subject invention allow significant skin penetration of the flavonoid.

The low solubility of apigenin and/or luteolin in the excipients typically comprising lotions and creams makes formation of such compositions with desired amounts of flavonoid in solution difficult. In one embodiment, the formulation contains a sufficient amount of solubilized flavonoid at a nearly neutral pH to penetrate into the living skin matrix to minimize or eliminate skin tissue damage to protect living skin from damage caused by exposure to UV rays and/or pre-penetrate. The topical formulations can be administered to an individual, preferably by topical application to the skin of the individual, orally (e.g., as a food supplement), etc. The formulations can be administered in an amount effective to prevent UV damage, e.g., to inhibit free radicals, reactive oxygen species, and/or other oxidizing species.

With respect to its anti skin cancer activities, apigenin acts effectively even in very low concentrations, <about 50 µM. Apigenin exhibits antiproliferative and cytotoxic effects by affecting apoptosis and necrosis mechanisms during cell proliferation and angiogenesis that are the major characteristics of a variety of cancer cells including prostrate cancer, breast cancer, lung cancer, leukemia, thyroid cancer and liver cancer, resulting in the inhibition of proliferation of cancer cells.

Mechanism

The primary mechanisms of flavonoids, e.g. apigenin, are believed to be their capability to increase the stability of p53; thereby inducing both G1 and G2/M cell cycle arrests and its well documented anti-inflammatory, anti-oxidant, nontoxic, and non-mutagenic properties. These cell cycle arrests are fully reversible after removal of apigenin by washing or its diffusion out of the skin.

In light of the fact that apigenin causes both G1 and G2/M cell cycle arrests, the essence of apigenin's chemopreventative activity may be to inhibit cancer initiation and progression by ensuring that sufficient intrinsic and artificially imposed cell cycle checkpoints exist in the presence of DNA damaging and tumor promoting agents. Apigenin and luteolin treatment of skin prior to sunlight exposure may extend the time cells normally arrest in G1 and G2/M in response to DNA damage. These flavones increase the duration of the G1 phase beyond that which occurs in normal cells in response to DNA damage, or alternatively, these flavones retard cells containing an activated oncogene in G1 when otherwise cell cycle progression would continue even in the presence of substantial DNA damage. Hence, the time spent in G1 and G2/M is critical for cells to efficiently repair all DNA mutations, and thus slow or prevent the carcinogenic process.

Since the effects of sunlight damage are cumulative over a lifetime, the tumor suppressor protein p53, which is the most commonly mutated gene in all human and animal cancers, may already be inactivated in some keratinocytes by the time a person uses a topical application of apigenin and/or luteolin. Since the effects of these flavones are p53-dependent on the G1 arrest and p53-independent on G2/M arrest, in instances where keratinocytes already have an inactivated p53 gene, apigenin will bolster the G2/M arrest in these small foci of premalignant cells in order to prevent additional mutations, translocations, and/or chromosome loss during mitosis. In addition, apigenin and/or luteolin may exert its protective effects by scavenging free radicals generated in response to UV-B/A sunlight irradiation.

It is believed that apigenin treatment can enhance the apoptotic response initiated by UVB. Without being bound by theory, it is believed that the chemo-preventive action of apigenin is explained by its ability to enhance UV-induced apoptosis by significantly increasing the stability of p53 which is a prime factor in the skin cancer apoptosis process. Therefore, there is a need to deliver apigenin into the viable epidermis or the whole skin layer at a pharmaceutically meaningful concentration in order to be effective in skin cancer prevention. (Li B.; Birt D. F.; Pharmaceutical, Volume 13, Number 11, November 1996, pp. 1710-1715(6))

As disclosed herein, a composition for the topical application containing flavonoids, particularly apigenin and/or luteolin, is useful for the prevention and/or treatment of skin damage ansing from exposure to solar radiation (UVA and/or UVB). Apigenin and/or luteolin compositions also augment the efficacy of other ingredients in topical compositions for sunburn prevention and treatment.

In use, the product can be used in single or multiple applications to attain the desired results. In some embodiments, the sunscreen ingredients can be part of the formulation, and/or can be applied as a secondary application such that a film containing the sunscreen ingredients serves to provide additional full spectrum UV radiation protection by blocking or reflecting UV radiation.

Since apigenin and luteolin function intracellularly on the cell cycle, either could be combined with other sunscreen agents that function simply as a barrier on the outside of the cell to absorb, block or reflect UV energy in sunlight. Thus, topical application of apigenin and/or luteolin, reversible cell cycle regulators, represents a useful and novel approach for skin cancer prevention and can be used sequentially or in combination with currently marketed topical sunscreen products.

These flavonoids are exceptionally beneficial as additives to topical formulations for their anti-oxidant, anti-inflammatory, UV skin protection and other desirable properties. Thus, topical application of apigenin and luteolin represent a useful and novel approach for skin cancer prevention/treatment and could be used prior to or in combination with currently marketed topical sunscreen products.

Not to be limited by theory, it is believed that the formulations can be employed, for example, to treat or prevent skin cancers caused by exposure to ultraviolet (UV) light or sunlight.

Disclosed herein are compositions containing flavonoids or topical applications for the prevention and/or treatment of skin cancer and other topical cancers including but not limited to cervical and breast cancer. The composition contains pharmaceutically sufficient amount of apigenin to penetrate into the skin layer, e.g., to increase the stability of p53 to prevent and treat skin and other topical cancers.

It is believed that the UVB photo-protective effects of the antioxidant apigenin and luteolin are significant when applied in distinct mixtures in appropriate vehicles. Flavonoid(s) together with other ingredients provide a natural approach to efficiently supporting the body's own defense mechanism in providing protection from sunburn and chronic UV damage. The natural antioxidant properties and anticancer properties of apigenin and/or luteolin combined with mineral pigments provide a synergistic, photo-protective effect to reduce the risk of UV damage and skin cancer. The other natural ingredients including antioxidants such as vitamin E and moisturizes can be added to create a synergy that enhances UV protection and also soothes the skin.

Also disclosed herein are methods of reducing and/or preventing the effects of sun exposure which can comprise: applying a topical formulation comprising a flavonoid and a dermatologically acceptable carrier to permit delivery of the flavonoid components to mammalian keratinous tissue. Optionally, the topical cosmetic composition can be applied a second time, a third time, or more.

Cancer

Three ideal qualities of a cancer chemopreventative agent are: 1) that it is a natural compound present in foods known to be associated with reduced cancer incidence; 2) that it has a known mechanism of action; and 3) that the effects are reversible. It is believed that flavonoids such as apigenin and luteolin satisfy all three criteria.

The formulations of the invention can be used for cancer prevention as well as cancer treatment. The formulations are useful for the treatment or prevention of skin cancers (including actinic keratosis, melanoma, basal cell carcinoma), ovarian cancer, cervical cancer, prostate cancer, breast cancer, lung cancer, leukemia, thyroid cancer, liver cancer and brain cancer including neuroblastoma.

Methods of Treatment of Other Skin Disorders

The compounds and formulations of the invention are useful for the treatment of psoriasis. Example 15 demonstrates that topical formulations penetrate human skin in a concentration sufficient to be of therapeutic value.

Additional dermatological disorders and related afflictions/conditions that can be treated or prevented by the topical use of the formulations and compositions of this invention include, but are not limited to the following: acne, alopecia, atopic dermatitis/eczema, cutaneous lupus erythematosus, dermal sensitization and irritation, dry skin (xerosis, ichthyosis), fungal infections, and rosacea, contact dermatosis, autoimmune afflictions including psoriasis, and arthritis. The topical administration of apigenin/flavonoids allows excellent bioavailability. Hence, these topical formulations are alternatives to costly and less desirable steroids and cytotoxic drugs.

Methods of Treatment of Other Disorders

The compounds, compositions and formulations of the invention can also be used for the treatment of other autoimmune disease such as lupus, arthritis, allergies and asthma. Flavonoid formulations of the invention represent new adjuvant therapeutics with efficacy in autoimmune disease. The bioavailability of dietary plant-derived COX-2 and NF-kB inhibitors, such as apigenin is valuable for suppressing inflammation in lupus and other Th17-mediated diseases like rheumatoid arthritis, Crohn's disease, and psoriasis, and in prevention of inflammation-based tumors overexpressing COX-2 (e.g. colon, breast). Apigenin suppresses lupus by inhibiting autoantigen presentation for expansion of autoreactive Th1 and Th17 cells. The formulations of this invention offer a novel means of delivering apigenin/flavonoids for the treatment of autoimmune indications/diseases. The administration can be as an adjunct to other autoimmune therapies such as an anti-TNF antibody (e.g. for psoriasis or for rheumatoid arthritis).

The compounds and formulations are also useful for the treatment of neurological and neurodegenerative disorders. Several research studies have provided support for apigenin and luteolin's anti-inflammatory effects and their neuroprotective/disease-modifying properties in various neurodegenerative disorders, including Alzheimer's disease.

In another embodiment, the compounds and compositions of this invention are useful for the treatment of allergic diseases as well as bacterial infections.

Examples of the TNFα related conditions that can be treated, prevented or ameliorated with the flavonoids of the invention include, but are not limited to, rheumatoid arthritis, juvenile rheumatoid arthritis, osteoarthritis, spondyloarthropaties, inflammatory bowel disease, chronic heart failure, diabetes mellitus, systemic lupus erythematosus, scleroderma, sarcoidosis, polymyositis/dermatomyositis, psoriasis, multiple myeloma, myelodysplastic syndrome, acute myelogenous leukemia, Parkinson's disease, AIDS dementia complex, Alzheimer's disease, depression, sepsis, pyoderma gangrenosum, hematosepsis, septic shock, Behcet's syndrome, graft-versus-host disease, uveitis, Wegener's granulomatosis, Sjogren's syndrome, chronic obstructive pulmonary disease, asthma, acute pancreatitis, periodontal disease, cachexia, cancer, central nervous system injury, viral respiratory disease, and obesity.

Examples of the IL-1β related conditions to be treated, prevented or ameliorated with the flavonoids of the invention include, but are not limited to, rheumatoid arthritis, hematosepsis, periodontal disease, chronic heart failure, polymyositis/dermatomyositis acute pancreatitis, chronic obstructive pulmonary disease, Alzheimer's disease, osteoarthritis, bacterial infections, multiple myeloma, myelodysplastic syndrome, uveitis, central nervous system injury, viral respiratory disease, asthma, depression, and scleroderma.

Due to the inhibitory activity of flavonoids on IL-4 and IL-13 synthesis, it can be expected that the intake of flavonoids, depending on the quantity and quality, can ameliorate allergic symptoms or prevent the onset of allergic diseases. (*Int Arch Allergy Immunol.* 2004 June; 134(2): 135-40.)

Apigenin possesses anti-inflammatory activity in human periodontal ligament (hPDL) cells and works through a novel mechanism involving the action of heme oxygenase-1 (HO-1) 1. Thus, apigenin has benefits as a host modulatory agent in the prevention and treatment of periodontal disease associated with smoking and dental plaque. (Gil-Saeng Jeong et al.; *Anti-inflammatory effects of apigenin on nicotine-and lipopolysaccharide-stimulated human periodontal ligament cells via heme oxygenase-l., International Immunopharmacology*, Vol.: 9, November 2009).

In another embodiment, the compounds and formulations of this invention can be useful for promoting hair growth. Research studies teach that the apigenin stimulates hair growth through downregulation of the TGF-beta1 gene.

The formulations of this invention are also useful in the treatment and prevention of arteriosclerosis.

Other Active Agents

Formulations made using the methods of the invention of the compounds note in Section I above "Compounds of the Invention" can be used for the indications (uses) specified or known for those compounds. For example, a formulation of camptothecin made using polysorbate as in the subject invention, can be used in the treatment of cancer.

EXAMPLES

Example 1. Solubility in Polysorbates

The Apigenin and Polysorbate 80 resulting product is referred to as "A/PS80". A/PS80 was formed as follows:
The unprocessed apigenin powder & viscous liquid polysorbate 80 (PS80) were mixed in the ratio from about 5 to 10 wt % of apigenin to 95 to 90 wt % polysorbate 80 and a small quantity of D.I. water and optionally acetone and/or ethyl alcohol in a beaker.
This mixture was then thoroughly stirred to form a thick paste-like blend.
The mixture was then slowly heated to relatively high temperatures while stirring. The heating was accompanied by the boiling off of the water and also volatile constituents present in the polysorbate 80. The heating process was conducted with care to avoid the mixture overflowing from the beaker due to foaming resulting from the heating process.
Upon the removal of the volatiles and heating to temperatures in excess of about 200 to 300° C., a dark brown transparent liquid resulted such that all the solid apigenin is solubilized in the polysorbate 80 mixture.
Upon cooling to ambient temperatures, a viscous brown clear liquid resulted. The higher the apigenin content— the darker the resulting color). Addition of a few crystals of apigenin to the cooled A/PS80 liquid did not result in precipitation; thereby demonstrating that the A/PS80 liquid is not supersaturated.

According to the published solubility results shown in the Table VII the solubility of apigenin in water, ethyl alcohol and Span 80 are listed as follows: (Ref Li et al, *J of Pharm Sci*, Vol. 86, No. 6, June 1997).

TABLE VII

| Solubility of Apigenin @ 25° C. | | |
|---|---|---|
| | SOLUBILITY | |
| SOLVENT | (mg/ml) | (ppm) |
| Water | 0.00135 | 1.35 |
| Ethyl Alcohol | 1.65 | 1,630 |
| Span 80 | 0.15 | 150 |

The concentration of apigenin in A/PS80 was measured by HPLC-MS. Based measured the concentration of apigenin in A/PS80 on the calculated value of 4.05% concentration of apigenin in the viscous A/PS80 liquid; the content of apigenin is 40.5 mg/ml or 40,500 ppm.

The following paragraphs list experimental observation attributable to A/PS80.

The addition of A/PS80 to the standard hydrated apigenin lotions (which contain a substantial concentration of nanoparticulates) contributed to an enhancement in saturation soluble concentration levels. The enhanced solubility level was qualitatively determined via colorimetric testing performed on filtrate liquids passing through a 0.2 micron filter.

Addition of A/PS80 to Purell (the widely used bactericidal fluid) resulted in an appreciable apigenin soluble level attributable to the high ethyl alcohol content of Purell. The soluble apigenin levels achieved with polysorbate 80 were significantly greater than both hydrated apigenin and unprocessed apigenin.

Experiments where A/PS80 was added to Purell followed by the application of the apigenin lotion worked quite well. The idea was to take advantage of ethyl alcohol's favorable penetrating and solubility properties (note that ethyl alcohol will evaporate shortly after application which will tend to dry out the skin) followed by the application of our apigenin formation to assist in skin re-hydration.

The concentrations of apigenin in weight % for selected solvents as determined by LCMS (Liquid Chromatography-Mass Spectroscopy) shown in Table VIII.

TABLE VIII

APIGENIN ANALYTICAL SUMMARY IN SELECTED SOLVENTS

| SAMPLE DESCRIPTION | SOLUBLE APIGENIN CONCENTRATION (% Wt/Wt) - (mg/ml) |
|---|---|
| Apigenin/PS80 added to Purell Lotion | 0.52%-5.2 mg/ml |
| Apigenin/PS80 added to Ethyl Alcohol Rubbing Solution | 0.91%-9.1 mg/ml |
| Apigenin/PS80 (Concentrated Stock Solution) | 4.05%-40.5 mg/ml |

Additional testing verified that essentially there was insignificant decomposition products resulting as a consequence of heating PS80 with apigenin to elevated temperatures approaching 250-300° C.

FIG. 2 shows a statistical analysis of PS 80 prior to heating as compared to the A/PS80 solution. Insignificant differences were observed between the control sample and the invention sample showing that the surfactant had not degraded. In FIG. 2, each component detected is represented by a dot. PS80 is a polymer and as such, shows many oligomers. This explains the large number of components or dots on the plot. The Xs are indicative of mass features which are distinct to the A/PS80 sample statistically. Very few distinct features were observed indicating that the PS80 did not significantly degrade. The presence of an only a few Xs indicates few differences between the control and invention samples.

Example 2. Solubility of Selected Flavonoid Concentrates in Polysorbate 80 and PEG 400 as Determined by HPLC The objective of this work was to quantify a total of six different flavonoids in PS80 and PEG-400. The samples were also analyzed qualitatively to look for signs of degradation of the solvents due to the elevated temperatures required of the thermal treatment process.

This project was divided into three distinct phases: method validation/development, quantitation of the individual flavones, and qualitative analysis to look for signs of PS80/PEG400 degradation. Method development was performed to determine the suitability of a previously used HPLC method for Apigenin for the remaining flavonoids to be quantified in either PEG400 or PS80.

Table IX provides the HPLC measured flavonoid concentration in the as-prepared flavonoid concentrates formulated by the thermal treatment process in both PS80 and PEG-400.

TABLE IX

Flavonoid Analytical Summary In Selected Solvents

| Flavonoid | Solvent | Flavonoid in Solvent - (mg/ml) |
|---|---|---|
| Quercetin | PS80 | 65.0 |
| Resveratrol | PS80 | 127.5 |
| Rutin | PS80 | 14.3 |
| Luteolin | PEG-400 | 72.5 |
| Apigenin | PEG-400 | 34.8 |
| Hesperidin | PEG-400 | 81.0 ± 8.0 |

Statistical Analysis software was used to look for the presence of unique features in the various flavonoid samples of Table IX when compared to the control PS-80 and PEG-400 reference materials. Liquid Chromatography Mass Spectroscopy (LCMS) was used to determine PS80 and PEG-400 degradation products. The number of unique components in each sample ranged from 12 in the Hesperidin-PEG-400 sample to 55 in the Apigenin-PEG-400 sample. A small number of unique components was expected due to the addition of the flavonoid and any trace components introduced with the flavonoid. Thus, the low number of unique components indicates that no appreciable degradation occurred.

Example 3. Additional Flavonoid Polysorbate Formulations

In addition to apigenin, testing with Polysorbate 80 was expanded to include several flavonoid compounds. Table X includes the chemical and physical property data of the flavonoids selected for solubility testing with Polysorbate 80.

TABLE X

SUMMARY OF CHEMICAL & PHYSICAL PROPERTIES OF FLAVONOIDS TESTED

| COMPOUND | MW | MP (° C.) | WATER SOLUBILITY (mg/ml) | PARTIAL LISTING OF FLAVONOID SOURCES | APPEARANCE |
|---|---|---|---|---|---|
| APIGENIN | 270 | ~360 | * 0.00002 (>Sol. In alcohol) | Parsley, Thyme, Celery, Chamomile | Yellow Crystalline Powder |
| LUTEOLIN | 286 | ~330 | * 0.38 mg/ml (>Sol. In alcohol) | Celery, Oregano, Thyme, Chamomile | Yellow Powder |
| RESVERATROL | 228 | ~255 | * 0.1 to 0.3 mg/ml 50 mg/ml in alcohol | Red Grapes & Red Wine, Peanuts, Some Berries | White Powder with a slight yellow cast |
| QUERCETIN | 302 | ~315 | * <1 mg/ml | Apples, Tea, Citrus, Broccoli, Berries | Yellow Crystalline Powder |
| HESPERIDIN | 610 | ~260 | * Values cited from 0.05 to 3 mg/ml | Buckwheat, Citrus, Cherries, Grapes | White to Yellow Powder |
| RUTIN | 610 | ~242 | * 0.07 mg/ml | Buckwheat, Citrus, Berries, Tea | Yellow to Green Powder |

* saturation concentrations solubility varied depending on published sources

Table XI contains a summary of the Polysorbate 80 solubility testing results with a variety of flavonoids.

TABLE XI

SUMMARY OF FLAVONOID TESTING WITH PS80

| COMPOUND | PS80 SOLUBILITY COMMENTS | SOLUBLE CONC. RANGE (% wt/wt)/ (mg/ml) |
|---|---|---|
| APIGENIN | 1. Thermal Treatment method. (Noted in Example 1) | 1. 4-6%/ (40-60 mg/ml) |
| LUTEOLIN | 1. Thermal Treatment method. | 1. >8% (>80 mg/ml) The upper sol. limit was not determined. |
| | 2. Luteolin in H2O & PS80 slurry was boiled resulting in solubilizing luteolin but to << extent than the Thermal Treatment Method | 2. Up to ~5% (~50 mg/ml) |
| RESVERATROL | 1. Thermal Treatment method | 1. >8% (>80 mg/ml) |
| | 2. The H2O boiling method utilized for Luteolin did not dissolve Resveratrol. | 2. Dissolution not detectable |
| QUERCETIN | 1. Thermal Treatment method | 1. >7% (>70 mg/ml) The upper sol. limit was not determined. |
| | 2. Quercetin in H2O & PS80 slurry was boiled resulting in solubilizing quercetin but to << extent than the Thermal Treatment method. | 2. <<7% |
| HESPERIDEN | 1. The Thermal Treatment Method resulted in a slight amount of a gray-colored precipitate which was removed by filtration with a 0.2 micron filter. | 1. ~<2% (~<20 g/ml) Decomposition |
| | 2. A 5% Hesperidin to PS80 ratio added to water. The mixture was boiled to form solubilized Hesperidin. No evidence of the "enhanced aqueous solubility" was noted. | 2. ~<1% (~<10 mg/ml) |
| RUTIN | 1. The Thermal Treatment Method resulted in a slight amount of a gray-colored precipitate which was removed by filtration with a 0.2 micron filter. | 1. ~<1% (~<10 mg/ml) |
| | 2. A 5% Rutin to PS80 ratio added to water. The mixture was boiled to form solubilized Rutin. No evidence of the "enhanced aqueous solubility" was noted. | 2. ~<0.5% (~<15 mg/ml) |

Example 4. Solubility in Polysorbates Other than Polysorbate 80 Via the Elevated Temperature Processing Method Non-ionic surfactants are extensively used in cosmetics and foods because they are considered to be harmless because they are fatty acid esters of polyalcohol such as sorbitan, sucrose, and glycerin. Consequently, it was decided to evaluate a number of suitable nonionic polysorbate structured surfactants to enhance the saturation solubility concentration via the high temperature processing methods disclosed in Example 1.

Table XII lists several nonionic surfactants consisting of PEG-ylated sorbitan (a derivative of sorbitol) esterified with fatty acids. All surfactants tested were oily liquids which satisfied the criteria of remaining stable at temperatures >200° C. Similarly, all tested flavonoids including apigenin were selected on the basis of having poor solubility properties.

It was observed that the flavonoid slurry mixture changes in both particulate solubility and color (a dark brown-red) was observed when temperature levels exceeded 200 to 300° C. Addition of a few crystals of the apigenin to the cooled liquid did not result in precipitation; thereby demonstrating that the liquid is not supersaturated.

The nonionic surfactants listed in Table XII are arranged in order of ascending (Hydrophile-Lipophile Balance) HLB values. HLB is an empirical expression for the relationship of the hydrophilic ("water-loving") and hydrophobic ("water-hating") groups of a surfactant. The higher the HLB value, the more water-soluble is the surfactant. The majority are lotions (oil-in-water emulsions) or creams (water-in-oil emulsions). The most common emulsion type, oil-in-water (o/w), often requires higher HLB surfactants—preferably 12-16 while water-in-oil emulsions (w/o) require low HLB surfactants—preferable 7-11. Surfactants with an HLB value <10 are oil soluble while those >10 are soluble.

As noted in Table XII, Span 20 is very suitable for water-in-oil topical formulations while Polysorbate 80 would be most appropriate for solubilizing apigenin in oil-in-water topical formulations.

TABLE XII

A Summary of Apigenin Solubility in Nonionic Surfactants via the High Temperature Processing Method

| NONIONIC SURFACTANTS | CHEMICAL NAME | High Temp. Apigenin Solubility (mg/ml) | Apigenin Literature Solubility @ (° C.) - (mg/ml) | HLB VALUE | USES |
|---|---|---|---|---|---|
| Span 80 | Sorbitan monostearate | ~8 | 0.15 | 4.3 | Foods, beverages, Pharmaceuticals |
| Span 20 | Sorbitan monolaurate | ~10 | 0.17 | 8.6 | Foods, beverages, Pharmaceuticals |

TABLE XII-continued

A Summary of Apigenin Solubility in Nonionic Surfactants via the High Temperature Processing Method

| NONIONIC SURFACTANTS | CHEMICAL NAME | High Temp. Apigenin Solubility (mg/ml) | Apigenin Literature Solubility @ (° C.) - (mg/ml) | HLB VALUE | USES |
| --- | --- | --- | --- | --- | --- |
| Nonoxynol-9 | Polyoxyethylene nonyl phenyl ether | ~30 | — | 13.0 | Disinfection, spermicide, cosmetics |
| Polysorbate 60 | Polyoxyethylene (20) sorbitan monostearate | ~15 | — | 14.9 | Foods, beverages, Pharmaceuticals |
| Polysorbate 80 | Polyoxyethylene (20) sorbitan oleate | ~50 | — | 15.0 | Foods, beverages, Pharmaceuticals |
| Polysorbate 20 | Polyoxyethylene (20) sorbitan monolaurate | ~25 | — | 16.7 | Foods, beverages, Pharmaceuticals |
| *Propylene Glycol | — | ppt. est. ~1 | 1.0 | — | Foods, beverages, pharmaceuticals |

Note:
*Not a surfactant

Example 5. The Solubility of Active Agents in PS80 and PEG 400 Via the Thermal Treatment Method A study was undertaken to investigate the potential aqueous solubility enhancement of active agents dissolved in PS80 and PEG 400 by means of the disclosed thermal treatment process.

Table XIII briefly summarizes solubility results of 4 active agents employing the disclosed thermal treatment process to form concentrates that resulted in the enhancement of aqueous solubility of several relatively insoluble flavonoids.

TABLE XIII

A Summary of the Active Agent/Surfactant Testing Utilizing the Thermal Treatment Process

| ACTIVE AGENT COMPOUND | USAGE | MW | MP (° C.) | PS80 Solubility—Results/ Comments | PEG400 Solubility—Results/ Comments |
| --- | --- | --- | --- | --- | --- |
| Mefenamic acid 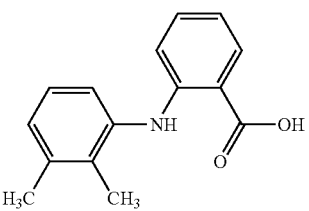 | Pain Relief/ NSAID | 241 | 230 | 1 wt % solubilized in PS80 @ ~140° C. & remained solubilized @ Room Temp. [(1)]Not Sup.Sat. Most Mefenamic Acid dissolved when H$_2$O was added to 1 wt. % solution. | 1 wt % solubilized in PEG400 @ ~140° C. & remained solubilized @ Room Temp. [(1)]Not Sup.Sat. Most Mefenamic Acid ppt. out when H$_2$O was added to 1 wt. % solution. |
| Diclofenac Sodium 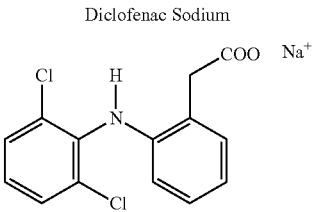 | Pain Relief/ NSAID | 318 | 283 | 5 wt % solubilized in PS80 @ ~200° C. & remained solubilized @ Room Temp. [(1)]Not Sup.Sat. Diclofenac Sodium remained clear when H$_2$O was added to the 10 wt % Sol.—(pH ~7). Adding citric acid sol. to a pH ~4 pptd. diclofenac sodium. | 5 wt % solubilized in PEG400 @ ~100° C. & remained solubilized @ Room Temp. [(1)]Not Sup.Sat. Diclofenac Sodium remained clear when H$_2$O was added to the 10 wt % Sol.—(pH ~7). Adding citric acid sol. to a pH ~4 pptd. diclofenac sodium. |

TABLE XIII-continued

A Summary of the Active Agent/Surfactant Testing
Utilizing the Thermal Treatment Process

| ACTIVE AGENT COMPOUND | USAGE | MW | MP (° C.) | PS80 Solubility—Results/Comments | PEG400 Solubility—Results/Comments |
|---|---|---|---|---|---|
| Diclofenac Acid 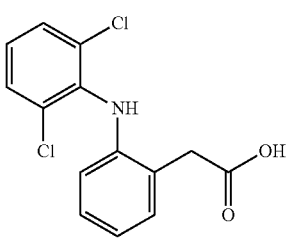 | Pain Relief/ NSAID | 296 | 177 | 4 wt % solubilized in PS80 @ ~140° C. & remained solubilized @ Room Temp. [1]Not Sup.Sat. Diclofenac Acid remained clear when $H_2O$ was added to the 10 wt % Sol.—(pH ~7.5). A clear sol. remained after citric acid sol. added to a pH ~4 | 4 wt % solubilized in PEG400 @ ~140° C. & remained solubilized @ Room Temp. [1]Not Sup.Sat. Diclofenac Acid pptd. when $H_2O$ was added to the 4 wt % Sol.— (pH ~7.5). |
| Fluorouracil 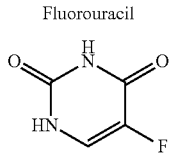 | Anti Cancer/ Keratosis | 130 | 282 | 10 wt % solubilized in PS80 @ ~200° C. & remained solubilized @ Room Temp. [1]Not Sup.Sat. Fluorouracil remained clear when $H_2O$ was added to the 5 wt % Sol.—(pH ~7). A clear sol. remained after citric acid sol. added to a pH ~4 | 10 wt % solubilized in PEG400 @ ~175° C. & remained solubilized @ Room Temp. [1]Not Sup.Sat. Fluorouracil remained clear when $H_2O$ was added to the 5 wt % Sol.—(pH ~7). A clear sol. remained after citric acid sol. added to a pH ~4 |

Note:
[1]The solution was not supersaturated as determined by the addition of a crystal such the precipitation did not occur.

The results of this study indicated that the thermal treatment process is useful to improve solubility, dissolution rate, and subsequently, bioavailability of poorly soluble drugs.

Example 6. Solubility in Ceteareth-20 Via the Elevated Temperature Processing Method Solubility testing with Ceteareth-20, a nonionic surfactant, and the flavonoids, apigenin, luteolin and quercetin, were subjected to the thermal treatment process to investigate the likelihood of solubility enhancements in aqueous solutions.

Ceteareth-20 (CAS #68439-49-6) was obtained from Making Cosmetics.com, Inc located in Renton, Wash. Ceteareth-20 is a polyoxyethylene ether of higher saturated fatty alcohols (cetyl/stearyl alcohol). At room temperature, Ceteareth-20 is a solid, has no odor and melts at 40° C. Ceteareth-20 forms oil-in-water emulsions and has an HLB value ranging from 15-17.

For each of the flavonoid solubility tests, the following procedure was followed:
1. Weigh out 6.0 grams of the solid white Ceteareth-20 pellets in a 50 ml Pyrex container.
2. Heat the Ceteareth-20 pellets to a temperature slightly in excess of about 100° C. (The melting point of the pellets is about 40° C.)
3. Weigh out 0.06 gms of the flavonoid.
4. The flavonoid is added then added to the molten Ceteareth-20.
5. The mixture is slowly heat to temperatures in excess of 200° C. to completely solubilize the flavonoid/Ceteareth-20 mixture.
6. The solubilized mixture is cooled to <~80° C. and while still in the liquid state both water and alcohol solvents are added and solubility observations are noted. Also, supersaturation observations were noted by the addition of a crystal to note if precipitation resulted.

Table XIV summarizes the experimental observations of the thermally treated enhanced solubility observations. The ease of solution appears to be in the following order:

Quercetin>Luteolin>Apigenin

The 3 tested flavonoids required temperatures>200° C. to fully solubilize the 1 wt/wt % in Ceteareth-20. All flavonoid concentrated solutions were completely soluble in ethyl alcohol. Also, all flavonoids solutions were fully solubilized when each of the flavonoid/Ceteareth-20 solutions were mixed with an equivalent volume of water. Significant increased aqueous solubility concentrations of 3 relatively aqueous insoluble flavonoids in Ceteareth-20 resulted via the thermal treatment process.

TABLE XIV

A Summary of the Flavonoid/Ceteareth-20 Solubility Results

| FLAVONOID | MW | MP (° C.) | Conc. In Ceteareth-20 (mg/ml) | COMMENTS |
|---|---|---|---|---|
| APIGENIN | 270 | ~360 | ~10 | The least soluble of the tested Flavonoids. Required the highest temperature, >200° C., to solubilize the 1 wt/wt %. Not Super Saturated at Room Temp. via crystal addition. |
| LUTEOLIN | 286 | ~330 | ~10 | A small quantity dissolved at 100° C. A temperature of >200° C. required for compete solubilization. Not Super Saturated at Room Temp. via crystal addition |
| QUERCETIN | 302 | ~315 | ~10 | Temperatures >200° C. were required for complete solubilization. Not Super Saturated at Room Temp. via crystal addition. |

Example 7. Aqueous Solubility Comparisons of Aqueous Insoluble Planar Cyclic Organic Compounds in Polysorbate 80—with and without the Formation of Concentrates Via the Thermal Treatment Process Mefenamic Acid, Luteolin and Apigenin, aqueous insoluble planar aromatic compounds, were solubilized in Polysorbate 80 at elevated temperatures to form stable soluble concentrates that when cooled to ambient temperatures resulted in soluble concentrations that were not super saturated and far exceeded anticipated saturation concentrations. Testing for supersaturation was evaluated by the addition a crystal to the solution at room temperature. Water was added to these concentrates and their aqueous solution characteristics noted. For comparative purposes, the same quantities of ingredients in the concentrates were separately added to the same quantity of water prior to heating to near boiling. After cooling to room temperatures, visual observations of both the Polysorbate 80 concentrate and non-concentrate methods were compared.

When similar quantities of mefenamic acid, luteolin and apigenin and polysorbate 80 that were used to prepare the concentrate were added to 17 ml of water and heated to near boiling temperatures, opaque solutions were formed. When the solutions were cooled to ambient temperatures, most of the mefenamic acid, luteolin and apigenin did precipitate from the aqueous solutions.

The data on the order and manner in the mixing of polysorbate 80 with relatively aqueous insoluble cyclic organic compounds to enhance their solubility in aqueous solutions indicates that the compounds initially be heated and solubilized in polysorbate 80 to form a concentrate prior to being dissolved in water.

Example 8. Aqueous Solubility Comparisons of Relatively Aqueous Insoluble Planar Cyclic Organic Compounds in Nonoxynol-9—with & without the Formation of Nonoxynol-9 Concentrates Via the Thermal Treatment Process Solubility testing with nonoxynol-9, a commonly utilized nonionic surfactant in cosmetic and cleaning products, was studied as a solubilizing agent for the relatively aqueous insoluble planar aromatic compounds such as mefenamic acid (an active agent), luteolin (a flavonoid) in addition to apigenin. The mefenamic acid, luteolin and apigenin were solubilized in nonoxynol-9 at elevated temperatures to form stable soluble concentrates that when cooled to ambient temperatures resulted in soluble concentrations that were not supersaturated and exceeded anticipated saturation concentrations. The concentrates were added to water and their aqueous solution characteristics noted. For comparative purposes, the same quantities of ingredients in the concentrates were separately added to the same volume of water prior to heating to near boiling. After cooling to room temperatures, visual observations of both the concentrates and non-concentrate methods were compared.

Table XVI summarizes the results of the prepared nonoxynol-9 concentrations, the temperatures required for solubilization and observations relating to the clarity of the aqueous concentrate solutions.

TABLE XV

Polysorbate 80 Test Results|

| CHEMICAL | Classification | MW | MP- ° C. | Literature Solubility in $H_2O$ @ 25° C. (mg/ml) | Prepared Thermal Treatment Concentration in Polysorbate 80 (mg/ml) | Soln. Temp. (° C.) | Comments when 17 ml of $H_2O$ was added to 3 gms of the concentrate |
|---|---|---|---|---|---|---|---|
| MEFENAMIC ACID | Active Agent | 241 | 230 | 0.004 | 10 Not Super Sat. when cooled to Room Temp. | ~140 | A clear soln formed. |
| LUTEOLIN | Flavonoid (A Flavone) | 286 | 330 | 0.14 | 50 Not Super Sat. when cooled to Room Temp. | ~250 | A clear soln formed. |
| APIGENIN | Flavonoid (A Flavone) | 270 | 360 | 0.001 | 30 Not Super Sat. when cooled to Room Temp. | ~270 | A clear soln formed. |

TABLE XVI

Nonoxynol-9 Test Results

| CHEMICAL | Classification | MW | MP (° C.) | Literature Solubility in H₂O @ 25° C. (mg/ml) | Prepared Thermal Treatment Concentration in Nonoxynol-9 (mg/ml) | Soln. Temp. (° C.) | Comments when 17 ml of H₂O was added to 3 gms of the concentrate |
|---|---|---|---|---|---|---|---|
| MEFENAMIC ACID | Active Agent | 241 | 230 | 0.004 | 10 Not Super Sat. when cooled to Room Temp. | ~140 | A clear soln formed. |
| LUTEOLIN | Flavonoid (A Flavone) | 286 | 330 | 0.14 | 50 Not Super Sat. when cooled to Room Temp. | ~250 | A clear soln formed. |
| APIGENIN | Flavonoid (A Flavone) | 270 | 360 | 0.001 | 30 Not Super Sat. when cooled to Room Temp. | ~270 | A clear soln formed. |

When similar quantities of mefenamic acid, luteolin and apigenin and nonoxynol-9 that were used to prepare the concentrate were added to 17 ml of water and heated to near boiling temperatures, opaque solutions were formed. When the solutions were cooled to ambient temperatures, most of the mefenamic acid, luteolin and apigenin did precipitate from the aqueous solutions.

The data on the order and manner in the mixing of nonoxynol-9 with relatively aqueous insoluble cyclic organic compounds to enhance their solubility in aqueous solutions indicates that the compounds initially be heated and solubilized in nonoxynol-9 to form a concentrate prior to being dissolved in water.

Example 9. Cholesterol Solubility Tests

The rings of cholesterol are composed of saturated hydrocarbon rings because each corner of the ring is composed of a carbon atom, with two hydrogen atoms extending off the ring. The flavonoids are primarily composed of cyclic planar unsaturated aromatic rings while cholesterol contains cyclic planar saturated rings. Significantly, most steroids share the cholesterol ring structure.

Aqueous solubility testing of Cholesterol with the non-ionic surfactants PS80 and Nonoxynol-9 and the solvent PEG 400 via the formation of concentrates by the thermal treatment process and the non-concentrate method were conducted.

The materials used for this testing included:
Super-refined grades of PS80 and PEG 400 were obtained from Croda Inc of Edison, N.J.

Nonoxynol-9 was obtained from Spectrum Chemical, New Brunswick, N.J.

Cholesterol was obtained from Sigma-Aldrich, St. Louis, Mo., —with a purity of >99%.

Cholesterol properties and the concentrations of the prepared concentrates are summarized in Table XVII.

TABLE XVII

Cholesterol Test Results

| CHEMICAL | MW | MP ° C. | Literature Solubility in H₂O @ 25° C. (mg/ml) | Prepared Thermal Treatment Concentrate in PS80 (mg/ml) | Prepared Thermal Treatment Concentrate in Nonoxynol-9 (mg/ml) | Prepared Thermal Treatment Concentrate in PEG-400 (mg/ml) |
|---|---|---|---|---|---|---|
| Cholesterol | 387 | 150 | 0.0001 | 10 | 10 | 10 |

NOTE:
Cholesterol is listed as soluble in benzene, chloroform, ether, hexane, isopropyl myristate, acetone & methanol Cholesterol solubility testing in PS80, nonoxynol-9 and PEG 400 by initially forming concentrates of the solvents included the following steps:
  30 mg of Cholesterol was added to 2.97 grams of PS80, nonoxynol-9 and PEG 400 which were contained in separate 50 ml beakers
  The mixtures were heated about 120° C. and 80° C. for the PS80, nonoxynol-9 and PEG 400 compositions, respectively.
  Testing for supersaturation at room temperature was evaluated by the addition of a crystal to the solution to determine if precipitation occurred.
  Visual observations of the clarity of the Cholesterol aqueous solutions in PS80, nonoxynol-9 and PEG 400 after the addition of 17 ml of water to each of the concentrates were made more than 50 hours after cooling to room temperature.

The PS80 and nonoxynol-9 aqueous solutions of Cholesterol remained clear more than 50 hours after cooling the solutions to ambient temperatures. However, when the 17 ml of water was added to the Cholesterol/PEG 400 concentrate, a cloudy opaque solution resulted. It should be noted that after the addition of a few mls of water a clear solution resulted.

For comparative purposes, similar quantities of ingredients present in the Cholesterol concentrates were separately added to the same volume of water prior to heating to near boiling.

Aqueous solution testing included the following steps:

In separate 50 ml beakers, 30 mg of Cholesterol, and 17 ml of water were added to 2.97 grams of PS80, Nonoxynol-9 and PEG 400 which were contained in separate 50 ml beakers.

Each solution was heated to about 100° C. while mixing.

Visual observations of the clarity of each of the Cholesterol containing solutions were made after the solutions were cooled to room temperatures.

The PS80, Nonoxynol-9 and PEG 400 Cholesterol solutions resulted in opaque cloudy solutions.

This Example demonstrates that the compounds should be heated and solubilized in surfactants such as PS80 and nonoxynol-9 to form a concentrate, prior to the addition of water.

Example 10—Solubility Studies of Apigenin in Propylene Glycol and Ethylene Glycol Apigenin is known to be only sparsely soluble in hydrophilic and lipophilic surfactants tested (0.15-0.68 mg/ml) at 25° C. (Li et al., *Journal of Pharmaceutical Sciences*, Vol. 86, No. 6, June 1997). Since the thermal treatment methods of surfactants herein disclosed resulted in significantly enhanced aqueous and lipophilic phase solubility enhancements, it was decided to perform experiments to determine the solubility properties/characteristics of apigenin in polypropylene glycol (PG) and ethylene glycol (EG) which are surfactant solvents used as precursors to manufacture some of the surfactants evaluated above. Observations resulting from the exposure of apigenin solubilized in PG and EG were made.

Propylene Glycol is a colorless, nearly odorless, clear, viscous liquid with a faintly sweet taste, hygroscopic and miscible with water. PG is a solvent in many pharmaceuticals, including oral, injectable and formulations. It as is used as a humectant for many applications and as a moisturizer in medicines, cosmetics, food, toothpaste, shampoo, mouthwash hair care and tobacco products. Its boiling point is 188° C. and its molecular weight is 76 gm/mole. Propylene glycol is the base subunit comprising the polypropylene glycol surfactants (PPGs).

Propylene Glycol's structural formula is:

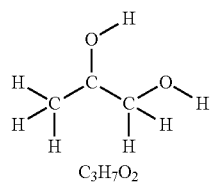

$C_3H_7O_2$

Ethylene glycol, is a colorless, oily liquid possessing a sweet taste and mild odor. Its molecular weight is 62 and its boiling point 197° C. Ethylene glycol is the base subunit comprising the polyethylene glycol surfactants (PEGs).

Ethylene glycol's structural formula is:

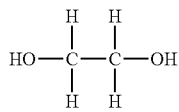

The solubility testing for both PG & EG were performed as follows:

In separate 18 ml vials, 200 mg of Apigenin was added to 4.80 gram of PG and also to EG. Both vials were heated to about 175° C. for the PG vial & to about 190° C. for the EG vial. Apigenin was completely solubilized in both vials to form 40 mg/ml solutions.

Upon cooling to room temperature, appreciable apigenin precipitation was observed for both PG and EG solutions. Thus demonstrating that these solutions were supersaturated.

The apigenin/PG and the apigenin/EG mixtures were then centrifuged for 20 minutes at 3,600 rpm; resulting in a pale yellow clear liquid and substantial fraction of precipitated apigenin that had separated out of both solutions.

In addition, after a few drops of water were added to the saturated solubilized apigenin/PG and EG solutions, a significant fraction of the solubilized apigenin precipitated out of both solutions thus limiting their usefulness for subsequent aqueous formulation development.

Example 11—Solubility of Flavonoid Surfactant and PEG 400 Concentrates in Oil Solvents The primary objective of this study was to evaluate enhancement of planar ring structured organic compounds solubility concentrations in oil. In general, nonionic surfactants are characterized by hydrophilic head groups that do not ionize appreciably in water. Examples include polyoxyethylenated alkylphenols, alcohol ethoxylates, alkylphenol ethoxylates, and alkanolamides. Nonionic surfactants tend to be good solubilizers and are relatively nontoxic. They are usually easily blended with other types of surfactants (i.e., used as cosurfactants) and therefore have found widespread use in cosmetic, pharmaceutical and environmental applications. The performance of nonionic surfactants, unlike anionic surfactants, is relatively insensitive to the presence of salts in solution.

The Hydrophile-Lipophile Balance (HLB) number is an indication of the relative strength of the hydrophilic and hydrophobic portions of the molecule and can be used to characterize the relative affinity of surfactants for aqueous and organic phases. A high HLB number generally indicates good surfactant solubility in water, while a low HLB number indicates a lower aqueous solubility and higher relative affinity for the organic phase. A surfactant with a low HLB number can partition significantly into the organic phase and form reverse micelles having hydrophilic interiors and lipophilic exteriors.

Polyglyceryl-4 Oleate (CAS #68605-19-6), nonionic surfactant with a HLB value of 5 suggests suitability for enhancing the solubility of planar ring structured organic compounds for oil based topical formulations while Polysorbate 80 as noted in Example 4 with an HLB value of 15 should be most appropriate for solubilizing apigenin in oil-in-water topical formulations.

Polyglycerol-4 Oleate obtained from Making Cosmetics (Renton, Wash.) is a distilled triyglcerol ester based on vegetable oleic acid and is PEG-free. It disperses in water and is well suited for water-in-oil emulsions). Borage oil was obtained from Sigma-Aldrich (St. Louis, Mo.) and Mineral Oil, USP, Canola Oil and Jojoba Oil from Spectrum Chemical of New Brunswick, N.J.

Tables XVIII, XIX & XX summarize visual observation when concentrates of luteolin in polyglcyeryl-4 oleate and apigenin in polysorbate 80 and PEG-400 were added to a variety of oils. It should be noted that luteolin and apigenin are insoluble in the test oils and that the 10 mg/ml luteolin concentrate in polyglcyeryl-4 oleate was not supersaturated at room temperature as determine by the absence of a precipitate upon the addition of a luteolin crystal to the luteolin/polyglcyeryl-4 oleate concentrate.

The lower HLB valued emulsifiers are better in water in oil as they are more lipophilic; the higher valued HLB emulsifiers are more hydrophilic

TABLE XVIII

Solubility Observations of a Luteolin/Polyglyceryl-4 Oleate Concentrate in Oils

| OIL | Observations when 1 ml of a 10 mg/ml Luteolin/ Polyglyceryl-4 Oleate Concentrate was added to 5 ml of Different Oils |
|---|---|
| Mineral Oil | Totally Miscible |
| Jojoba | Totally Miscible |
| Canola | Totally Miscible |
| Borage | Totally Miscible |

TABLE XIX

Solubility Observations of an Apigenin/Polysorbate 80 Concentrate in Oils

| OIL | Observations when 1 ml of a 30 mg/ml Apigenin/Polysorbate 80 Concentrate was added to 5 ml of Different Oils |
|---|---|
| Mineral Oil | The PS80 phase containing the solubilized Apigenin separated out from the Mineral oil phase - minimal solubilization of the PS80 phase in the Oil phase noted |
| Jojoba | Similar to the Mineral Oil Observations |
| Canola | Similar to the Mineral Oil Observations |
| Borage | Similar to the Mineral Oil Observations |

TABLE XX

Solubility Observations of an Apigenin/PEG-400 Concentrate in Oils

| OIL | Observations when 1 ml of a 30 mg/ml Apigenin/PEG-400 Concentrate was added to 5 ml of Different Oils |
|---|---|
| Mineral Oil | Two distinct clear phases resulted with the PEG-400 containing solubilized Apigenin settle out |
| Jojoba | Similar to the Mineral Oil Observations |
| Canola | Similar to the Mineral Oil Observations |
| Borage | Similar to the Mineral Oil Observations. |

Example 12. Capsaicin Solubility Tests

Aqueous solubility testing of capsaicin (a pain reliever) with the nonionic surfactants PS80 and the solvent PEG 400 via the formation of concentrates by the thermal treatment process and the non-concentrate method were compared.

The materials used for this testing included:
Super-refined grades of PS80 and PEG 400 were obtained from Croda Inc of Edison, N.J.
Capsaicin was obtained from Sigma-Aldrich, St. Louis, Mo., Product #360376.

Capsaicin properties and the concentrations of the prepared concentrates are summarized in Table XXI.

TABLE XXI

Properties of Capsaicin

| CHEMICAL | MW | MP (° C.) | Literature Solubility in $H_2O$ @ ° C. (mg/ml) | Prepared Thermal Treatment Concentrates in PS80 (mg/ml) | Prepared Thermal Treatment Concentrates in PEG-400 (mg/ml) |
|---|---|---|---|---|---|
| Capsaicin | 305 | 65 | <0.01 | 40 | 40 |

NOTE:
Merck lists Capsaicin as insoluble water but soluble in benzene, chloroform, ether, and alcohol.

Capsaicin solubility testing in PS80 and PEG 400 by initially forming concentrates using the thermal treatment method:
  30 mg of capsaicin was added to 2.97 grams of PS80 and PEG 400 which were contained in separate 50 ml beakers
  These mixtures were heated to about 50° C. while mixing.
  Addition of a few crystals of capsaicin to the cooled liquids did not result in precipitation; thereby demonstrating that these liquid is not supersaturated.
  Visual observations of the clarity of the capsaicin aqueous solutions in PS80 and PEG 400 upon the addition of 17 ml of water to each of the capsaicin concentrates were made after more than 50 hours subsequent to cooling to room temperature.
  A clear solution of the PS80 concentrate resulted after the addition of 17 ml of $H_2O$ and remained so more than 50 hours after the solution cooled to room temperature. However, a clear solution resulted after only the addition of a few mls of water (about 2 to 4 mls) to the capsaicin/PEG 400 concentrate which became opaque and cloudy with the addition of 17 ml of $H_2O$.

For comparative purposes, similar quantities of ingredients present in the Capsaicin concentrates were separately added to the same volume of water prior to heating to near boiling.

Aqueous solution testing included the following steps:
  In separate 50 ml beakers, 30 mg of capsaicin and 17 ml of water were added to 2.97 grams of PS80 and PEG 400 which were contained in separate 50 ml beakers.
  Each solution was heated to about 100° C. while mixing.
  Visual observations of the clarity of the capsaicin aqueous solutions in PS80 and PEG 400 subsequent to the addition of 17 ml of water to each of the capsaicin concentrates were made more than 50 hours after cooling to room temperature.
  The PS80 and PEG 400 capsaicin solutions resulted in opaque cloudy solutions.

This Example demonstrates that these compounds be heated and solubilized in surfactants such as PS80 to form a concentrate, prior to the addition of water.

Example 13. Coenzyme Q10, Polysorbate 80 and Jojoba Oil Solubility Testing

Since it was experimentally observed that the thermal process of forming concentrates (made from nonionic surfactants such as PS80 and a variety of organic compounds containing planar aromatic ring structures), is effective in enhancing aqueous solubility, solubility testing with CoQ10, a planar aromatic ring structured compound with good oil solubility, together with PS80 and an oil such as Jojoba, was conducted to provide additional data.

Coenzyme Q10, an oil-soluble vitamin-like substance, is present in most cells primarily in the mitochondria. It is a component of the electron transport chain and participates in aerobic cellular respiration, generating energy in the form of ATP. Ninety-five percent of the human body's energy is generated this way.

Jojoba oil is a mixture of wax esters, 36 to 46 carbon atoms in length. Each molecule consists of a fatty acid and a fatty alcohol joined by an ester bond. 98% of the fatty acid molecules are unsaturated at the 9th carbon-carbon bond.

Jojoba oil, Coenzyme Q10 and polysorbate 80 were obtained were obtained from Making Cosmetics, Renton, Wash.

Initial testing (Test 1) verified the immiscibility of the Jojoba and water oil phases. Accordingly,

- 6 ml of Jojoba oil and 20 ml of water were thoroughly mixed in a 30 ml beaker.
- After more than 2 hours, it was observed that the pale yellow colored Jojoba oil and water phases separated. The water phase was clear and also colorless indicating that the pale yellow jojoba oil was insoluble in the aqueous phase.

The next test (Test 2) was conducted as follows:

- 0.3 grams of the orange CoQ10 powder was added to 1 gram of PS80 and heated to about 50° C. The CoQ10 dissolved in the PS80 forming a red/orange colored solution. The CoQ10 remained solubilized and remained solubilized when the mixture was cooled to room temperature.
- Testing for supersaturation at room temperature was evaluated by the addition of a crystal to the solution to determine if precipitation occurred. It was observed that the CoQ10/PS80 concentrate was not supersaturated.
- 6 ml of Jojoba oil was mixed with 20 ml of water and the mixture was thoroughly stirred while heated to about 50° C.
- The water in oil mixture at 50° C. was then added to the CoQ10/PS80 concentrate and thoroughly stirred for about 1 minute.
- After a little more than 2 hours, it was noted that the water phase contained the CoQ10 as observed by the clear red/orange colored water phase. The Jojoba oil phase separated from the aqueous phase and appeared to have little, if any, dissolved CoQ10 as observed by the pale yellow colored jojoba oil phase distinct from the red/orange color of the aqueous phase indicative of the solubilized CoQ10/PS80 concentrate.

The final testing (Test 3) with CoQ10, Jojoba oil and water was carried out as follows:

- 0.3 grams of the CoQ10 powder were dissolved in 6 ml of Jojoba oil at room temperature. To this mixture was added 1 gram of PS80 and the resulting mixture was then heated to about 50° C.
- 20 ml of water which was preheated to about 50° C. was added to this mixture. The combined mixture was thoroughly stirred for 1 minute.
- After about 2 hours, it was visually observed that most of the CoQ10 did separate from the aqueous phase and was mostly concentrated in the red/orange Jojoba oil phase. Also, the
- aqueous phase was partially opaque and quite unlike the clear aqueous phase of the beaker in Test 2 which contained the bulk of the red/orange solubilized CoQ10.

As a consequence of these tests, it is concluded that the poorly soluble CoQ10 initially be solubilized in PS80 to form a concentrate in order to enhance its solubility in aqueous solutions.

Example 14—Preparation of Topical Formulations of Apigenin Using Apigenin/Surfactant Concentrates Active agent concentrates can be used to formulate compositions with a higher concentration of dissolved active agent in the prepared formulation than that achievable without the use of making the active agent concentrates first. Multiple prototype solution, gel, ointment, and emulsion topical formulations containing Apigenin in the dissolved state were prepared using a Apigenin/Polysorbate-80 concentrate and an Apigenin/PEG300 concentrate. These formulations are summarized in Tables XXII & XXIII.

TABLE XXII

Prototype Solution, Gel and Ointment, Formulations Prepared with Apigenin/Surfactant Concentrates

| | Apigenin dissolved in PS80 Concentrate | | | | | | | Apigenin dissolved in PEG300 Concentrate | | Apigenin dissolved in PS80 Concentrate | |
|---|---|---|---|---|---|---|---|---|---|---|---|
| | Anhydrous (DMSO/EtOH) | Anhydrous (EtOH + Oily enhancers) | Aqueous (NO EtOH) | Aqueous | Aqueous | Aqueous | Aqueous | Anhydrous PEG Solution | Anhydrous PEG Ointment | Aqueous gel (modified) | Control solution |
| Component | | | | % w/w | | | | | | | |
| Apigenin (API) | | | | | | | | | | | |
| Apigenin/PS80 concentrate (5.6% w/w APIGENIN) | 9 | 9 | 9 | 9 | 9 | 9 | 9 | | | 9 | 9 |
| Apigenin/PEG300 concentrate (3.5% w/w APIGENIN) | | | | | | | | 14.3 | 14.3 | | |
| Dimethyl sulfoxide (DMSO) | 45 | | 45 | | | | | | | | |
| Polysorbate 80 (PS80) | | | | | 21 | 10 | | | | | |
| Polyethylene glycol 300 (PEG 300, IIG max-57%) | | | | | | | | 14.7 | | | |

TABLE XXII-continued

Prototype Solution, Gel and Ointment, Formulations Prepared with Apigenin/Surfactant Concentrates

| | Apigenin dissolved in PS80 Concentrate | | | | | | Apigenin dissolved in PEG300 Concentrate | | Apigenin dissolved in PS80 Concentrate | |
|---|---|---|---|---|---|---|---|---|---|---|
| | Anhydrous (DMSO/EtOH) | Anhydrous (EtOH + Oily enhancers) | Aqueous (NO EtOH) | Aqueous | | | Anhydrous PEG Solution | Anhydrous PEG Ointment | Aqueous gel (modified) | Control solution |
| PEG 200 (IIG max-39%) | | | | | | | 39 | 13.7 | | |
| PEG 3350 (IIG max 40%) | | | | | | | | 40 | | |
| Span 80 | | | | | | 7 | | | | |
| Water | | | 34 | 46 | 33 | 36 | 72 | | 51.5 | 54 |
| 150 mM NaCl | | | | | | | | | | |
| Ethanol (EtOH) | 46 | 66 | | | 45 | | | | | |
| Propylene glycol (PG) | | 10 | 20 | | | | 20 | 20 | | |
| Isopropyl myristrate (IPM) | | | | | | | | | | |
| Transcutol (TC) | | | 25 | 25 | | | | | 25 | 25 |
| Dimethyl isosorbide (DMI) | | | | | | | | | | |
| Hexylene glycol (HG) | | 12 | 12 | 12 | 12 | 12 | 12 | 12 | 12 | 12 |
| Myristyl lactate (ML) | | 10 | | | | | | | | |
| Oleic acid (Oac) | | 5 | | | | | | | | |
| Oleyl alcohol (OA) | | | | | | | | | | |
| Sodium hyaluronate (NaH, Ultra low molecular weight) | | | | | | | | | 0.5 | |
| Sodium hyaluronate (NaH, High molecular weight [e.g. >100 KDa]) | | | | | | | | | 2.0 | |
| TOTAL | 100.0 | 100.0 | 100.0 | 100.0 | 100.0 | 100.0 | 100.0 | 100.0 | 100.0 | 100.0 |

TABLE XXIII

Emulsion Formulations Prepared with Apigenin/Surfactant Concentrates

| | Emulsions (0.25% w/w Apigenin) | |
|---|---|---|
| | Emulsifying Wax Base | Pemulen Base |
| Formulation # | 17 | 18 |
| Component | % w/w | |
| Apigenin 5.6%/PS80 Concentrate | 4.5 | 4.5 |
| Transcutol, USP | 10 | 10 |
| Methylparaben, NF | 0.17 | 0.17 |
| Propylparaben, NF | 0.03 | 0.03 |
| EDTA, USP | 0.1 | 0.1 |
| Purified water | QSad | |
| Carbopol 980 | 0.4 | 0.4 |
| Emulsifying wax, NF | 12 | |
| Pemulen TR1 | | 0.3 |
| White petrolatum, NF | 5 | |
| Myristyl lactate, NF | 5 | 12.2 |
| Cyclomethicone, NF | 2 | 10 |
| Oleyl alcohol, NF | 2 | 2 |
| Cholesterol, NF | 1 | |
| Butylated hydroxytoluene, NF (BHT) | 0.1 | 0.1 |
| Dilute HCl solution, NF | QSad pH7 | QSad pH7 |
| 10% NaOH Solution | | |
| Total | 100 | 100 |

Example 15—In Vitro Percutaneous Absorption of Apigenin from Formulations Using Human Skin Overall, data from this in vitro skin permeation experiment indicated that DPSI prototypes exhibited a range of delivery profiles from various formulation bases with contrasting organoleptic/cosmetic properties.

The purpose of this study was to characterize in vitro percutaneous absorption of Apigenin from topical formulations following application to excised human skin from elective surgery.

This study was conducted using procedures adapted from the FDA and AAPS Report of the Workshop on Principles and Practices of In Vitro Percutaneous Penetration Studies: Relevance to Bioavailability and Bioequivalence (Skelly et al., 1987). Human tissue from a single donor was dosed with 5 mg/cm$^2$ of formulation. The compositions of all the formulations evaluated in this study are summarized in Table XXIV and XXV.

The clinically relevant dose of 5 mg/cm$^2$ was applied to dermatomed human abdominal tissue from a single donor obtained following elective surgery. The thickness of the tissue ranged from 0.034 inches (0.870 mm) with a mean+/− standard deviation in thickness of +/−0.005 inches (+/−0.131 mm) and a coefficient of variation of 15%.

Percutaneous absorption was evaluated using this human abdominal tissue from a single donor mounted in Bronaugh flow-through diffusion cells. The cells were maintained at a constant temperature of 32° C. by use of recirculating water baths. These cells have a nominal diffusion area of 0.64 cm$^2$. Fresh receptor phase (PBS, pH 7.4, containing 0.1% sodium azide and 4% Bovine Serum Albumin) was continuously pumped under the tissue at a flow rate of nominally 0.25 ml/hr and collected in 6-hour intervals. The receptor phase samples were collected in pre-weighed scintillation vials; the post weights were taken at the end of the study. Following the 24-hour duration exposure, the formulation residing on the tissue surface was removed by tape-stripping with CuDerm D-Squame stripping discs. The epidermis, dermis, and receptor phase samples were labeled and frozen prior to subsequent analysis of Apigenin content by LC-MS/MS and ultimate sample disposal.

Generally, permeation of Apigenin into the receptor compartment was low. However, relatively high permeation into the receptor phase was achieved when Apigenin was applied in neat DMSO. Moderate dermal deposition was observed while relatively high epidermal values were associated with the majority of the compositions evaluated. Overall, DMSO based solutions, 3530-14A, -15B and -31 (neat DMSO control) produced the highest tissue penetration and deposition. An anhydrous solution (3530-14B, EtOH/PG/IPM/ML/Oleic acid) also offered relatively favorable delivery characteristics. Although formulation 3530-14B generated lower tissue penetration and deposition to than the DMSO based solutions it may offer a viable alternative. As anticipated, the PEG based solution produced greater delivery than the PEG ointment.

Several semi-solid prototypes were evaluated and included an aqueous gel (3530-22), an aqueous gel based nano-suspension (3530-24), two emulsions (3530-29 [Emulsifying wax base] and -30 [Pemulen base]) and a PEG ointment (3530-18B). It was notable that the presence of Sodium hyaluronate polymer in the aqueous gel did not significantly impair receptor penetration and dermal deposition when compared to the analogous solution control. In terms of delivery efficiency (% of applied dose) of Apigenin, the Pemulen emulsion offered slightly more favorable delivery characteristics relative to a solubilized Apigenin/Sodium hyaluronate based gel (3530-22). When amount delivered was considered, the aqueous gel (3530-22) generated higher tissue deposition than the Pemulen emulsion. However, the Pemulen emulsion generated the highest receptor levels of the semi-solid compositions tested, when efficiency and amount delivered were evaluated.

FIG. 3 is a graphical illustration of the epidermal, dermal, receptor fluid and total penetration apigenin profiles as a percentage of the applied apigenin dosage content for the several topical formulations.

TABLE XXIV

SOLUTION AND GEL COMPOSITIONS

| Apigenesis Formulation concepts | Apigenin dissolver in PS80 Concentrate | | | Apigenin dissolved in PEG300 Concentrate | | Apigenin dissolved in PS80 Concentrate | | | Nano-suspension | |
|---|---|---|---|---|---|---|---|---|---|---|
| | Anhydrous (DMSO/EtOH) | Anhydrous (EtOH + Oily enhancers) | Aqueous | Anhydrous PEG Solution | Anhydrous PEG Ointment | Aqueous gel (modified) | Control solution | Aqueous gel (modified) | | DMSO Control |
| Formulation # | 1 | 2" | 4 | 9 | 10 | 13 | 14 | 15 | | n/a |
| Formulation ID: 3530- | 14A | 14B | 15B | 18A | 18B | 22 | 23 | 24 | | 31 |
| Component | | | | % w/w | | | | | | |
| Apigenin (API) | | | | | | | | 0.5 | | 1.5 |
| Apigenin/PS80 concentrate (5.6% w/w Apigenin) | 9 | 9 | 9 | | | 9 | 9 | | | |
| Apigenin/PEG300 concentrate (3.5% w/w Apigenin) | | | | 14.3 | 14.3 | | | | | |
| Dimethyl sulfoxide (DMSO) | 45 | | 45 | | | | | | | 98.5 |
| Polysorbate 80 (PS80) | | | | | | | | | | |
| Polyethylene glycol 300 (PEG 300, IIG max-57%) | | | | 14.7 | | | | | | |
| PEG 200(IIG max-39%) | | | | 39 | 13.7 | | | | | |
| PEG 3350 (IIG max 40%) | | | | | 40 | | | | | |
| Span 80 | | | | | | | | | | |
| Water | | | 46 | | | 51.5 | 54 | 60 | | |
| 150 mM NaCl | | | | | | | | | | |
| Ethanol (EtOH) | 46 | 66 | | | | | | | | |
| Propylene glycol (PG) | | 10 | | 20 | 20 | | | | | |
| Isopropyl myristate (IPM) | | | | | | | | | | |
| Transcutol (TC) | | | | | | 25 | 25 | 25 | | |
| Dimethyl isosorbide (DMI) | | | | | | | | | | |
| Hexylene glycol (HG) | | | | 12 | 12 | 12 | 12 | 12 | | |
| Myristyl lactate (ML) | | 10 | | | | | | | | |
| Oleic acid (OAc) | | 5 | | | | | | | | |
| Oieyl alcohol | | | | | | | | | | |
| Sodium hyaluronate (NaH, Ultra low molecular weight) | | | | | | 0.5 | | 0.5 | | |
| Sodium hyaluronate (NaH, High molecular weight [e.g. >100 KDa]) | | | | | | 2.0 | | 2.0 | | |
| TOTAL | 100.0 | 100.0 | 100.0 | 100.0 | 100.0 | 100.0 | 100.0 | 100.0 | | 100.0 |
| Formulation Labels | A | B | C | D | E | F | G | H | | K |

TABLE XXV

EMULSION COMPOSITIONS

| | Emulsions (0.25% w/w Apigenin) | |
|---|---|---|
| Apigenesis Formulation concepts | Emulsifying Wax Base | Pemulen Base |
| Formulation # | 17 | 18 |
| Formulation ID: 3530- | 29 | 30 |
| Component | % w/w | |
| Apigenin 5.6%/PS80 Concentrate | 4.5 | 4.5 |
| Transcutol P | 10 | 10 |
| Methylparaben, NF | 0.17 | 0.17 |
| Propylparaben, NF | 0.03 | 0.03 |
| EDTA, USP | 0.1 | 0.1 |
| Purified water | QSad | |
| Carbopol 980 | 0.4 | 0.4 |
| Emulsifying wax, NF | 12 | |
| Pemulen TR1, NF | | 0.3 |

TABLE XXV-continued

EMULSION COMPOSITIONS

| Apigenesis Formulation concepts | Emulsions (0.25% w/w Apigenin) | |
|---|---|---|
| | Emulsifying Wax Base | Pemulen Base |
| White petrolatum, NF | 5 | |
| Myristyl lactate | 5 | 12.2 |
| Cyclomethicone | 2 | 10 |
| Oleyl alcohol | 2 | 2 |
| Cholesterol, NF | 1 | |
| Butylated hydroxytoluene, NF (BHT) | 0.1 | 0.1 |
| Dilute HCl solution, NF | | QSad pH 6.5 |
| 10% NaOH Solution | | |
| Total | 100.0 | 100.0 |
| Formulation Label: ⟶ | I | J |

Example 16—In Vitro Irritancy Determination of Apigenin Formulations

The purpose of this study was to compare the acute dermal irritation potential of 5 Apigenin containing formulations using the Epiderm MTT $ET_{50}$ assay. The time required for atest article to reduce tissue viability to 50%, i.e. $ET_{50}$, correlates well with the traditional in vivo rabbit skin irritation test This study was conducted at MB Research Laboratories (Spinnerstown, Pa. to conduct the EpiDerm MTT Assay. EpiDerm tissue was incubated with Api Genesis formulations for 1, 4 and 24 hours (two tissues per time point for each test article). Triton X-100, 1%, was used as positive control. After incubation, the tissues were rinsed to remove test articles and cytotoxicity was determined with MTT dye [3-(4,5-Dimethylthiazol-2-yl)-2,5-diphenyltetrazolium bromide, Thiazolyl blue]. Only viable cells are capable of enzymatic reduction of MTT into a purple formazan product that is quantitatively measured following extraction from the tissue. Dead cells do not reduce MTT and thus, this assay allows determination of the effect of test article exposure on tissue viability when compared to untreated control tissues.

Tissue viability data at the three incubation time points were used to calculate the time required to reduce tissue viability to 50% (Effective Time, $ET_{50}$) for each formulation. The $ET_{50}$ is well correlated with the traditional Draize rabbit skin irritation test dermal scores and used to predict irritancy class (Table XXVI).

TABLE XXVI

Epiderm MTT $ET_{50}$ assay-in vivo Draize Irritancy Correlation

| $ET_{50}$ (h) | Expected in vivo Irritancy |
|---|---|
| <0.5 | Severe, Probable corrosive |
| 0.5-4 | Moderate |
| 4-12 | Moderate to Mild |
| 12-24 | Very Mild |
| >24 | Non-Irritating |

Table XXVII presents the ranking of test articles based on unaudited $ET_{50}$ values and their predicted in vivo irritancy classification. These formulations ranged from non-irritants to mild-to-moderate irritants.

TABLE XXVII

Formulations Irritancy Classification

| Formulation ID (refer to "Formulation Labels" on Tables XXIV and Table XXV) | $ET_{50}$ (h) | Predicted in vivo Irritancy Classification |
|---|---|---|
| (J) 3530-30 | >24.0 | Non-Irritating |
| (C) 3530-15B | >24.0 | Non-Irritating |
| (F) 3530-22 | 12.6 | Very Mild |
| (H) 3530-24 | 11.11 | Mild to Moderate |
| (B) 3530-14B | 8.0 | Mild to Moderate |

The formulations can be ranked, based on ET50 values, as follows:

[non-irritant] $(J)=(C)<F\approx(H)<(B)$ [mild-to-moderate]

The ET50 for the positive control 1% Triton X-100, was 5.9 hours and was within the manufacturer's historical range for the assay, which confirmed that the test system is sensitive to irritants.

In summary, the In Vivo irritancy Determinations of the 5 formulations ranged from non-irritating to mild-to-moderate irritating and are considered to have low acute skin irritation potential.

It should be understood that a wide range of changes and modifications could be made to the embodiments described above. It is therefore intended that the foregoing description illustrates rather than limits this invention, and that it is the following claims, including all equivalents, which define this invention.

All documents and references cited above are hereby incorporated by reference in their entirety in this application.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all.

The invention claimed is:

1. A composition comprising:
a concentrate formed by mixing a polyphenol with a non-ionic surfactant, in the absence of a carrier, to form a mixture, and heating said mixture to a temperature of greater than 150° C. to form said concentrate, wherein upon cooling to room temperature the concentrate is not supersaturated, and the concentration of said polyphenol is greater than the saturation concentration of said polyphenol in said non-ionic surfactant.

2. The composition as in claim 1, wherein said non-ionic surfactant is a polysorbate.

3. The composition as in claim 1 further comprising hyaluronic acid.

4. The composition as in claim 1, wherein said polyphenol and said non-ionic surfactant are heated to a temperature of greater than 170° C.

5. The composition as in claim 1 further comprising a carrier.

6. The composition as in claim 5, wherein said carrier is a water based carrier.

7. The composition as in claim 5, wherein said carrier comprises dimethyl sulfoxide and water.

8. The composition as in claim 5, wherein said carrier comprises dimethyl sulfoxide, hydroxypropyl cellulose and water.

9. The composition as in claim 5, wherein said carrier comprises ethanol, propylene glycol and water.

10. The composition as in claim 5, wherein said carrier comprises ethanol, propylene glycol, water and a gelling agent selected from the group consisting of hydroxyethyl cellulose, sodium hyaluronate and a crosslinked polyacrylate polymer.

11. The composition as in claim 5, wherein said carrier comprises an oil phase, a surfactant, and water.

12. The composition as in claim 11, wherein said oil phase comprises ethoxydiglycol, myristyl lactate, cyclomethicone or oleyl alcohol.

13. The composition as in claim 5, wherein said carrier is an oil based carrier.

14. The composition as in claim 5, wherein said carrier comprises an alcohol, ethoxydiglycol, propylene glycol, hexylene glycol, butylene glycol, dipropylene glycol, glycerin, water, saline, DMSO, isopropyl myristate, mineral oil, a surfactant, or dimethyl isosorbide.

15. The composition as in claim 1, wherein said non ionic surfactant is polysorbate 80, polyoxy 20 cetostearyl ether, or polyoxyl 40 hydrogenated castor oil.

16. The composition as in claim 1, wherein said composition is in the form of a pharmaceutical.

17. The composition as in claim 1, wherein said composition is in the form of a nutraceutical, cosmeceutical, food or medical food.

18. The composition as in claim 1, wherein said composition is in the form of a beverage.

19. The composition as in claim 1, wherein said composition is in the form of a solution or emulsion.

20. The composition as in claim 1, wherein said composition is in the form of a gelatin capsule or enteric coated capsule.

21. The composition as in claim 1, wherein said composition is in the form of a liquid, serum, cream, lotion, gel, spray, foam, ointment or cleanser.

22. The composition as in claim 1, further comprising one or more additive selected from the group consisting of hyaluronic acid, a preservative, a buffer, a humectant, an anti-inflammatory agent, an emollient, a moisturizer, a thickening agent, and an analgesic.

* * * * *